United States Patent [19]
Yaremko et al.

[11] Patent Number: 5,620,898
[45] Date of Patent: Apr. 15, 1997

[54] AUTOMATED BLOOD ANALYSIS SYSTEM

[75] Inventors: Mykola Yaremko, Livingston; Rosemary Chachowski, Manville, both of N.J.; Marcel Frischknecht, Oberduerten, Switzerland; Gregor Batliner, Hombrechtikon, Switzerland; Linus Flueler, Bubikon, Switzerland; Marco Forster, Grueningen, Switzerland; Martin Gander, Landquart, Switzerland; Beat Gretener, Meilen, Switzerland; Walter Imfeld, Hombrechtikon, Switzerland; Hansjoerg Kunz, Zurich, Switzerland; Martin Kuster, Eschenbach, Switzerland; Karl Puchegger, Salzburg, Austria

[73] Assignee: Ortho Diagnostic Systems Inc., Raritan, N.J.

[21] Appl. No.: 463,852

[22] Filed: Jun. 5, 1995

Related U.S. Application Data

[62] Division of Ser. No. 163,997, Dec. 8, 1993, which is a continuation of Ser. No. 75,303, Jun. 11, 1993, abandoned.

[51] Int. Cl.⁶ .................................................. G01N 35/10
[52] U.S. Cl. ..................... 436/45; 436/43; 436/47; 436/49; 436/177; 436/480; 422/63; 422/64; 422/72
[58] Field of Search ......................... 436/43, 45, 47, 436/48, 49, 54, 165, 174, 177, 179, 180; 422/63, 64, 65, 72, 73, 100, 104

[56] References Cited

U.S. PATENT DOCUMENTS

| | | | |
|---|---|---|---|
| 4,058,367 | 11/1977 | Gilford | 422/65 |
| 4,208,484 | 6/1980 | Sogi et al. | 435/286 |
| 4,678,752 | 7/1987 | Thorne et al. | 435/291 |
| 4,683,120 | 7/1987 | Meserol et al. | 422/72 |
| 4,708,940 | 11/1987 | Yoshida et al. | 436/45 |
| 5,089,230 | 2/1992 | Kondo et al. | 422/64 |
| 5,158,895 | 10/1992 | Ashihara et al. | 436/526 |
| 5,171,532 | 12/1992 | Columbus et al. | 422/72 |
| 5,176,880 | 1/1993 | Iwasaki et al. | 422/63 |
| 5,215,714 | 6/1993 | Okada et al. | 422/64 |
| 5,389,339 | 2/1995 | Petschek et al. | 422/64 |

FOREIGN PATENT DOCUMENTS 9205448  4/1992  WIPO.

Primary Examiner—Long V. Le

[57] ABSTRACT

A blood analysis system or instrument, generally, including an incubator station, a sample and reagent holding station, a pipette assembly, a centrifuge, an analysis station, and a transport assembly. Generally, the incubation station holds containers while reagents and fluids are being dispensed in those containers, and, if desired, for incubating the containers. The sample and reagent holding station holds samples and a plurality of reagents, and the pipette assembly transfers fluids from that sample and reagent holding station to containers in the incubation station. The centrifuge is provided for centrifuging the container, and the analysis station is provided to analyze the containers optically to identify reactions therein. The transport assembly carries the containers between the incubator station, the centrifuge, and the analysis station. Preferably, the pipette assembly is automatically operated to draw fluids and preselected reagents from the sample and reagent holding station, and to dispense fluids into the containers held in the incubation station to produce predetermined solutions therein. Also, the transport subassembly is automatically operated to carry containers from the incubator station to the centrifuge after the predetermined solutions have been produced in the containers, and then to carry the containers from the centrifuge to the analysis station.

9 Claims, 58 Drawing Sheets

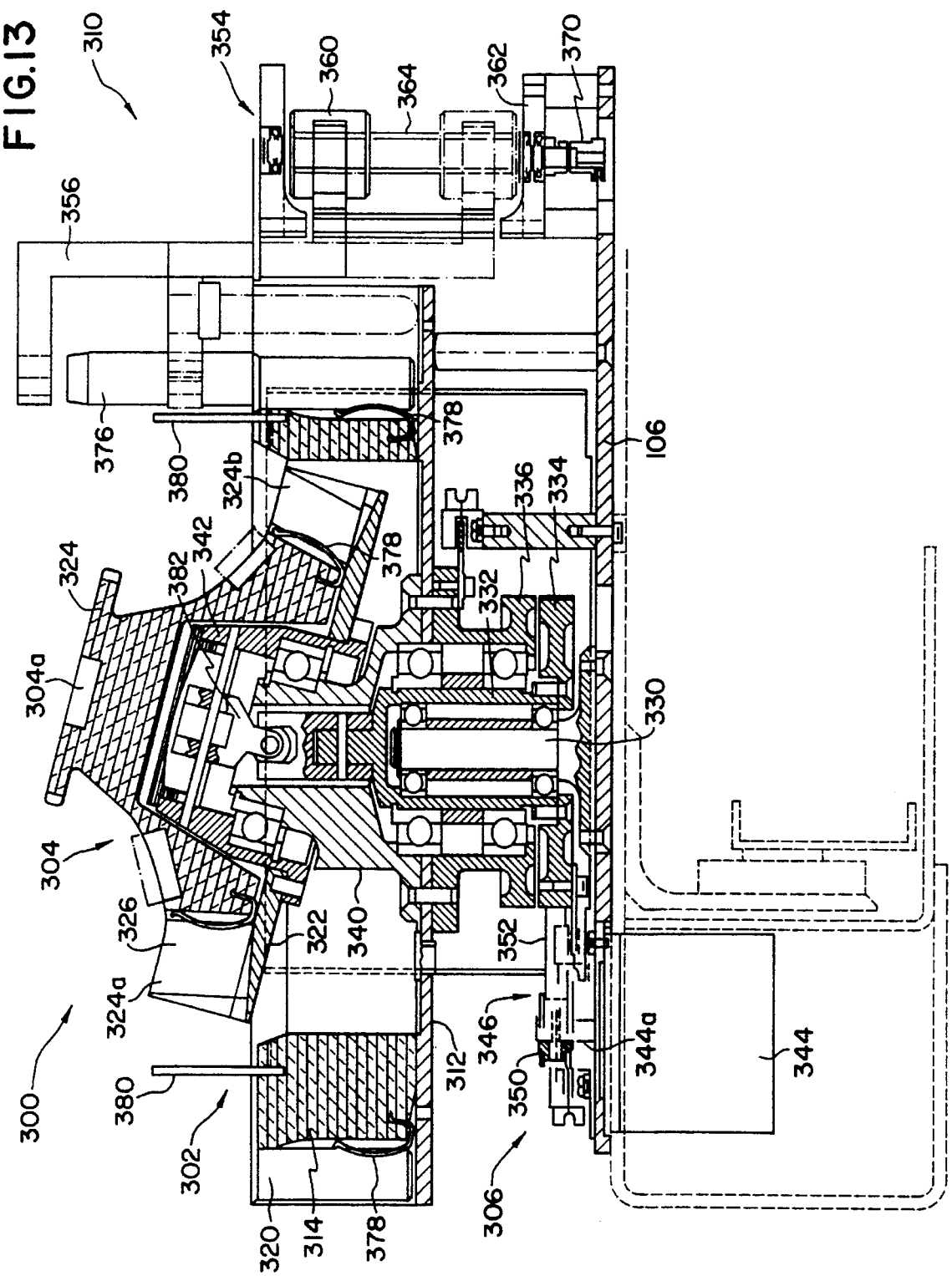

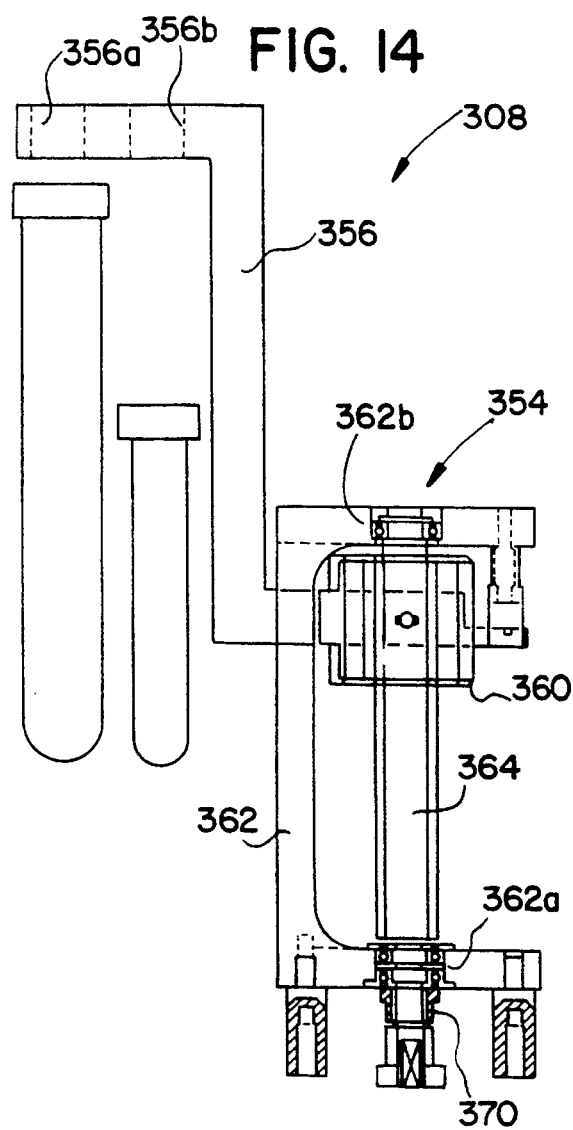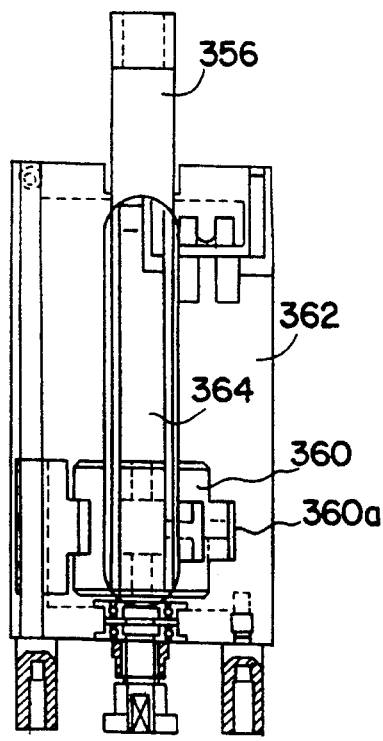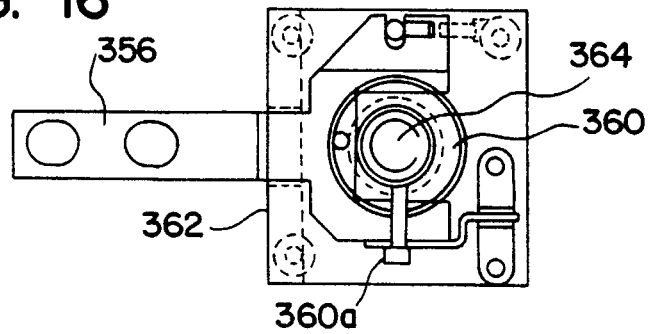

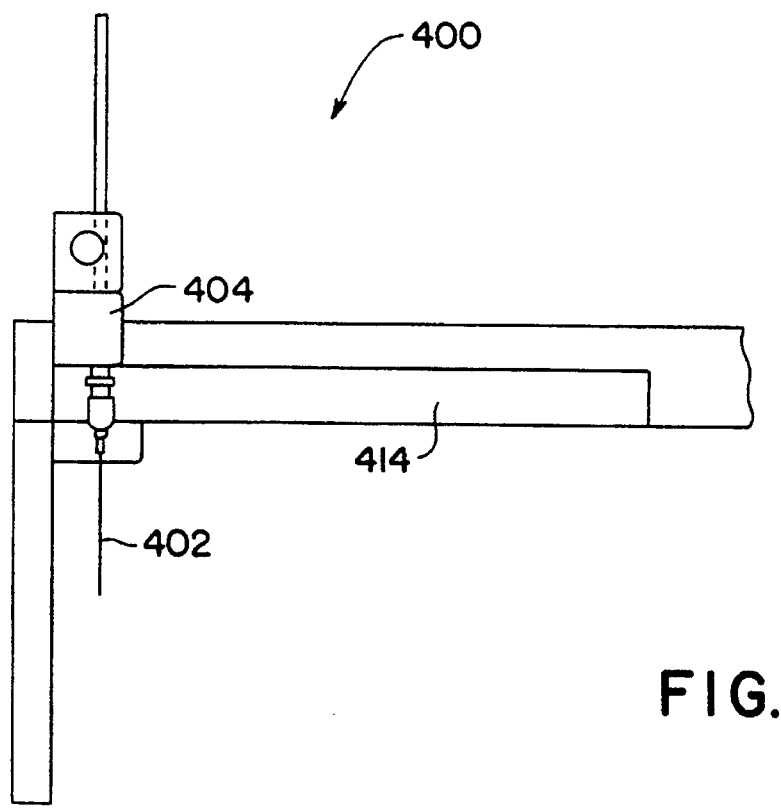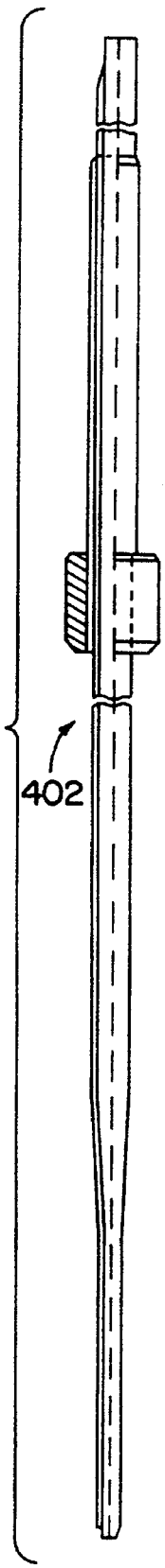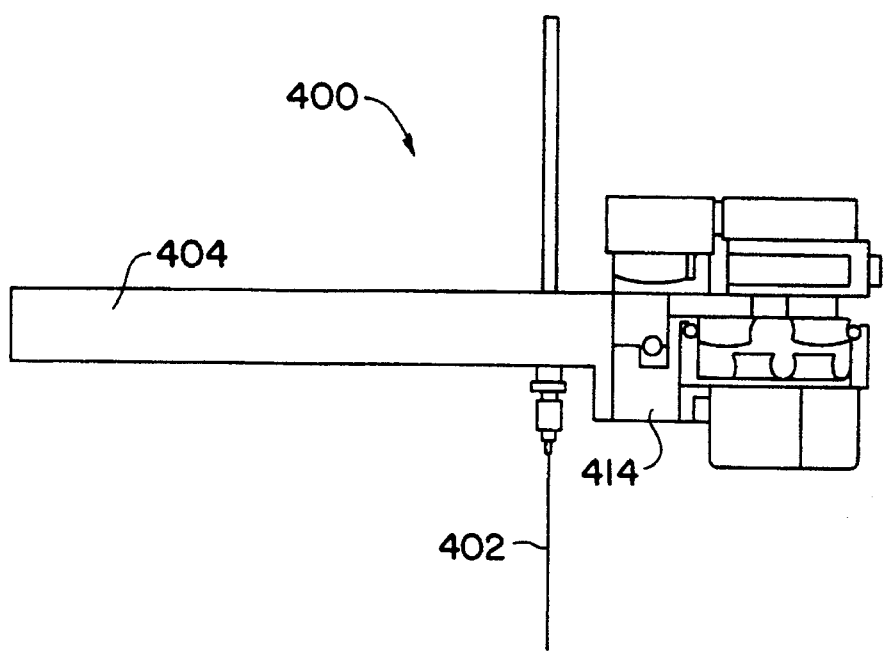

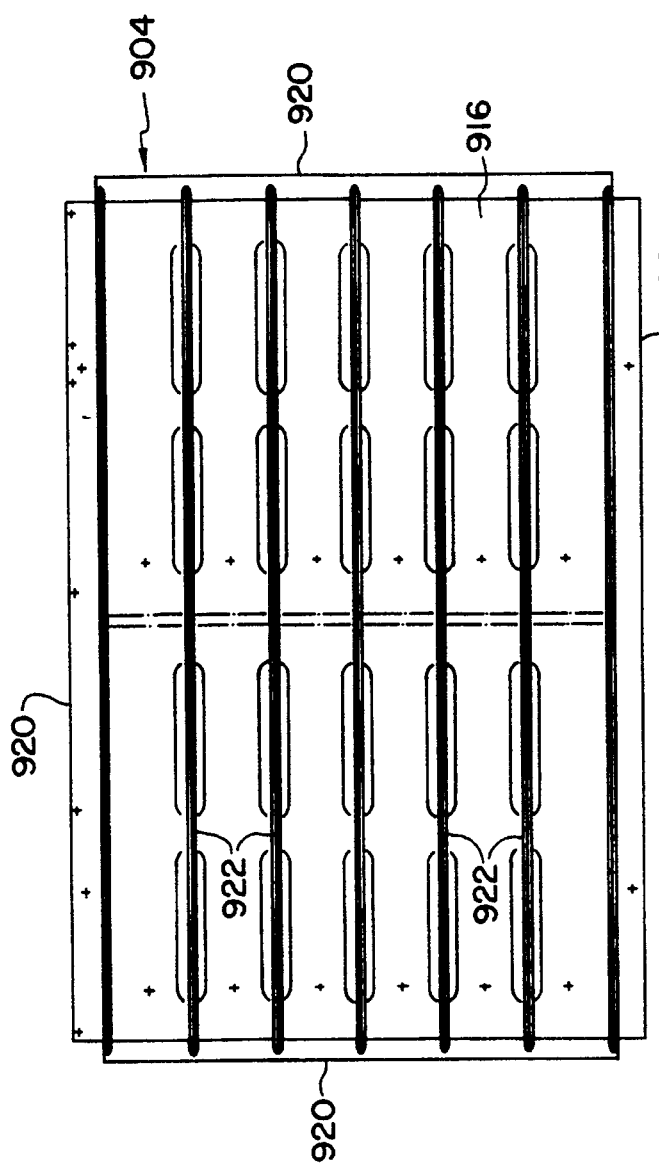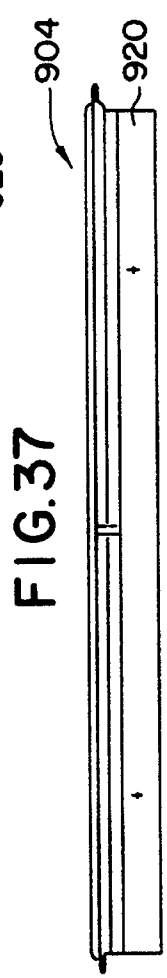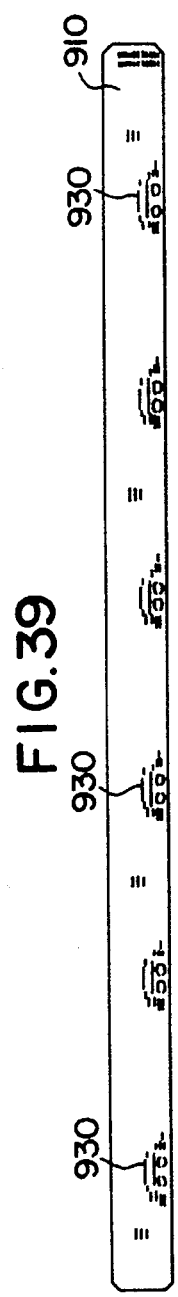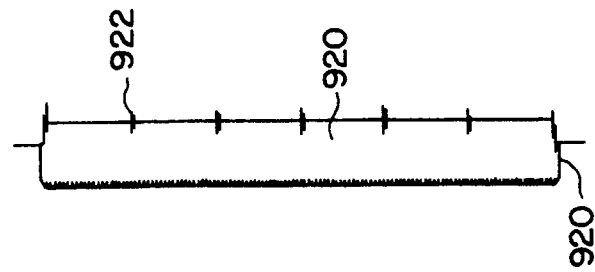

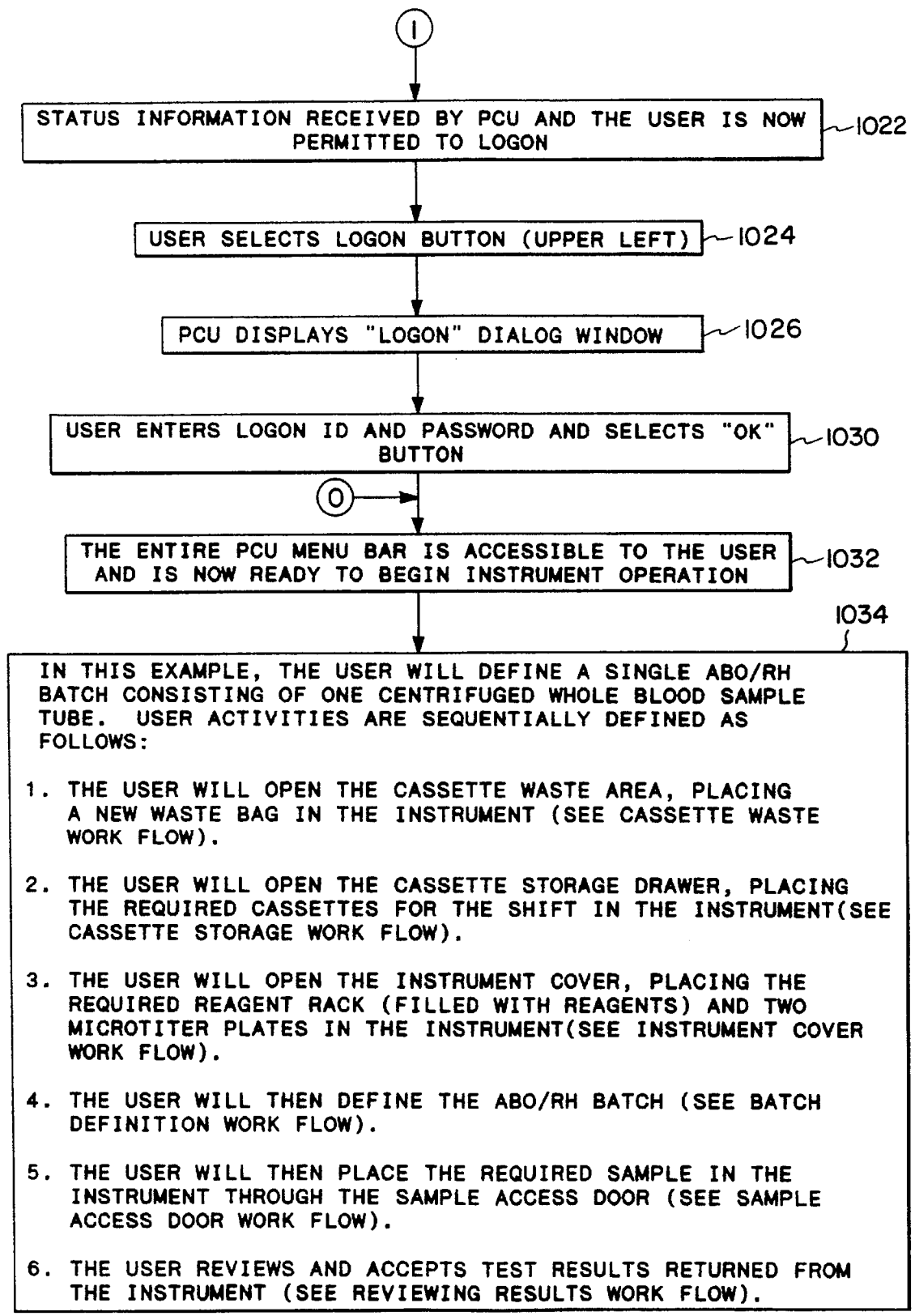

FIG.42B

```
                        ASSUMPTIONS:
1.  NO CASSETTES ARE RESIDING IN THE CASSETTE STORAGE DRAWER.
    THE DRAWER IS EMPTY.
2.  THE REAGENT RACK (AND REAGENTS) IS NOT IN THE INSTRUMENT.
3.  THE WASTE BAG FOR CASSETTES IS NOT IN THE INSTRUMENT AND
    NEEDS TO BE INSTALLED.
4.  SAMPLE RACKS AND SAMPLES ARE NOT IN THE INSTRUMENT.
```

6. THE SAMPLE ROTOR ROTATES, MOVING THE SAMPLE RACK TYPE BARCODE LABEL ON THE SAMPLE RACK INTO SCANNING POSITION. THE BARCODE IS READ, IDENTIFYING THE PHYSICAL CHARACTERISTICS

1120

7. THE SAMPLE ROTOR ROTATES, MOVING EACH SAMPLE TUBE POSITION IN THE RACK INTO BARCODE SCANNING POSITION. EACH TUBE IN THE RACK IS THEN SEQUENTIALLY READ.

ANOTHER SAMPLE RACK? — YES

NO

1122

8. THE PIPETTE IS THEN MOVED OVER THE FIRST WELL OF THE CELL DILUTION RACK, WHERE PRESENCE OF LIQUID IS CHECKED. THE ABSENCE OF LIQUID IN THE WELL INDICATES A NEW MICRO-TITER PLATE.

1124

9. THE SAME AS #8 ABOVE EXCEPT FOR THE SECOND CELL DILUTION RACK.

1126

10. THE PIPETTE IS MOVED TO ITS PARK POSITION OVER THE SHALLOW WASH AREA.

1130

11. THE GRIPPER IS MOVED TO ITS PARK STATION NEAR THE SPECIAL CASSETTE RACK.

1132

12. THE REAGENT ROTOR IS SET IN MOTION, KEEPING THE REAGENT CELLS IN SUSPENSION.

1134

ONCE INITIALIZATION ACTIVITIES ARE COMPLETE, CONFIRMATION OF THE ACTIVITY IS SENT TO THE PCU. HOWEVER, ERRORS DETECTED DURING ANY OF THE STEPS DESCRIBED ABOVE RESULT IN AN ERROR MSG(S) SENT TO THE PCU.

END

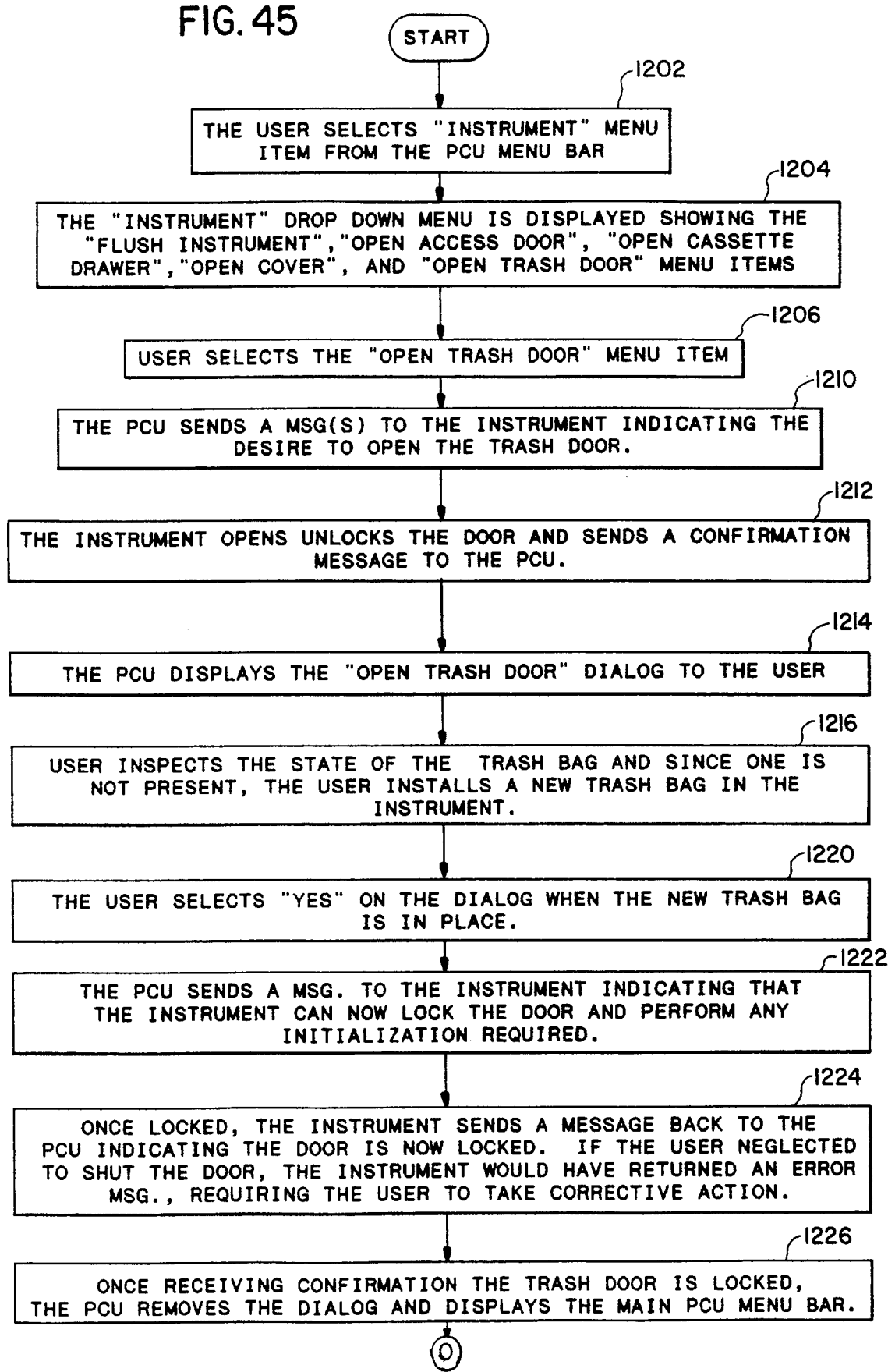

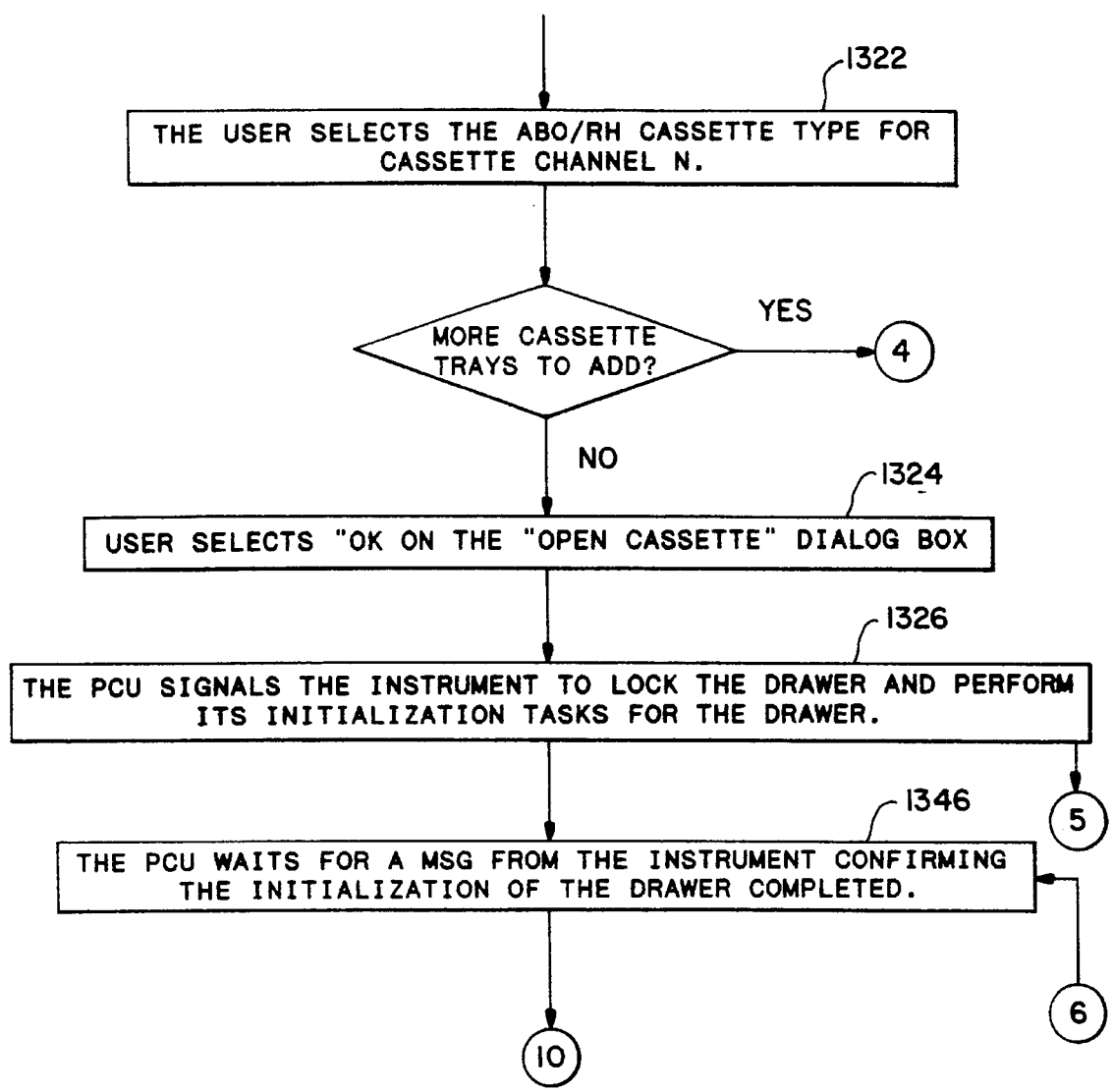

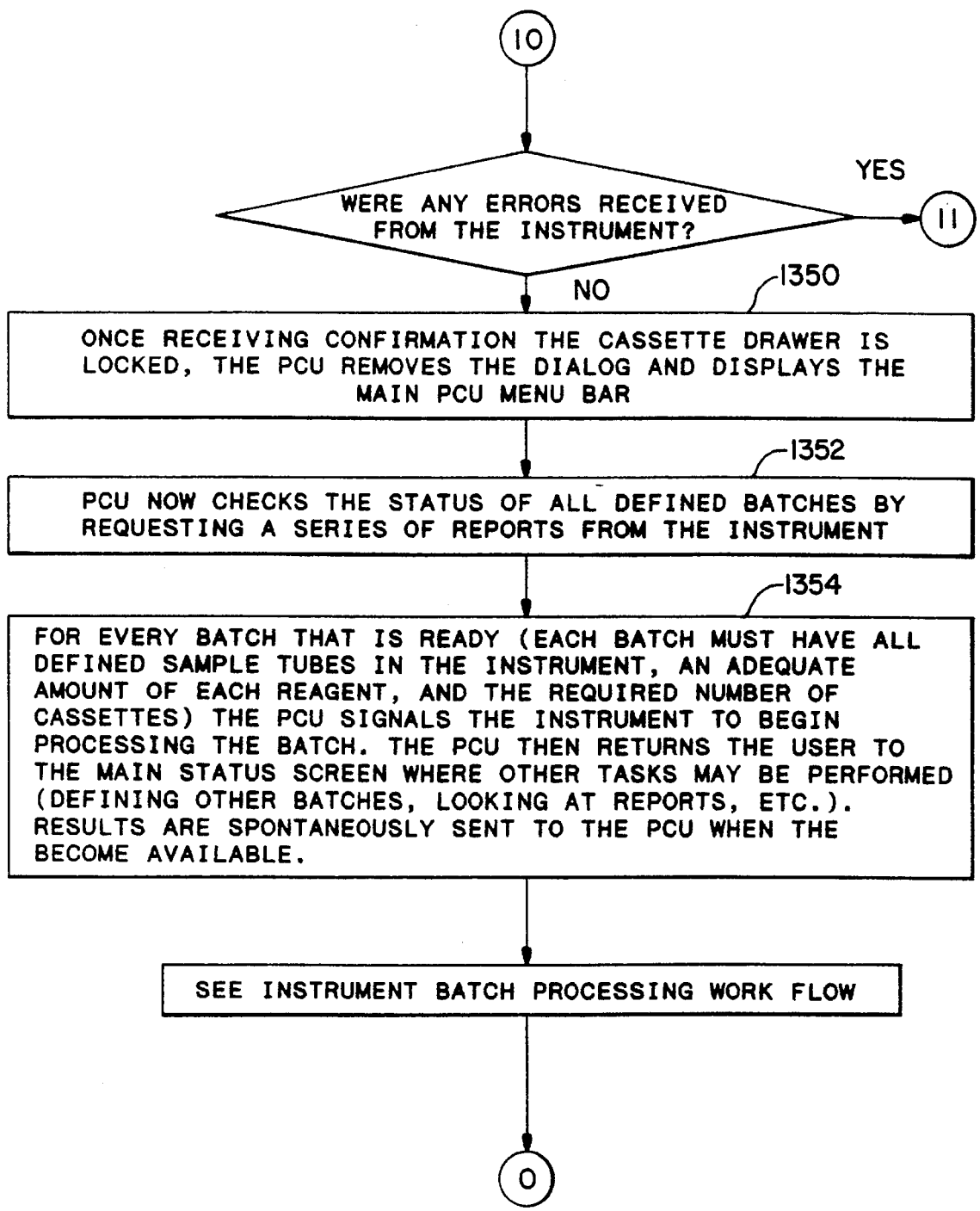

FIG. 55A

ASSUMPTION: A SINGLE ABO/Rh BATCH CONSISTING OF ONE PATIENT SAMPLE TUBE CONTAINING CENTRIFUGED WHOLE BLOOD.

START

1702 — INSTRUMENT RECEIVES A MSG. FROM THE PCU INSTRUCTING IT TO START A SPECIFIC BATCH.

1704 — THE CASSETTE DRAWER POSITIONS ITSELF FOR ABO/Rh CASSETTE REMOVAL BY THE GRIPPER.

1706 — THE GRIPPER MOVES FROM ITS CURRENT POSITION TO A POSITION OVER THE CHANNEL CONTAINING THE ABO/Rh CASSETTES. THE GRIPPER THEN TRAVELS IN THE Z DIRECTION, REMOVING A SINGLE ABO/Rh CASSETTE FROM THE CHANNEL.

1710 — THE GRIPPER POSITIONS ITSELF IN FRONT OF THE FIXED POSTION BARCODE SCANNER AND HORIZONTALLY MOVES THE CASSETTE PAST THE READER.

1712 — THE INSTRUMENT READS THE CASSETTE BARCODE LABEL, RETRIEVING THE CASSETTE'S EXPIRATION DATE, CASSETTE TYPE II, UNIQUE SEQUENCE NUMBER, AND LOT NUMBER.

1714 — THE GRIPPER MOVES THE CASSETTE OVER THE OUTER RING OF THE INCUBATOR MODULE.

1716 — THE INCUBATOR ROTOR ROTATES TO AN AVAILABLE POSITION FOR CASSETTE DEPOSIT.

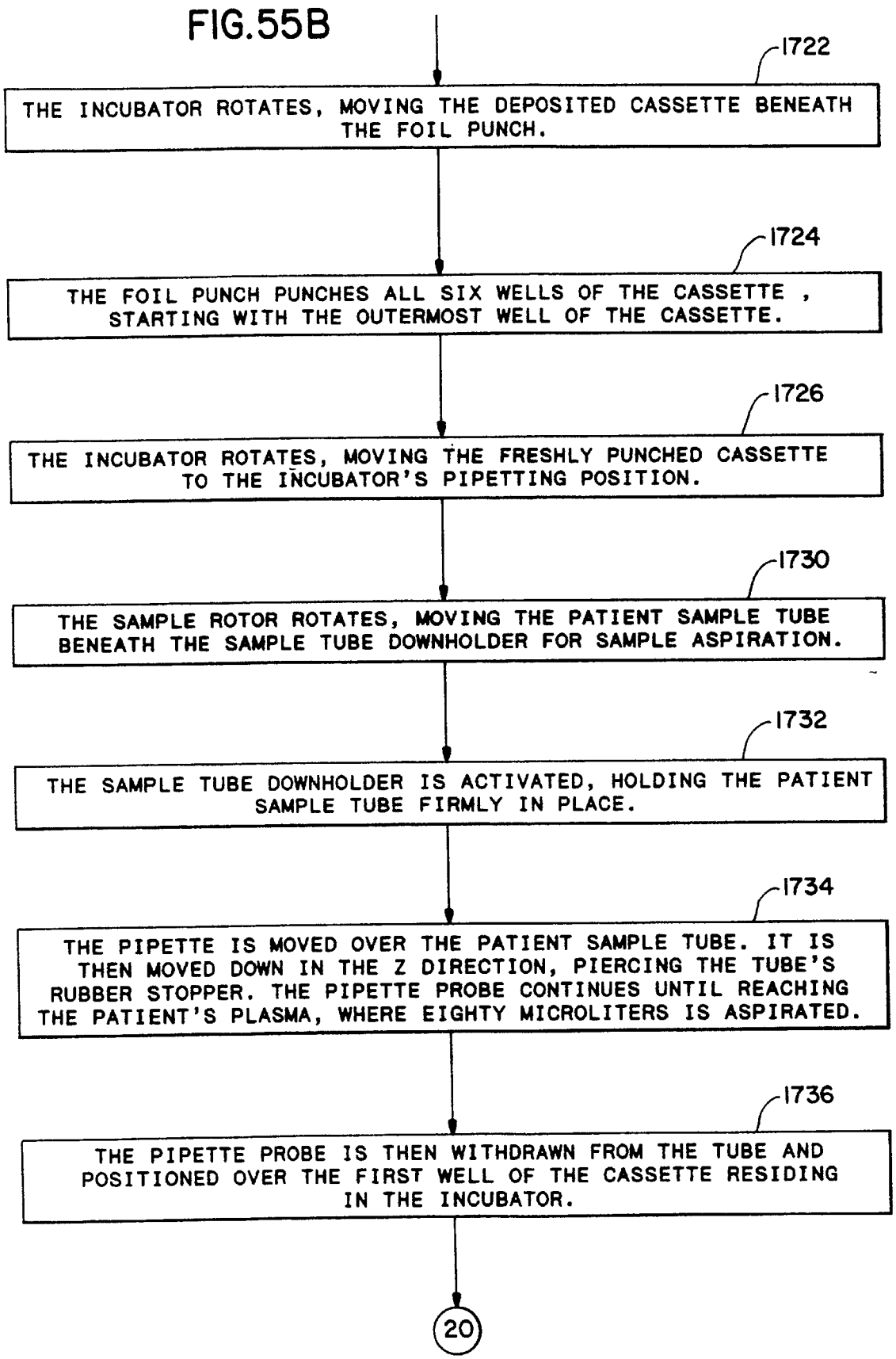

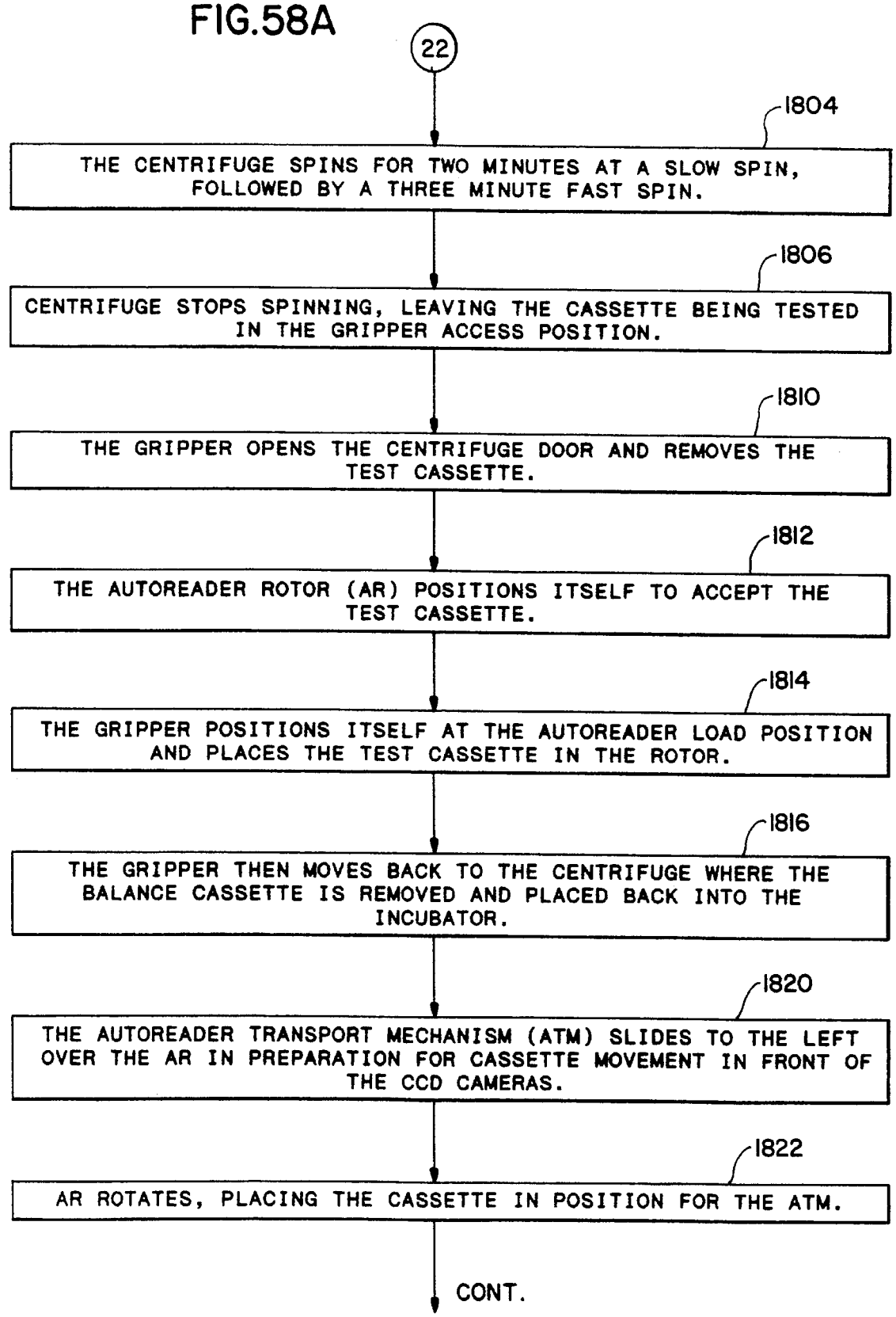

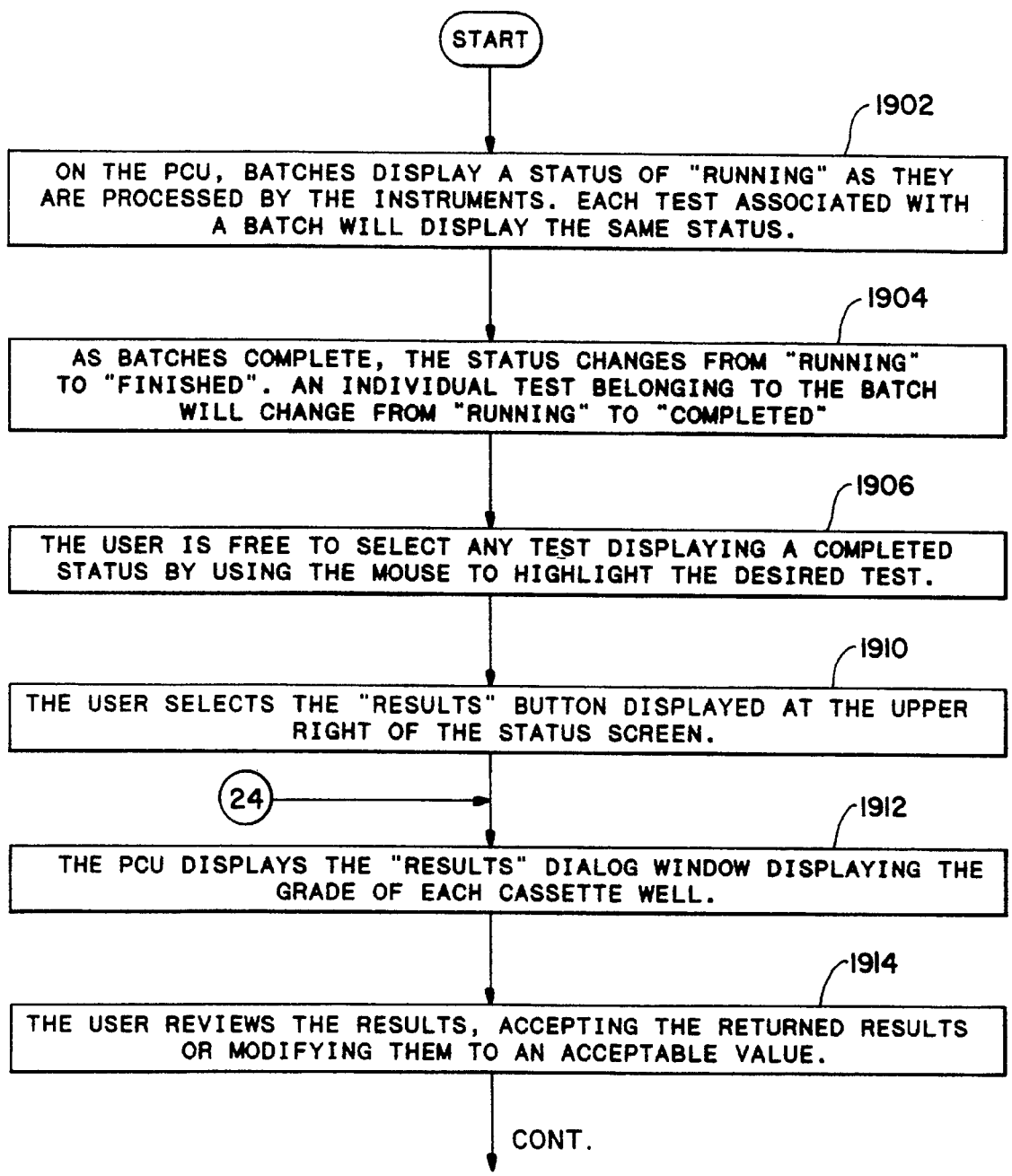

AUTOMATED BLOOD ANALYSIS SYSTEM

This is a divisional of application Ser. No. 08/163,997, filed on Dec. 8, 1993, which is a continuation of Ser. No. 075,303, filed on Jun. 11, 1993, now abandoned.

BACKGROUND OF THE INVENTION

This invention generally relates to systems and methods for analyzing solutions such as blood samples, and more specifically, to such systems and methods that analyze blood samples by detecting and quantifying agglutinates formed in those samples in response to immunological reactions. Even more particularly, the invention relates to an automated system and method for analyzing blood samples in this way.

Immunological agglutination reactions are used for identifying various kinds of blood types and for detecting various kinds of antibodies and antigens in blood samples and other aqueous solutions. In a conventional procedure, a sample of red blood cells is mixed with serum or plasma in test tubes or microplates, and the mixture may then be incubated and centrifuged. Various reactions either occur or do not occur depending on, for example, the blood type of the red blood cells or whether certain antibodies are present in the blood sample. Typically, these reactions manifest themselves as clumps of cells or particles with antigens or antibodies on their surfaces, referred to as agglutinates. Thus, the absence of any such clumps indicates that no reaction has occurred; and the presence of such clumps indicates that a reaction has occurred, with the size and amount of such clumps being a quantitative indicator of the level or concentration in the sample, or an indicator of the reaction strength, affinity of the complex for which the blood sample was tested.

Recently, a new agglutination test method—referred to as column agglutination technology, or CAT—has been developed. Column Agglutination Technology may be defined as the analysis of blood and blood products utilizing filtration as a means of separating agglutinated, precipitated, absorbed or adsorbed particulate components from non-reactive components for immunoassay applications. In this method, gel or glass bead microparticles are contained within a small column, referred to as a microcolumn. A reagent such as anti-A is dispensed in a diluent in the microcolumn and test red blood cells are placed in a reaction chamber above the column. The column, which is typically one of a multitude of columns formed in a transparent cassette, is centrifuged. The centrifuging accelerates the reaction, if any, between the reagent and the blood cells, and also urges any cells toward the bottom of the column. The glass beads or gel in the microcolumn act as a filter, however, and resist or impede downward movement of the particles in the column. As a result, the nature and distribution of the particles in the microcolumn after centrifuging provides a visual indication of whether any agglutination reaction occurred in the microcolumn, and if so, of the strength of that reaction.

In particular, if no agglutination reaction occurs, then all or virtually all of the red blood cells in the microcolumn pass downward, during centrifuging, to the bottom of the column and form a pellet at that bottom. If there is a very strong reaction between the reagent and the red blood cells, virtually all of the red blood cells agglutinate, and large agglutinates form at the top of the microcolumn, above the gel or glass beads contained therein. The gel or glass beads prevent the agglutinates from passing, during centrifuging, to the bottom of the column, so that after centrifuging the agglutinates remain on the surface of the gel or beads.

If there is a reaction between the reagent and the blood cells, but this reaction is not as strong as the above-described very strong reaction, then some but not all of the red blood cells agglutinate. The percentage of red blood cells that agglutinate and the size of the agglutinated particles both vary directly with the strength of the reaction. During centrifuging, the unreacted blood cells pass to the bottom of the column, and the distance that the agglutinated particles pass downward through the column depends on the size and number of those particles. Hence, the size of the pellet of red blood cells at the bottom of the microcolumn, and the extent to which the agglutinates penetrate into the gel or glass beads in the microcolumn, are both inversely related to the strength of the reaction between the reagent and the red blood cells.

With this CAT, after the desired processing steps have been performed, the microcolumn is observed, or read, by a human operator, who then classifies the reaction between the reagent and the red blood cells. Conventionally, the reaction is classified as either negative or positive; and if positive, the reaction is then further classified into one of four classes depending on the strength of the reaction.

Conventional blood analysis systems include a multitude of stations or assemblies, each of which performs one or more functions, and typically a significant amount of operator supervision and labor is needed to operate the systems. For instance, an operator may be needed to move the test samples into an initial position in the system, or from place to place, or station to station, in the system. Also, significant operator time, care and skill may be required to insure that each station operates properly, and to analyze, or read, the results of each reaction.

SUMMARY OF THE INVENTION

An object of this invention is to improve systems and methods for analyzing aqueous solutions.

Another object of the present invention is to provide a fully automated system and method for analyzing blood samples.

A further object of this invention is to move a blood test sample automatically through each of a multitude of stations of a blood analysis system, and at each of those stations, to perform automatically one or more operations on the test sample.

Still another object of the present invention is to provide an incubation station particularly well suited for use in a fully automated blood analysis system.

Another object of this invention is to form openings automatically in test cassettes held in an incubation station of an automated blood analysis system.

A further object of this invention is to provide a station for holding sample solutions and reagents, and that may be effectively used in an automated blood analysis system.

Another object of the present invention is to hold a container securely in a holding station while a pipette, which was forced through a top cap of the container, is withdrawn from the container.

An object of this invention is to provide a centrifuge that insures that all of a multitude of cassettes, which pivoted outward during centrifuging, pivot back down, after centrifuging, into a standard position.

A further object of this invention is to move cassettes to an optical reader station of a blood analysis system, to analyze those cassettes optically in the reader station, and then to remove the cassettes from the reader station, without requiring any operator intervention.

Still another object of the present invention is to store a multitude of cassettes in a drawer assembly and to move those cassettes therein so that selected cassettes are at a discharge position at predetermined times.

These and other objectives are obtained with a blood analysis system or instrument, generally, including an incubator station, a sample and reagent holding station, a pipette assembly, a centrifuge, an analysis station, and a transport assembly, and preferably the analysis system further includes a drawer assembly and control means.

Generally, the incubation station is provided for holding containers while reagents and fluids are being dispensed in those containers, and, if desired, for incubating the containers. The sample and reagent holding station is provided for holding samples and a plurality of reagents, and the pipette assembly is provided for transferring fluids from that sample and reagent holding station to containers in the incubation station. The centrifuge is provided for centrifuging the container, and the analysis station is provided to analyze the containers optically to identify reactions therein. The transport assembly is provided to carry the containers between the incubator station, the centrifuge, and the analysis station. The drawer assembly is provided for holding a supply of containers, and preferably a supply of each of a multitude of types of containers are held in the drawer assembly. With this preferred embodiment, the transport assembly also carries the containers from the drawer assembly to the incubator station.

The control means is connected to the pipette assembly and to the transport assembly. The control means operates the pipette assembly to draw fluids and preselected reagents from the sample and reagent holding station, and to dispense fluids into the containers held in the incubation station to produce predetermined solutions therein. Also, the control means operates the transport subassembly to carry containers from the drawer assembly to the incubator station, to carry containers from the incubator station to the centrifuge after the predetermined solutions have been produced in the containers, and then to carry the containers from the centrifuge to the analysis station.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 13 is a cross-sectional view of the sample and reagent station.

FIG. 14 is a side view of a hold down assembly of the sample and reagent holding station.

FIG. 15 is a front view of the hold down assembly.

FIG. 16 is a top view of the hold down assembly.

FIG. 17 shows the pipette assembly of the blood analysis instrument illustrate in FIGS. 1–4.

FIG. 18 is a side view of the pipette assembly.

FIG. 19 illustrates the pipette of the pipette assembly.

FIG. 36 is a top view of a slide tray that is held in the drawer of FIGS. 33–35.

FIG. 37 is a side view of the slide tray.

FIG. 38 is an end view of the slide tray.

FIG. 39 shows a cassette sensor bar of the drawer subassembly.

FIGS. 41 and 42 show a main work procedure for the blood analysis instrument.

FIGS. 43 and 44 show a continue operation work procedure for the blood analysis instrument.

FIG. 45 shows a cassette waste procedure for the blood analysis instrument.

FIGS. 46–48 illustrate a cassette storage procedure for the blood analysis instrument.

FIGS. 55 . 59 illustrate a batch processing procedure for the blood analysis instrument.

DETAILED DESCRIPTION OF THE PREFERRED EMBODIMENTS

Figure 1:
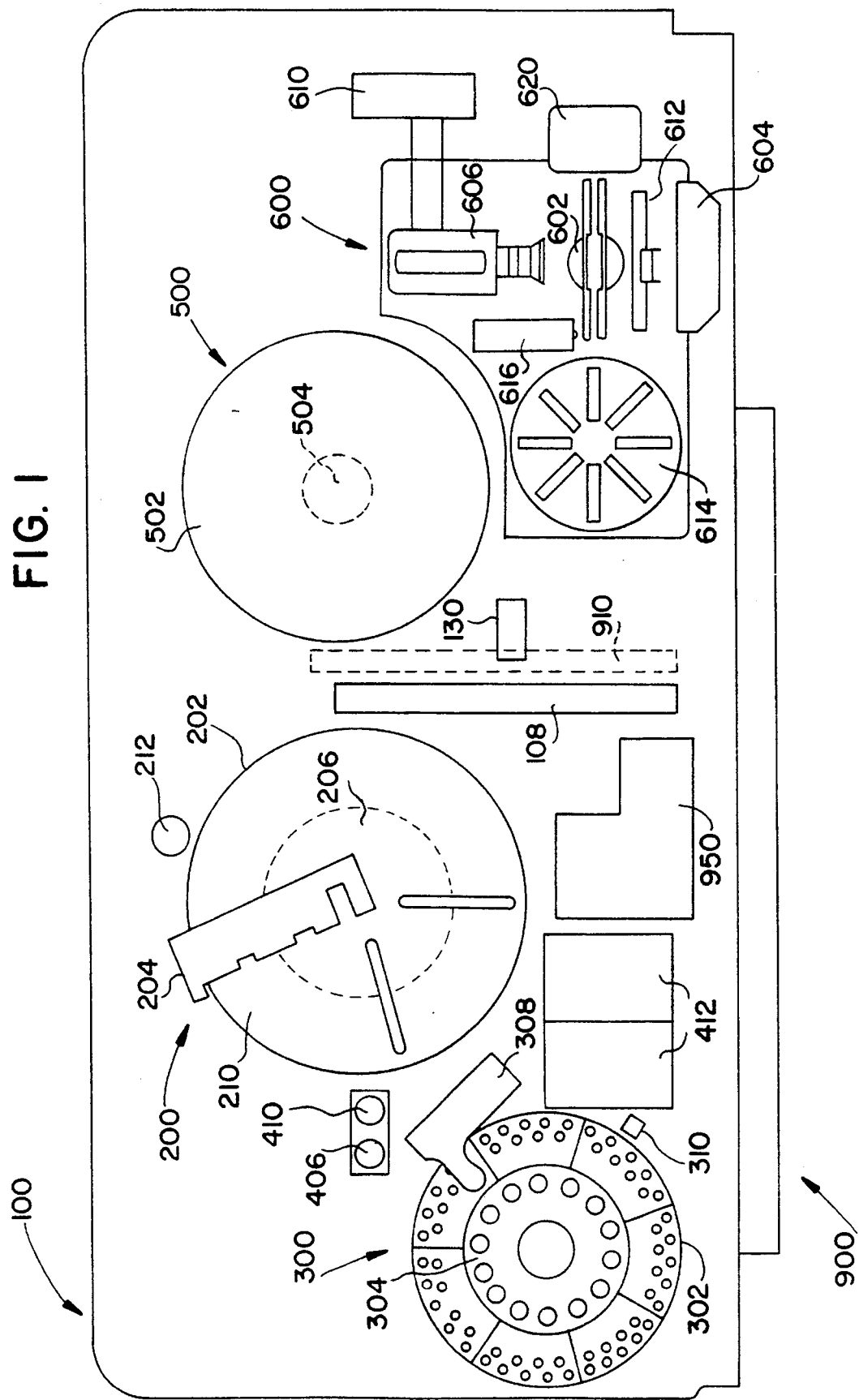
FIG. 1 is a simplified top plan view of a blood analysis instrument embodying the present invention.
Figure 2:
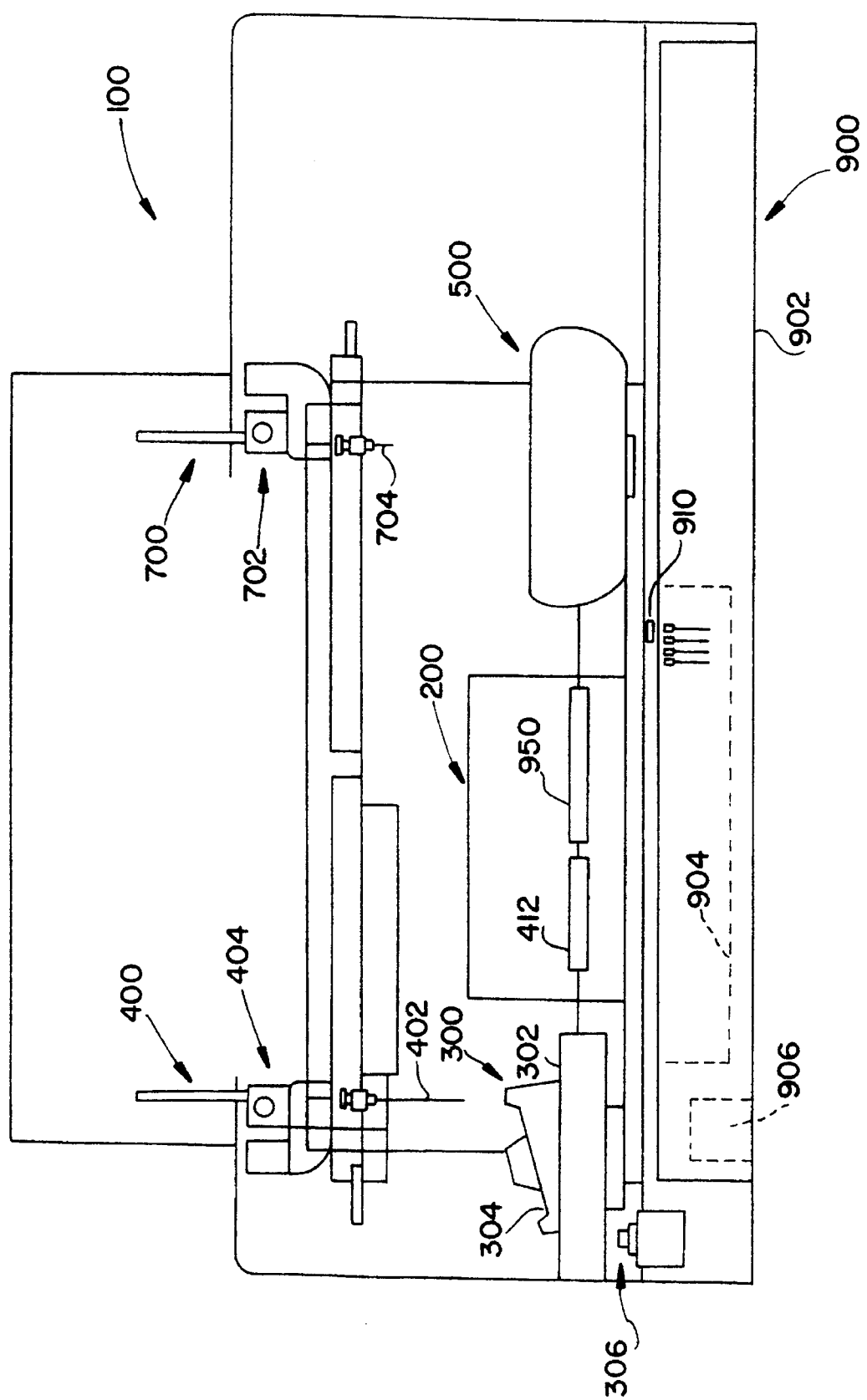
FIG. 2 is a simplified front view of the blood analysis instrument.
Figure 3:
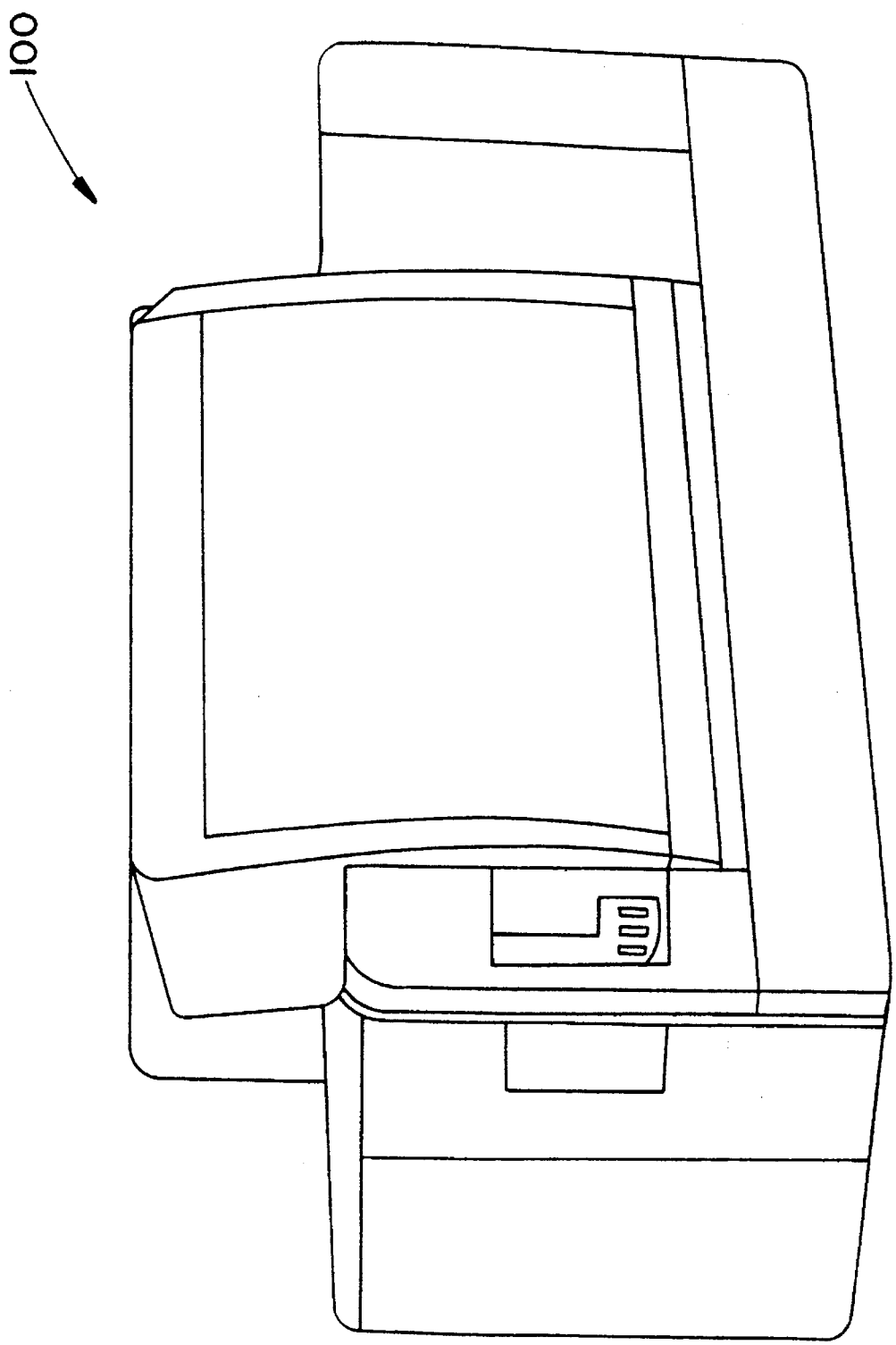
FIG. 3 is a perspective view of the blood analysis instrument.
Figure 4:
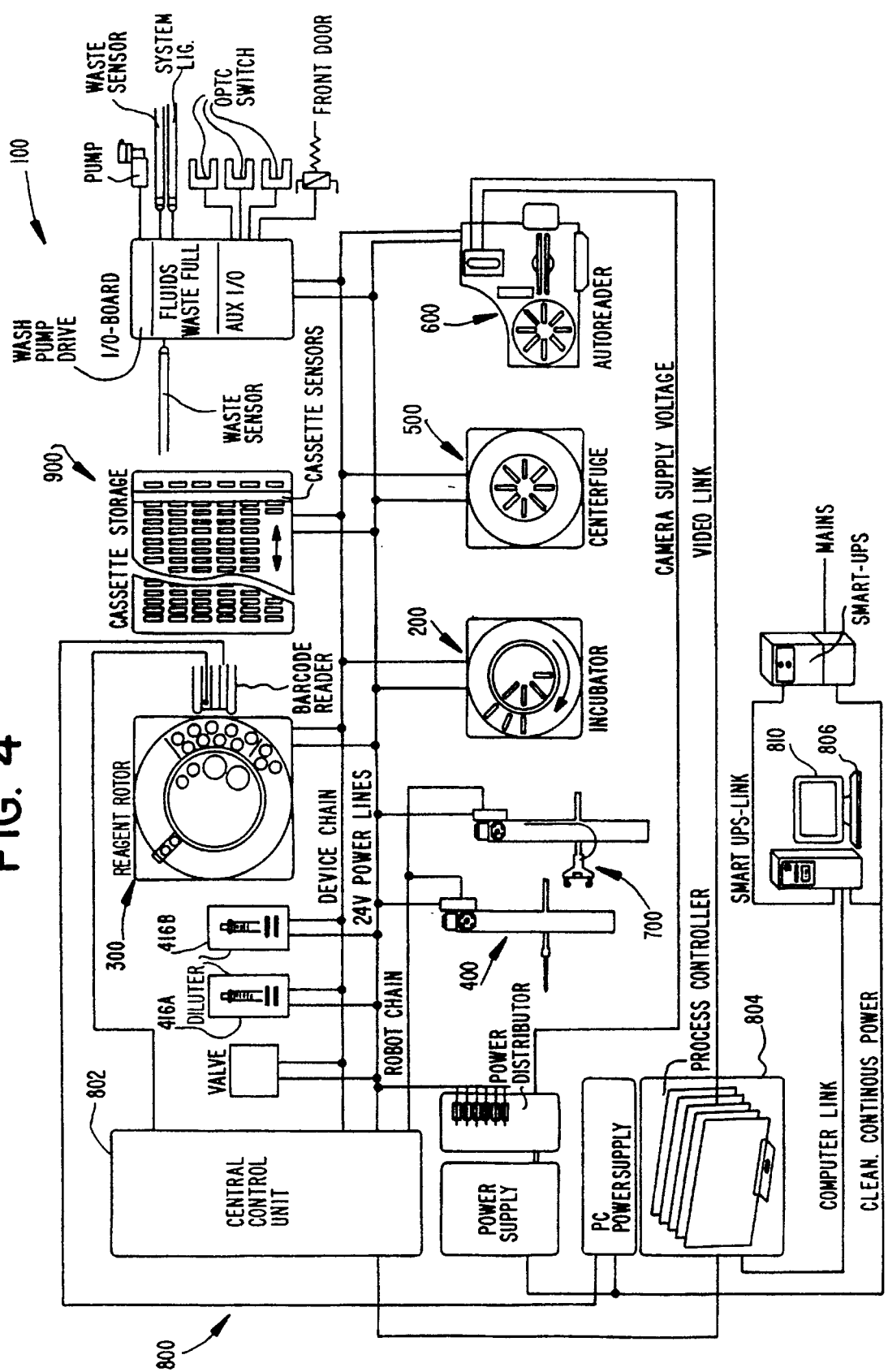
FIG. 4 is a schematic block diagram of the blood analysis instrument.

With reference to FIGS. 1–4, blood analysis system or instrument 100 generally includes incubator station 200, reagent and sample holding station 300, pipette assembly 400, centrifuge 500, analysis station 600, and transport assembly 700; and preferably system 100 further includes control means 800, drawer assembly 900, and a special holding area 950. With the preferred embodiment of system 100 shown in FIGS. 1–4, incubator station 200 includes cassette rack 202 and piercing assembly 204; and the cassette rack 202 includes first and second sections 206 and 210, and motor 212. Sample and reagent station 300 includes sample rack 302, reagent rack 304, drive means 306, tube hold down assembly 308 and bar code reader 310. Pipette assembly 400 includes pipette 402 and robot arm 404, and preferably this assembly also includes shallow and deep wash areas 406 and 410 and a pair of cell dilution racks 412. Centrifuge 500 includes rotor 502 and motor 504. Analysis station 600 includes holding means 602, illumination means 604, imaging subsystem 606, processing subsystem 610, transport subsystem 612, storage rack 614, bar code reader 616, and waste receptacle 620. Transport assembly 700 includes robot arm 702 and gripper 704; control means 800 includes central control unit 802, processor 804, keyboard 806, and keyboard terminal 810; and drawer assembly 900 includes drawer 902, slide tray 904, motor 96 and sensor bar 910.

Incubation station 200 is provided for holding containers or receptacles while reagents and fluids are being dispensed in those containers, and, if desired, for incubating the containers. Station 300 is provided for holding blood samples and a plurality of reagents, and pipette assembly 400 is provided for transferring fluids from station 300 to the containers in incubation station 200. Centrifuge 500 is provided for centrifuging the containers, and analysis station is provided to analyze the containers to identify reactions therein. Transport assembly is provided to carry the containers between incubator station 200, centrifuge 500, and analysis station 600. Drawer assembly 900 is provided for holding a supply of the containers that are used in instrument 100, and preferably assembly 900 holds a supply of each of a multitude of types of containers that are used in instrument 100.

Control means 800 is connected to pipette assembly 400 and to transport assembly 700. The control means operates the pipette assembly to draw blood and reagents from station 300, and to dispense blood and reagents into containers held in incubation station 200 to produce predetermined solutions therein. The control means also operates transport assembly 700 to carry containers from drawer assembly 900 to the incubator station, to carry containers from the incubator station to centrifuge 500 after the predetermined solutions have been produced in the containers and then to carry the containers from the centrifuge to analysis station 600.

The preferred embodiment of system 100 described herein in detail is particularly well suited for analyzing blood samples, and these samples are often referred to as solutions. It should be noted that the present invention may be embodied in systems that analyze other materials, including other aqueous solutions such as urine. It is not necessary, though, that the material being analyzed be a liquid or a fluid; and, thus, the term "solution" as used herein is used in the general sense as any mixture of liquid, gaseous, or solid substances.

Figure 5:
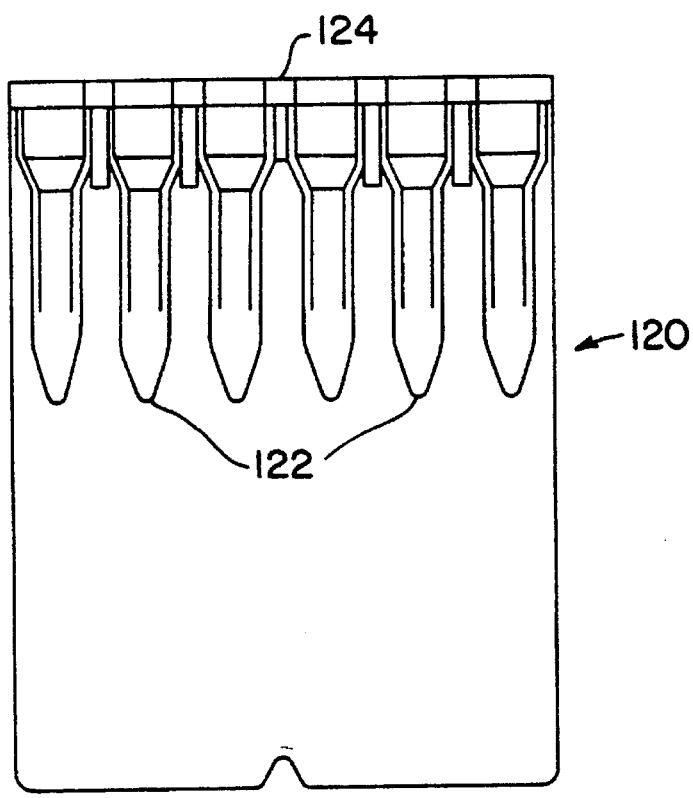
FIG. 5 is a front view of a cassette that may be used in the instrument of FIGS. 1–4.
Figure 6:
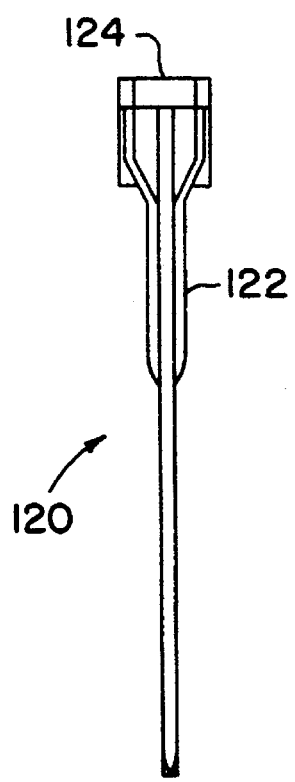
FIG. 6 is a side view of the cassette of FIG. 5.
Figure 7:
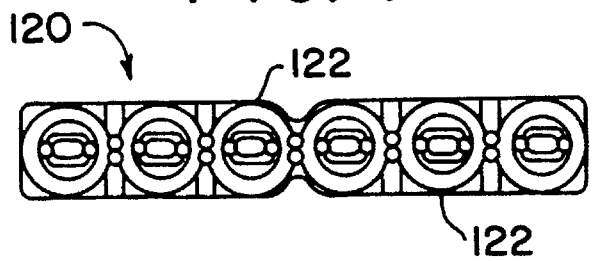
FIG. 7 is a top view of the cassette.

In addition, a large variety of types and sizes of containers may be used in the practice of the present invention; however, the preferred embodiment of system 100 described herein in detail is particularly well suited for use with containers of the type shown at 120 in FIGS. 5, 6, and 7. These containers, referred to as cassettes, are made from a transparent, integrally molded plastic material. A multitude of cavities or wells 122, referred to as columns or microcolumns, are formed in the cassettes and extend downward from the top edge of the cassette, and, for example, the cassette shown in FIGS. 5–7 contains six such microcolumns.

A multitude of very small, transparent glass beads, having diameters on the order of magnitude of 10 to 100 micrometers, are deposited in and form a filter in the lower portion of each microcolumn. Alternately, the lower portion of each microcolumn may be provided with a suitable gel that functions in the same general way as the microbeads. Reagents may be pre-dispensed in the columns of the cassette; and after the columns of the cassette are provided with the desired materials, a foil 124 is typically secured on the top edge of the cassette to cover and close the tops of columns 122.

Preferably, each cassette 120 is provided with a bar code identifying various data about the cassette, and bar code reader 130 is provided to read the bar code on each cassette and to transmit the data thereon to processor 804. For example, the bar code on the cassette may identify the cassette type, the date of manufacture of the cassette, and a recommended expiration date for the cassette. The bar code may include other data that identify the cassette manufacturer as well as the time and place of manufacture. As shown in FIG. 1, the code reader, which may be a standard bar code reader, is preferably located so that the reader scans the bar code on each cassette immediately after the cassette is withdrawn from drawer assembly 900.

With reference again to FIGS. 1–4, in the operation of instrument 100, a cassette 120 is moved in drawer assembly 900 to a position where gripper 704 of transport assembly 700 has access to the cassette, and then the gripper picks up the cassette and moves the cassette in front of bar code reader 130. The bar code reader verifies, for example, that the cassette is properly oriented, that the proper cassette has been removed from the drawer assembly, and that the expiration date for the cassette has not been reached. Also, the bar code reader may read a unique sequence number on the cassette, and this number may be used to identify and to keep track of the cassette during its movement through instrument 100.

If the checks made by the bar code reader show that the cassette is acceptable, then the gripper places the cassette into incubator rack 202, and the incubator positions the cassette beneath piercing assembly 204. That assembly 204 operates to pierce openings in the top of the cassette, and then the incubator moves the cassette to a position where pipette 402 is able to dispense fluids into the cassette. The pipette is then operated to draw fluids from reagent and sample racks 302 and 304 and to deposit the appropriate reagents and samples into the cassettes. After this, the cassette may be incubated, and the cassette is carried by gripper 704 to centrifuge 500 and deposited therein. If necessary, a balance cassette may also be placed in the centrifuge by the gripper. The centrifuge then spins the cassette, first for two minutes at 55 g and then for three minutes at 199 g.

At the end of the spin, gripper 704 removes the cassette from centrifuge 500 and places the cassette in storage rack 612 of analysis station 600, and this storage rack then positions the cassette immediately adjacent the cassette holder 602. Transport subassembly transfers the cassette from rack 612 to holder 602, and an image of the cassette, or pertinent portions thereof, is produced on imaging subsystem 606. A digitized image of the cassette, or the pertinent portions thereof, is obtained, and the digitized data is processed to determine if a reaction occurred in the cassette and, if so, to classify the reaction. If analysis station 600 can adequately grade the reaction, then the cassette is moved into waste receptacle 614. However, if the cassette reaction is not readable, then the cassette is placed into holding area 950, to be read by the user.

A multitude of tests may be simultaneously performed on instrument 100. For these tests, the user transmits data to process controller 804 identifying the type of test or tests to be performed on each of one or more blood samples; and the process controller then determines the type and number of cassettes needed to perform these tests and the type and amount of reagents that need to be dispensed into each cassette in order to perform the requested tests. Further, preferably, process controller 804 controls the operation of transport assembly 700 to move the necessary cassettes in and around instrument 100 in the desired manner, and to expedite completion of all of the test being performed by the instrument. With instrument 100, after the user places the blood samples in the instrument and identifies the test or tests to be performed on each sample, the user is not needed to supervise or monitor any further operation of the instrument. At the same time, instrument 100 allows the user to place additional blood samples in the instrument and to request additional tests even while the instrument is performing other tests.

Figure 8:
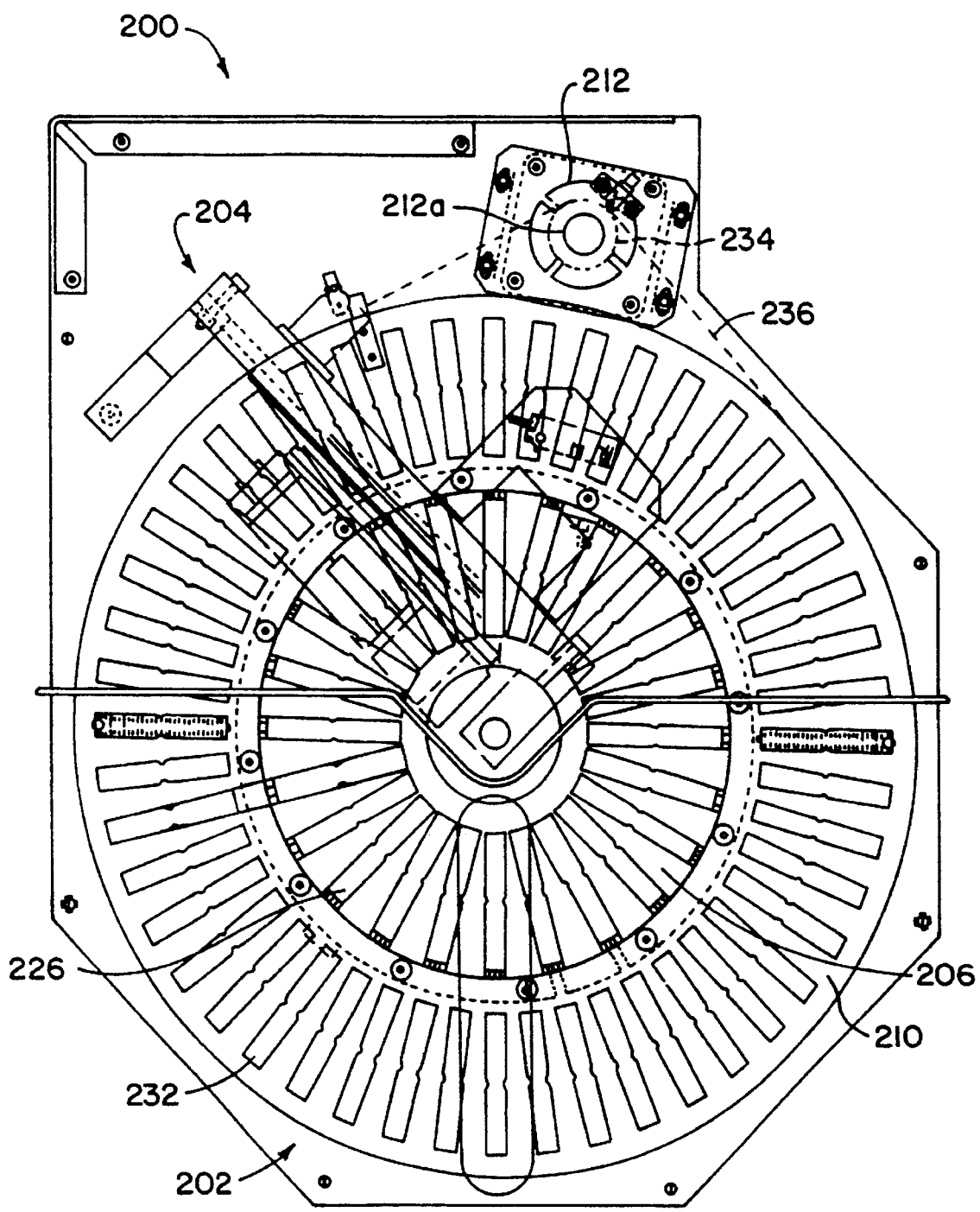
FIG. 8 is a more detailed, top view of the incubation station of the instrument shown in FIGS. 1–4.
Figure 9:
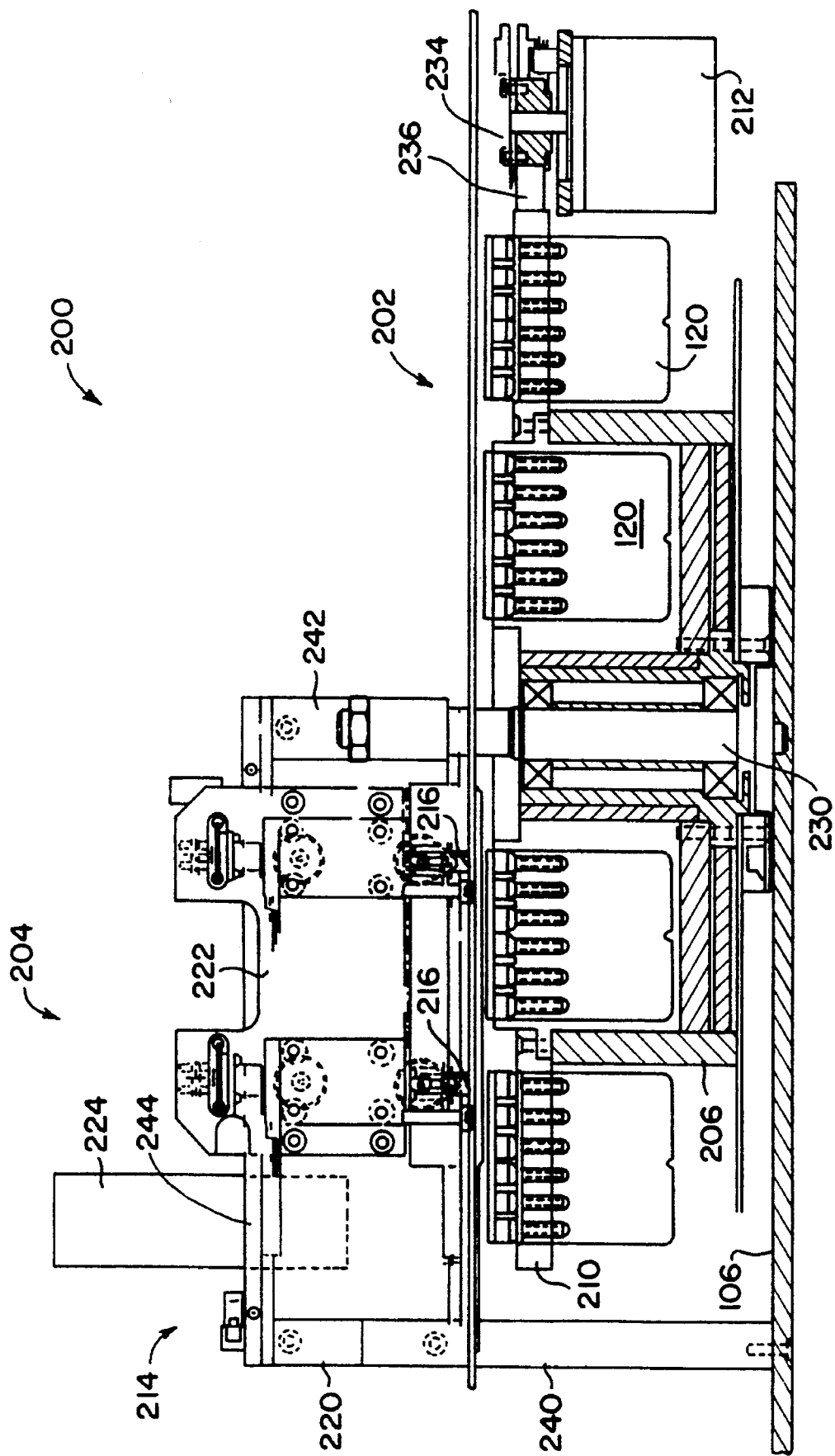
FIG. 9 is a cross-sectional view of the incubation station.

FIGS. 8 and 9 illustrate incubator station 200 in greater detail; and, as previously mentioned, this station generally includes cassette rack sections 206 and 210, piercing assembly 204 and motor 212. Moreover, preferably, rack sections 206 and 210 include first and second rotatable, concentric carousels or rings. In addition, piercing assembly 204 preferably includes support subassembly 214 and piercing needles 216; and subassembly 214 includes frame 220, slide bracket 222, and motor means 224.

Rack 202 is provided for holding a multitude of cassettes 120. The first section 206 of rack 202 is comprised of a substantially solid body made, for example, from aluminum, and forming a multitude of radial recesses 226 for receiving cassettes 120; and preferably, this section of rack 202 includes means to heat or incubate the cassettes placed therein. Rack section 206 has the general shape of a cylinder and is rotatably mounted on a central vertical shaft 230.

Second rack section 210 also forms a multitude of recesses 232 for receiving cassettes 120, and preferably rack sections 206 and 210 are connected together for unitary movement. With the embodiment of incubating station 200 shown in FIGS. 8 and 9, rack section 210 includes a generally flat annulus or ring connected to and radially extending outward from first rack section 206. Rack section 210 is concentric with rack section 206, and the two rack sections rotate together about the axis of shaft 230. Also, recesses 226 are uniformly spaced around rack 206, and recesses 232 are uniformly spaced around rack 210. As shown in FIG. 8, rack 210 contains twice the number of recesses as rack 206, and the recesses 226 and 232 are positioned so that every other recess 232 of rack 210 is radially aligned with a respective one of the recesses 226 of rack 206. Preferably, the upper surfaces of recesses 226 and 232 are shaped and sized so that these upper surfaces engage the side surfaces of cassettes 120 and hold the cassettes in place in the rack sections, as shown in FIG. 9.

Motor 212 is provided to rotate racks 206 and 210 about shaft 230. More specifically, motor 212 includes rotatable motor shaft 212a, and pulley 234 is mounted on that motor shaft for rotation therewith. Belt 236 is mounted on pulley 234 and extends around the outer circumferential edge of rack 210. Rotation of motor shaft 212a rotates pulley 234, and this pulls belt 236 around pulley 234 and the outside edge of rack section 210, rotating rack sections 206 and 210 about the axis of shaft 230.

Figure 10:
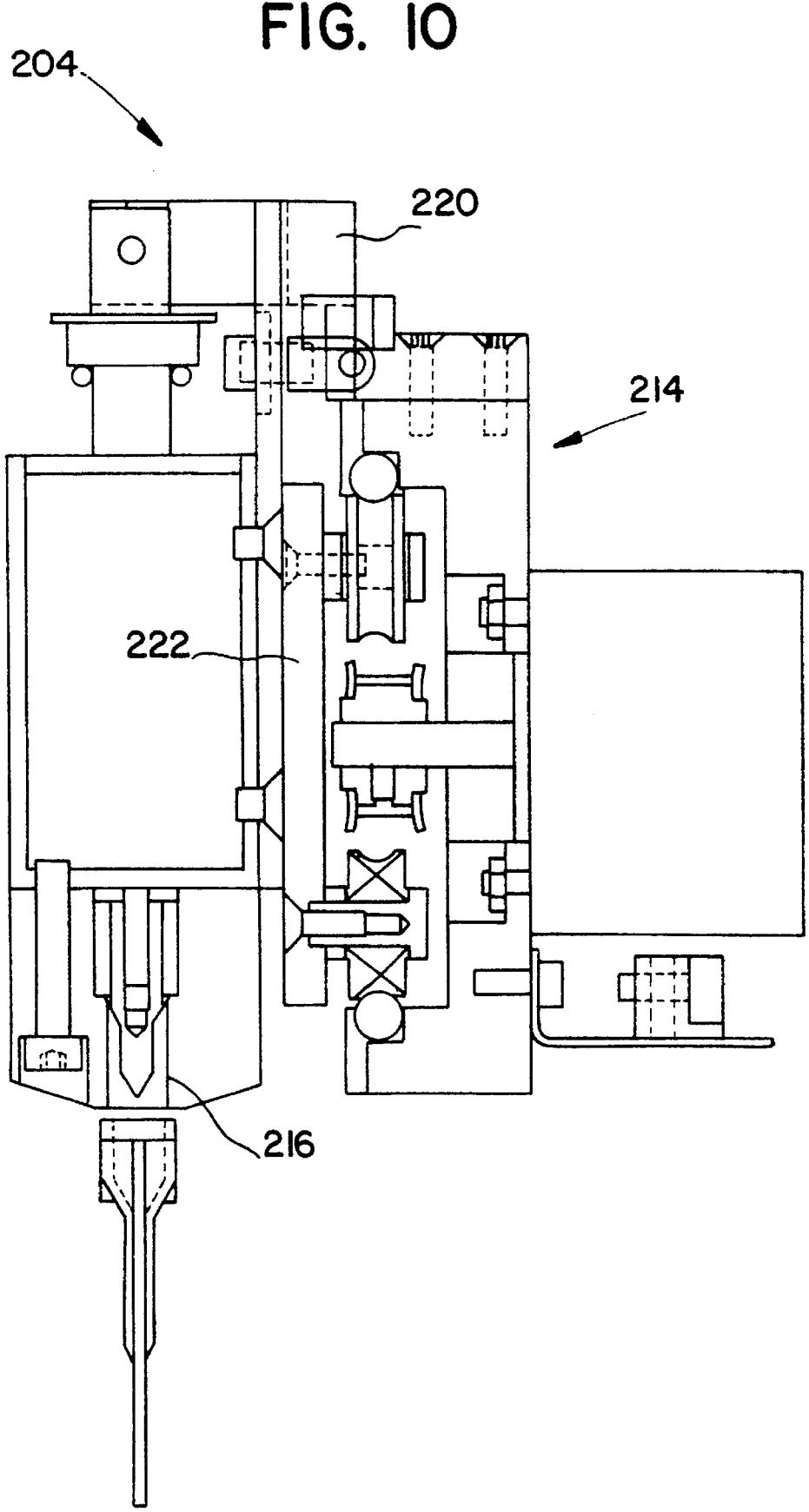
FIG. 10 is a side view of a piercing assembly of the incubation station.

Piercing assembly 204 is provided to pierce the top covers 124 of cassettes 120. With particular reference to FIGS. 9 and 10, support subassembly 214 of the piercing assembly extends over rack sections 206 and 210, and piercing needles 216 are mounted on subassembly 214 for upward and downward reciprocating movement. Means, such as electric solenoids, are connected to those needles to reciprocate the needles and, thereby, to pierce the covers of cassettes 120 held in racks 206 and 210.

More specifically, frame 220 of subassembly 214 includes outer, inner, and lateral support members 240, 242, and 244. Outer member 240 is secured to and extends upward from a panel 106 of instrument 100, and inner support member 242 is supported by and extends upward from shaft 230. Lateral support member 246 is connected to and extends between support members 242 and 244, and this lateral support member extends over racks 206 and 210 and recesses 226 and 230 thereof. Slide bracket 222 is mounted on lateral support member 244 for sliding movement therealong, over racks 206 and 210. Motor 224 is mounted on lateral support member 244 and is connected to slide bracket 222 to slide that bracket along support member 244. Needles 216 are mounted on slide bracket 222 for movement therewith across racks 206 and 210; and in particular, each needle is adapted to move across a respective one of the racks. Needles 216 are also mounted on bracket 222 for the abovementioned upward and downward movement of the needles.

In the operation of incubation station 200, cassettes 120 are placed in rack section 206 or rack section 210 depending, respectively, on whether the cassettes are or are not to be incubated. After the desired number of cassettes have been placed in racks 206 and 210, the racks are rotated to align the cassettes below piercing assembly 204, and in particular, below the piercing needles 216. When a given cassette is positioned below one of the needles 216, that needle is moved over the cassette to position the needle directly above each column 122 of the cassette that is to be opened; and when the needle is directly above such a column, the needle is reciprocated to pierce the cassette cover 124 over that column and, thereby, to form a top opening into that column.

Figure 11:
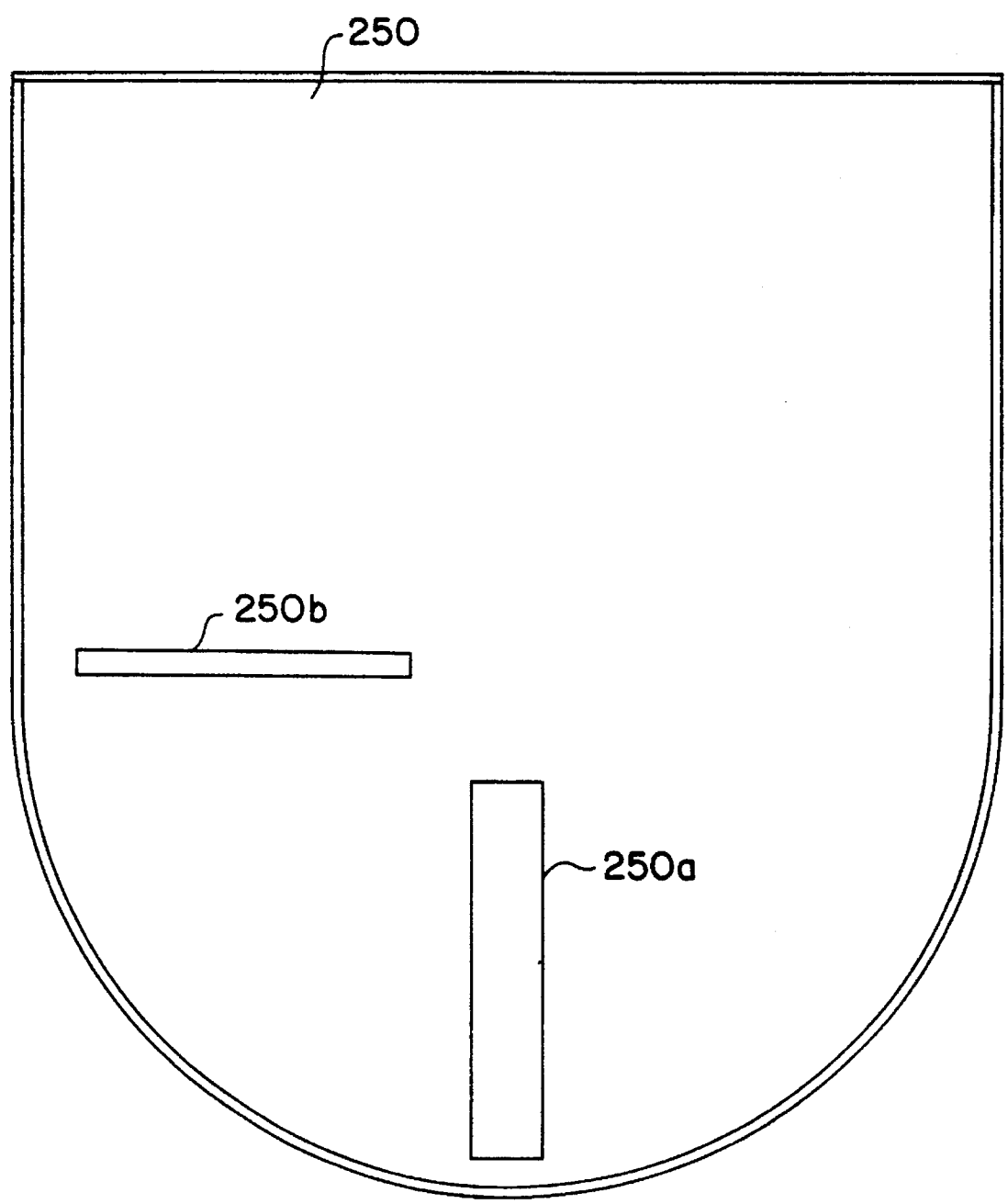
FIG. 11 shows the cover for the incubation station.

Preferably, a top cover 250, shown in FIG. 11, is provided for rack 202, and this cover forms two openings 250a and 250b, each of which radially extends across both the circle formed by recesses 226 and the circle formed by recesses 232. First opening 250a is large enough to allow gripper 704 of transport assembly 700 to place cassettes 120 into and remove cassettes from rack 202 through this opening 250a, and a cassette held directly below this opening is said to be in the gripper access position. Second opening 250b is large enough to allow pipette 402 to dispense blood samples and reagents into the columns 122 of cassettes 120 located directly below this opening, and a cassette held directly below this opening 250b is said to be in the solution receiving position.

When it is desired to place a cassette in one of the recesses of rack 202, that recess is moved beneath the access opening 250a, and the transport assembly 700 then drops a cassette into that recess. Subsequently, this cassette is moved beneath piercing assembly 204, and the cassette cover 124 is pierced at the appropriate locations to form openings in the desired columns of the cassette. Then, the cassette is moved beneath opening 50b, and selected blood samples and reagents are dispensed into selected columns of the cassette. After this, the cassette may be incubated, and then the cassette is moved back beneath access opening 250a, where the cassette can be gripped and removed from rack 202 by the transport assembly.

Figure 12:
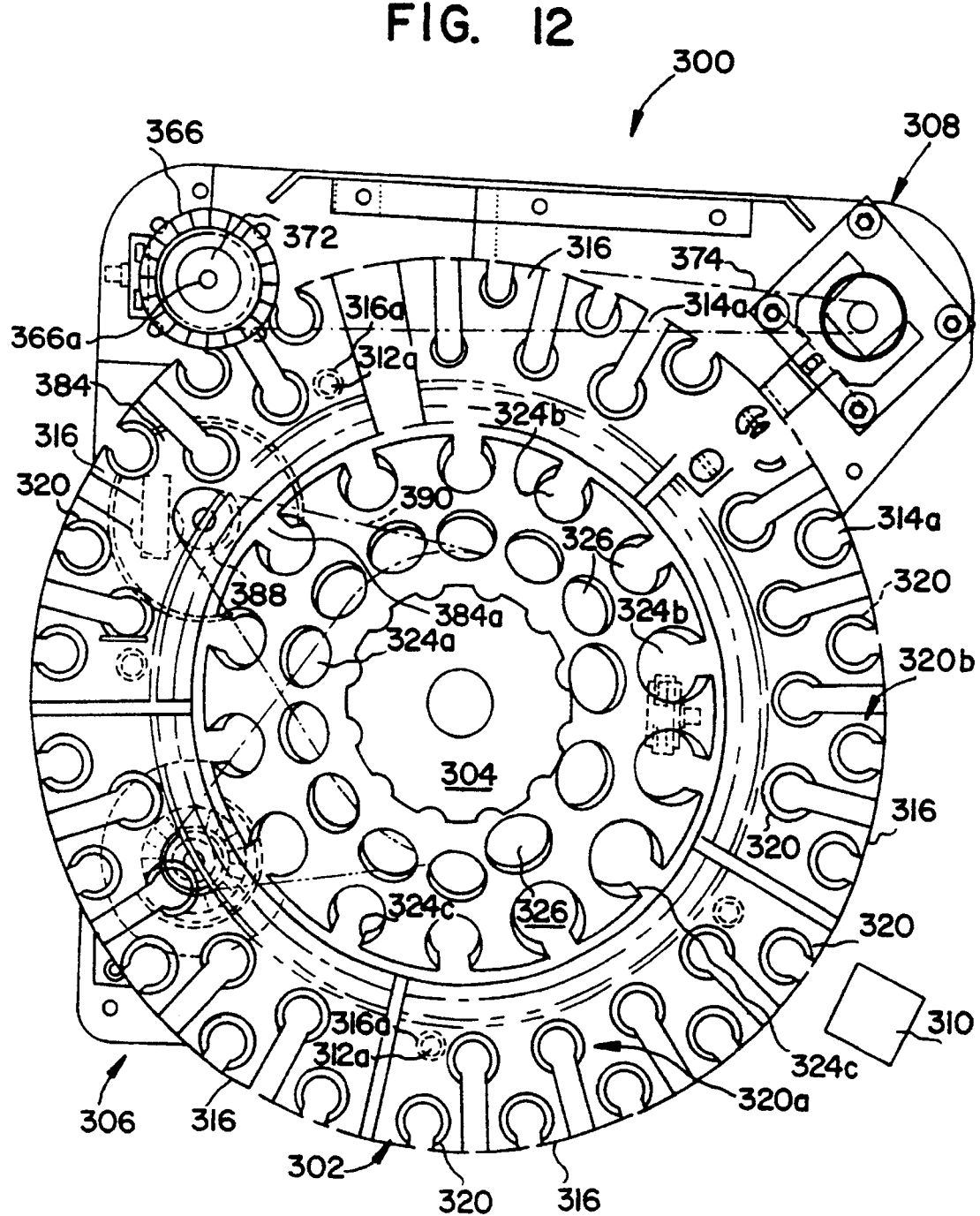
FIG. 12 is a top view illustrating the sample and reagent holding station of the analysis instrument of FIGS. 1–4.

With reference to FIGS. 12 and 13, fluid station 300, generally, comprises sample rack 302, reagent rack 304, and drive means 306, and preferably the station further includes tube hold down assembly 308 and bar code reader 310. More specifically, sample rack 302 includes bottom plate 312 and body 314, and the body includes a multitude of separate segments 316, each of which forms a multitude of container receptacles 320. Reagent rack 304 includes bottom plate 322 and body 324, and this body forms a multitude of container receptacles 326. Drive means 306 includes support shaft 330, drive shaft 332, pulleys 334 and 336, collars 340 and 342, motor means 344, and transmission means 346. Preferably, the motor means is a stepper motor, and transmission means 346 includes pulley 350 and belt 352. Tube hold down assembly 312 includes support subassembly 354, arm 356, and connecting means 360, and preferably this support subassembly includes frame 362 and shaft 364. In addition, as shown in FIG. 12, assembly 308 further includes means to pivot shaft 364 and arm 356, and this pivot means includes motor 366, pulleys 370 and 372, and belt 374. Fluid station 300 is described in detail in copending application No. , for "Apparatus for Holding Containers of Solutions," filed herewith, the disclosure of which is herein incorporated by reference.

Rack 302 is provided for holding a multitude of containers or tubes of blood samples, and preferably these blood sample containers have the general shape of conventional test tubes, as shown at 376. More specifically, bottom plate 312 has a generally flat annular or ring shape, and rack body 314 is supported by and extends upward from bottom plate 312. Each of the segments 316 of rack body 314 has an arcuate shape, including generally planar top and bottom surfaces and generally vertical arcuate outside and inside surfaces. The segments 316, when placed on plate 312, form a generally continuous ring circumferentially extending around the outer portion or perimeter of the plate.

Preferably, each of the segments 316 of rack body 314 is releasably mounted on plate 312, and each rack segment can be removed from and placed in rack 302 independent of the other rack segments. To help hold the rack segments 316 in place in rack 302, preferably the bottom surface of each segment 316 forms one or more recesses on sockets, for example as shown at 316a, that are mounted on mating protrusions, for example as shown at 312a, that extend upward from plate 312.

In addition, each ring segment 316 has a substantially solid shape and forms a multitude of openings that form receptacles 320. Each opening 320 has a generally cylindrical shape, axially extending completely through the ring segment, to bottom plate 312. The openings 320 are arranged in two concentric circles, an inner circle 320a and an outer circle 320b. The openings in each circle are uniformly spaced around that circle; and the openings are positioned so that, in the circumferential direction, the openings in the inner circle 320a are disposed between the openings 320b in the outer circle. Short or long radial passages 314a extend radially outward from each opening 320, to the outer surfaces of the base segments, allowing or facilitating visual observation of fluids in the containers held in those openings 320. Spring clips 378 may be secured in openings 320 to help hold containers 376 securely therein.

Rack 304 is provided for holding a multitude of containers or vials of reagents, and preferably these containers have the shape of small jars. More specifically, bottom plate 322 is mounted on and extends outward from drive means 306, specifically support collar 340. Plate 322 has a generally flat, annular or ring shape; however, the outer portion of the top surface of bottom plate 322 tapers outwardly downwardly. Body 324 is mounted on and extends upward from plate 322, and body 324 forms a bottom central recess that is shaped and positioned to receive collar 342. Body 324 also forms first and second sets of openings 324a and 324b that form the receptacles 326. Openings 324a are relatively shallow and extend inward from the top surface of body 324, and openings 324b are deeper and preferably extend completely through body 324, to bottom plate 312.

Openings 324a and 324b are arranged on first and second concentric circles, respectively, with the former circle radially located inside the latter circle. The openings in each circle are uniformly spaced around that circle, and each opening 324a is radially aligned with a respective one of the openings 324b. Short radial passages 324c extend radially from openings 324b to the outside surface of body 324, allowing or facilitating visual observation of the fluids in the containers held in those openings. Further, spring clips 378 may also be secured in openings 324b to help secure containers therein.

Preferably, the reagent and sample containers held in station 300 have bar codes to identify the container to provide other data that may be desired. Bar code reader 310 is located adjacent to the sample and reagent racks 302 and 304 to read the bar codes on the reagent and sample containers. An annular plate 380 having a continuous bar code may be mounted on rack 302, radially inward of the inner circle 320a of openings, and this bar code may be used to identify rack 302. In addition, preferably this bar code is read by reader 310 whenever one of the openings 320 that is empty is moved past the reader, and thus this bar code may be used to indicate that a particular opening 320 does not have a container.

As particularly shown in FIG. 13, body 324 of reagent rack 304 defines an axis 304a that is tilted relative to the axis of support shaft 330 and drive shaft 332; and, as viewed in FIG. 13, the left end of reagent holder 304 is higher than the right end thereof. As reagent holder 304 rotates, that holder rotates about tilt axis 304a; however, the relative position of the left and right ends of the reagent holder, as viewed in FIG. 13, remain the same. Hence, as the reagent holder is rotated, openings 324a and 324b, and any containers held therein, move downward and upward, between the positions of the two openings 324a and the two openings 324b shown in FIG. 13, as well as around axis 304a.

Drive means 306 is provided to rotate holders 302 and 304, and preferably this drive means also supports both of these holders. More specifically, support shaft 330 is secured to and extends upward from instrument panel 106, and drive shaft 332 is rotatably mounted on support shaft 330, coaxial therewith. Pulley 334 is mounted on and connected to drive shaft 332 for unitary rotation therewith about support shaft 330. Also, pulley 336 is rotatably mounted on drive shaft 332 for relative rotation about the drive shaft, and pulley is connected to rack 304, specifically bottom plate 324 thereof, to rotate rack about the axis of support shaft 330. Support collar 340 is mounted around drive shaft 332, and collar 340 is connected to rack 302, specifically bottom plate 312 thereof, for rotation therewith. Drive collar 342 is mounted on support collar 340 for rotation, independent of collar 340; and drive collar 342 is connected to drive shaft 332, via universal joint 382, so that rotation of the drive shaft rotates collar 342. Drive collar 342 is also connected to bottom plate 322 of rack 304 to rotate that rack with the drive shaft 332. Because drive collar 342 is rotatably mounted on support collar 340, rack 304 can rotate around axis 304a even while collars 340 and 302 are stationary.

Motor 344 and transmission means 346 are provided to rotate drive shaft 332 and, thereby, to rotate rack 304. More specifically, motor 344 is securely connected to instrument panel 106, and includes a rotatable motor shaft 344a. Pulley 350 is mounted on shaft 344a for rotation therewith, and belt 352 is drivingly mounted on pulleys 334 and 350 such that rotation of pulley 350 causes this belt to move between and around pulleys 334 and 350. This causes belt 352 to rotates pulley 334, this rotates drive shaft 332, and this causes drive collar 342 and reagent rack 304 to rotate about tilt axis 304a.

Similarly, motor 384 and transmission means 386 are provided to rotate pulley 336 and sample rack 302. More specifically, motor 384 is securely connected to instrument panel 106 and includes a rotatable motor shaft 384a, and pulley 388 is mounted on motor shaft 384a for rotation therewith. Belt 390 is drivingly mounted on pulleys 388 and 336 such that rotation of pulley 388 causes the belt to move around and between pulleys 388 and 336, and the belt rotates pulley 338; and rotation of pulley 336, in turn, rotates rack 302.

Thus, by selectively actuating motors 344 and 388, both racks 302 and 304 may be rotated simultaneously, or either one of the racks may be rotated independent of the other one of the racks.

As discussed previously, in the operation of fluid station 300, a pipette or similar instrument is lowered into the sample containers held in sample rack 302, fluids are drawn into the pipette and then the pipette is withdrawn upward from the sample container and used to carry the fluids to another location. The tops of the sample containers are often covered with a protective cap or rubber stopper; and as the pipette is lowered into a container, the pipette pierces through the stopper on the container top. Under these circumstances, when the pipette is withdrawn from the container, the pipette may frictionally engage the container stopper and tend to pull the whole container upward and out of the receptacle in which the container is held. Hold down assembly 308 is provided to insure that the pipette does not pull the containers out of the rack 302 as the pipette itself is pulled out of the container.

With particular reference to FIGS. 14–16, support subassembly 354 of assembly 308 is secured to panel 106 of instrument 100 and arm 356 is connected to that support subassembly 354 and extends therefrom and over sample rack 302; and with the embodiment of assembly 308 shown in the drawings, arm 356 extends over both circles 320a and 320b of openings 320. Arm 356 forms two through openings 356a and 356b located directly above circles 320a and 320b respectively, and openings 356a and 356b are sized so that they are smaller than the tops of the containers held in openings 320a and 320b respectively.

In the operation of station 300, rack 302 is moved so that a selected sample container is moved into a position, referred to as the aspirate position, directly below one of the openings 356a or 356b of arm 356, and then a pipette is lowered through that one opening in arm 356 and into that selected container. Fluid is drawn into the pipette, and then the pipette is drawn upward, out of the container. If the container is pulled upward with the pipette, arm 356 limits upward movement of the container and prevents the container from being pulled out of the opening 320. If the container strikes arm 356, that arm prevents further upward movement of the container, while the pipette can continue to move upward, out of the container, through the arm opening. Once the pipette is completely withdrawn from the container, the container then drops back into its receptacle in the sample rack 302.

Preferably, the height of arm 356 is adjustable, allowing hold down assembly 308 to be used with sample containers of different heights. More specifically, with the preferred embodiment of assembly 308, support subassembly 354 includes frame 362 and a vertical shaft 364, which is supported by that frame. Mounting bracket or collar 360 is slidably mounted on shaft 364, and arm 356 is connected to that bracket for sliding movement therewith along shaft 364. A screw 360a extends through mounting bracket 360 and engages shaft 364 to releasably hold the mounting bracket in place on the shaft. To adjust the height of arm 356, screw 360a is threaded away from shaft 364, allowing bracket 360 to slide therealong. Bracket 360 is slid along shaft 364 to move arm 356 to a new height; and when arm 356 reaches the desired position, screw 360a is threaded into secure engagement with shaft 364, securing bracket 360 and arm 356 in that new position.

In addition to the foregoing, assembly 308 preferably includes means to pivot arm 356 toward and away from sample rack 302, and this pivot means includes motor 366, pulleys 370 and 372, and belt 374. More particularly, shaft 364 extends downward through a central opening 362a in frame 362, and the shaft is rotatably supported by the frame, and pulley 370 is mounted on a lower portion of the shaft for rotation therewith. Motor 366 is mounted on instrument panel 106 and includes a rotatable motor shaft 366a, and pulley 372 is mounted on shaft 366a for rotation therewith. Belt 374 is drivingly mounted on and extends around pulleys 370 and 372 such that rotation of pulley 372 causes the belt to move between and around the two pulleys 370 and 372. The belt 374 rotates pulley 370 around the axis of shaft 364, and this rotates both shaft 364 and arm 356.

With the embodiment of assembly 308 shown in the drawings, arm 356 has a Z-shape, including upper and lower, generally horizontal portions, and a middle vertical portion connected to and extending between those upper and lower portions. Also, frame 362 has a C-shape, including upper and lower horizontal portions and an intermediate portion extending between those upper and lower portions. Preferably, the upper end of shaft 364 extends into and is rotatably guided in an upper opening 362b formed in the upper horizontal portion of frame 362. Supporting the upper end of shaft 364 in this way helps to maintain the desired axial orientation of the shaft during operation of assembly 308.

Pipette assembly is illustrated in FIGS. 17–19; and generally, this assembly includes pipette 402 and robot arm 404. Arm 404 is supported for horizontal sliding movement along a support means, including bar 414; and the pipette 402 is supported both for horizontal sliding movement along, and vertical sliding movement relative to, arm 404. Suitable motors (not shown) are provided to move the robot arm and the pipette in the x-, y-, and z-directions. With particular reference to FIG. 19, pipette 402 is a long, thin, hollow tube, and the pipette has a generally uniform, circular cross-section; however, the bottom or lower portion of the pipette tapers or narrows radially inwardly slightly.

Preferably, a flexible hose (not shown) is mounted on the top end of the pipette 402 and used to connect the pipette to a suitable control, such as diluters 416a and 416b (shown in FIG. 4), which is used to aspirate fluids into and to dispense fluids from the pipette. Any suitable hose and controller may be used with pipette 402. Also, pipette 402 is preferably made of aluminum, and the capacitance of the pipette is monitored or measured; and this measurement is used, as discussed below, to indicate when the pipette contacts a liquid in either the reagent vials or blood sample vials.

Pipette assembly 400 also includes shallow and deep wash areas 406 and 410 and a pair of cell dilution racks 412, shown in FIG. 1. Wash areas 406 and 410 are wells or containers mounted on or recessed in instrument panel 106, and these wells or containers contain liquids for rinsing or cleaning pipette 402. The pipette is cleaned or rinsed by lowering the pipette into the wash areas, and area 406 has a height or depth sufficient to allow the top of the pipette to be immersed in the liquid in that area, while area 410 has a height or depth sufficient to allow the lower portion of the pipette to be immersed in the liquid in this area. Cell dilution racks 412 are conventional racks forming a multitude of small wells or cells. In use, fluids are dispensed into these wells to dilute selected liquids or to produce selected solution mixtures.

Figure 20:
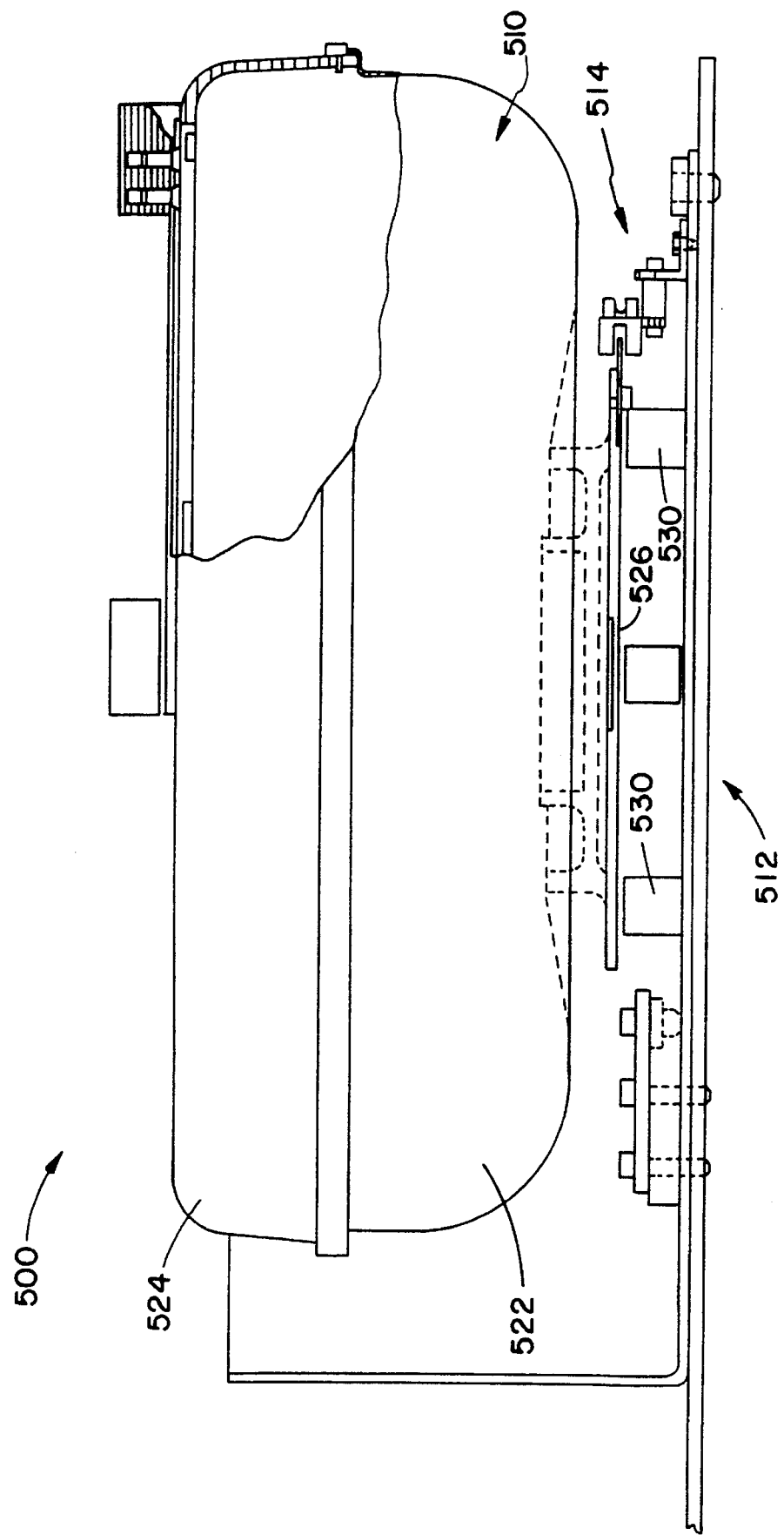
FIG. 20 shows the centrifuge of the blood analysis instrument shown in FIGS. 1–4.
Figure 21:
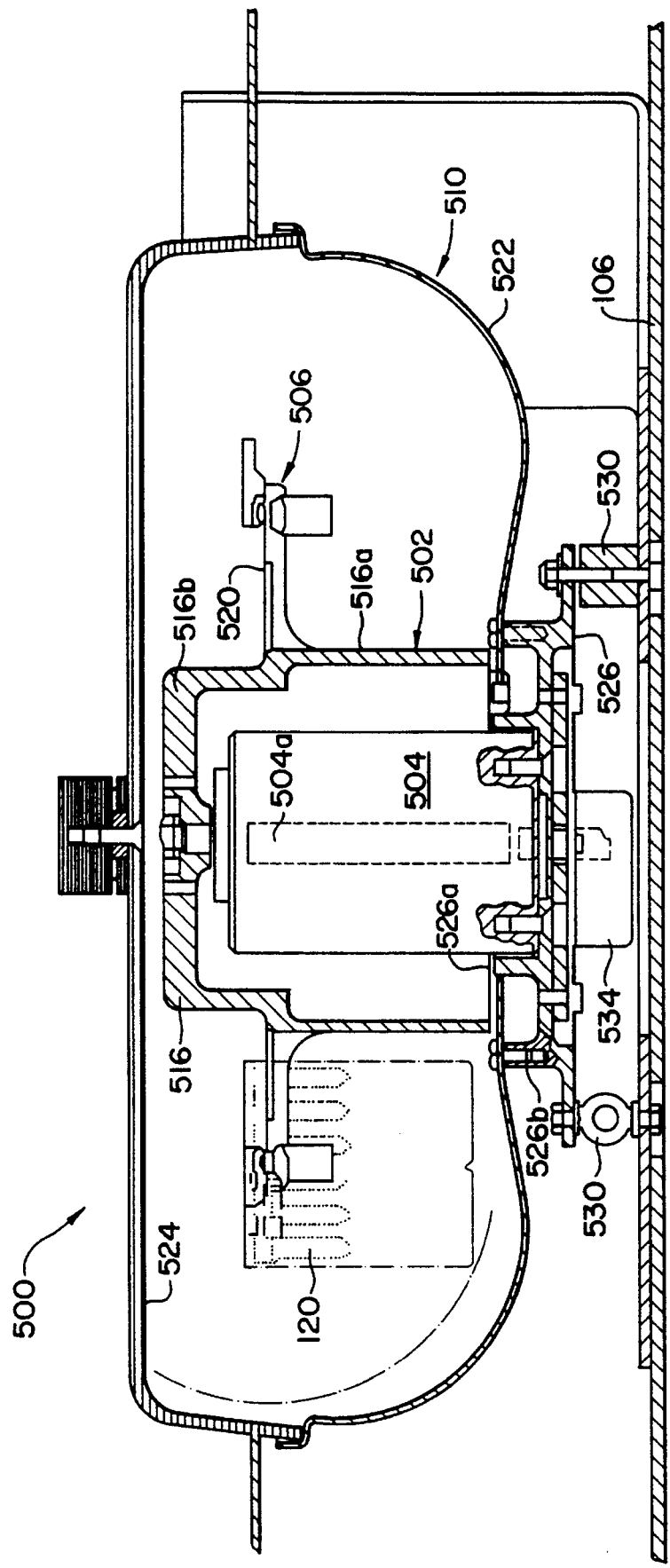
FIG. 21 is a cross-sectional view of the centrifuge.
Figure 22:
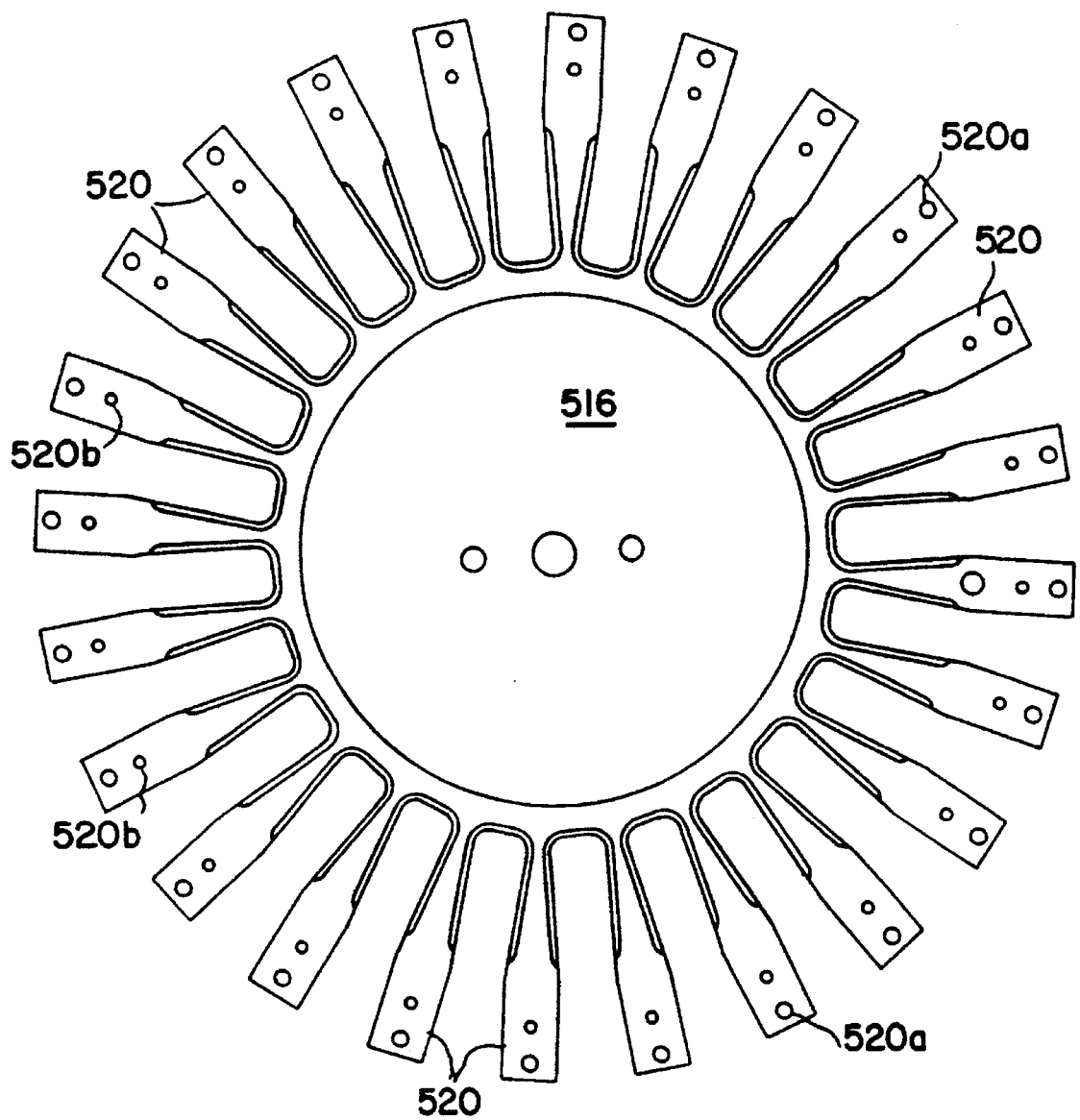
FIG. 22 is a top view of the rotor of the centrifuge.
Figure 23:
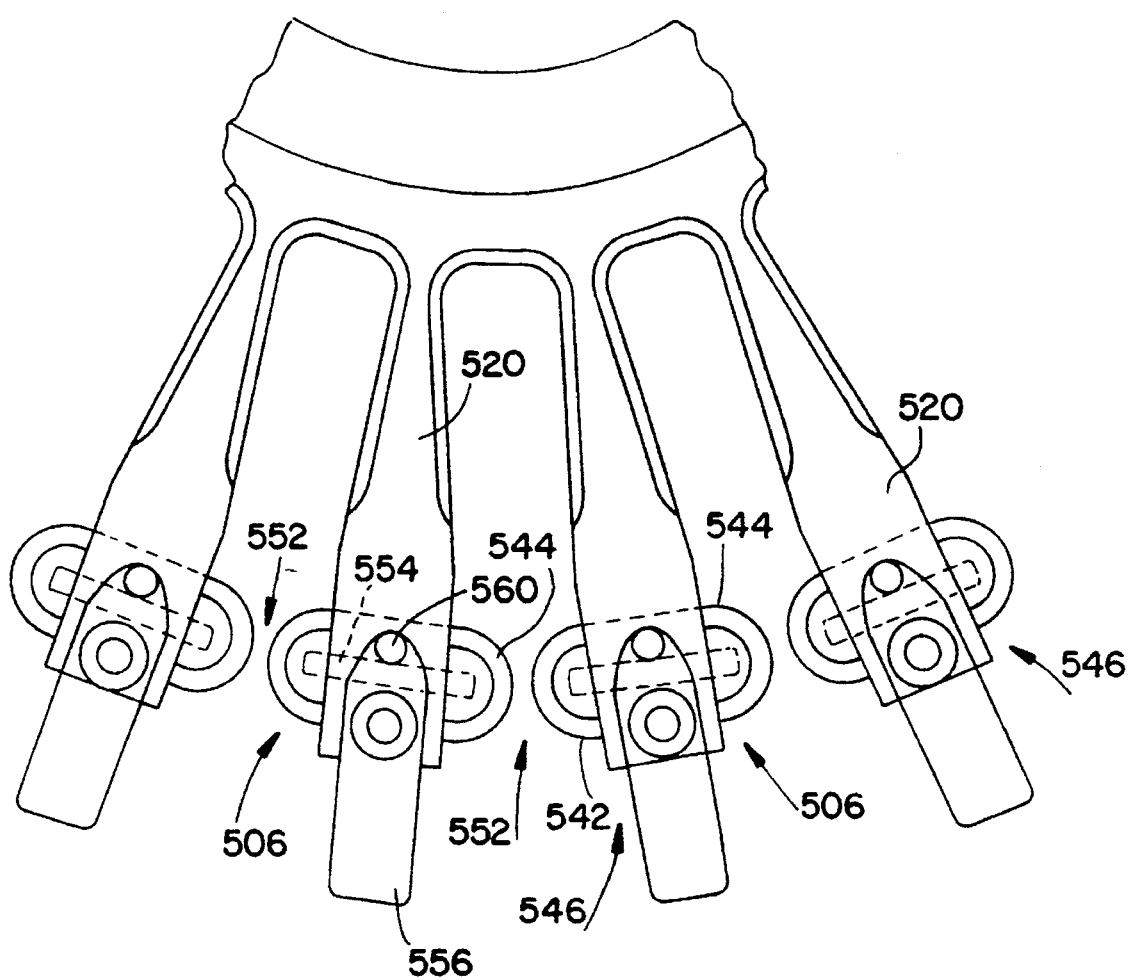
FIG. 23 is an enlarged view showing the rotor arms and cassette mounting brackets of the centrifuge.
Figure 24:
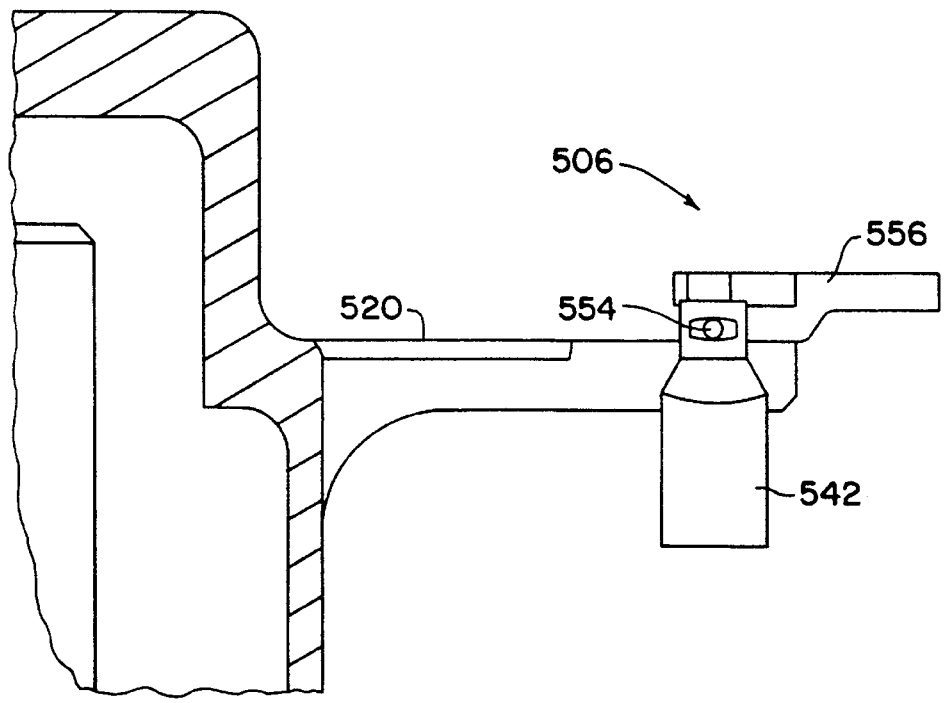
FIG. 24 is a side view of one of the rotor arms and mounting brackets.
Figure 25:
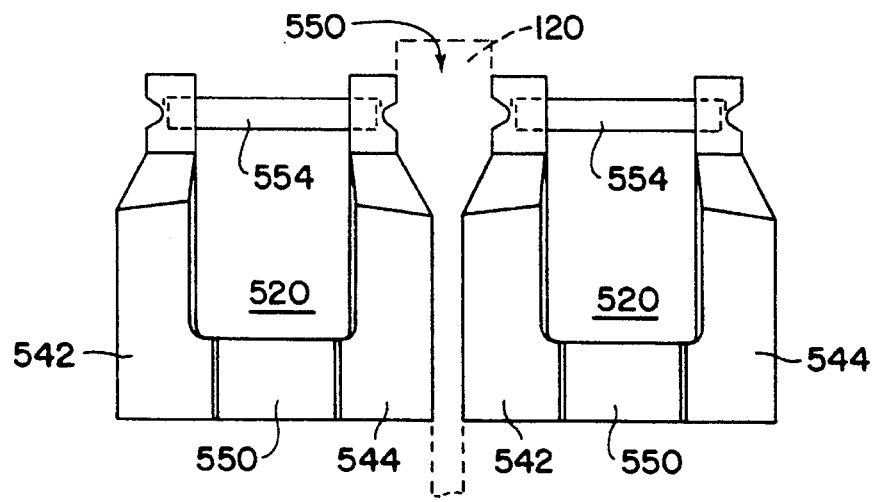
FIG. 25 shows a pair of the mounting brackets, and a cassette held therebetween.
Figure 26:
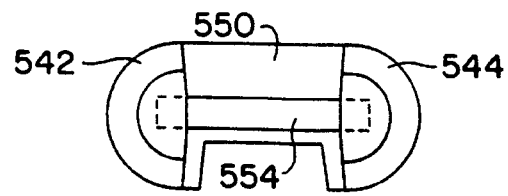
FIG. 26 is a top view of one of the mounting brackets.

With reference to FIGS. 20–22, centrifuge 500, generally, comprises rotor 502, motor 504, and a multitude of cassette mounting brackets 506; and preferably, centrifuge 500 further includes housing 510, support subassembly 512, and level detection subassembly 514. Rotor includes rotatable body 516 and a multitude of arms 520, and centrifuge housing 510 includes bottom section 522 and cover 524. More specifically, support subassembly 512 includes a generally horizontal lower plate portion 526 and upwardly extending first and second circular flanges 526a and 526b. Support subassembly 512 is securely connected to instrument panel 106, and one or more connecting or mounting members 530 may be disposed between panel 106 and support subassembly 512 to facilitate connecting the support subassembly thereto or to allow limited flexing or other movement of subassembly 512, and the centrifuge 500, relative to panel 106.

First circular flange 526a forms a central opening, and motor 504 is positioned therein and secured to lower plate portion 526. Motor 504 extends upward from support subassembly 512, with rotatable motor shaft 504a extending substantially vertically.

Rotor 502, specifically body 516 thereof, is mounted on motor shaft 504a for rotation therewith. As particularly shown in FIG. 20, rotor body 516 includes upper horizontal wall portion 516a and cylindrical vertical side wall portion 516b connected to and extending downward from the upper wall portion 516a, and motor 504 is substantially enclosed within the rotor body. Rotor arms 520 are connected to rotor body 516 for rotation therewith about motor shaft 504a, and arms 520 extend radially outward from the rotor body. Arms 520 are uniformly spaced around rotor 502 and the outer or distal end of each arm forms two through openings 520a and 520b. In addition, arms 520 are generally flat and are positioned in a common plane, substantially perpendicular to motor shaft 502a.

Level detection subassembly 514 is provided to help insure that centrifuge 500 remains level as the centrifuge rotates. Numerous level detection sensors or devices are well known in the art and may be employed in centrifuge 500. In addition, a position controller or detector 534 may be provided to control or detect the angular rotation or position of motor shaft 504a and, thus, the angular rotation or position of rotor 506. Any suitable position controller or detector may be used in the centrifuge.

With particular reference to FIGS. 23–26, cassette mounting brackets 506 are mounted on rotor arms 520 and form cassette receiving means to hold cassettes 120 on rotor 502 for rotary movement therewith about motor shaft 502a and also for pivotal or swinging movement about the outward ends of arms 520. The mounting brackets 506 are substantially identical; and each bracket includes left side member 542, right side member 544, mounting means 546, and connecting means 550.

Each mounting bracket 506 is mounted on and laterally straddles a respective one of the rotor arms 520; and each pair of adjacent brackets, form a respective one receiving slot 552 having a shape matching the shape of the upper portion of a cassette 120. In use, as particularly shown in FIG. 25, a cassette 120 is positioned in this receiving slot 552, with the upper portion of the cassette nested between the brackets 506.

Mounting means 546 is provided to pivotally mount brackets 506 on arms 520, and preferably the mounting means includes rod 554, retaining member 556, and pin 560. Rod 554 is positioned on the arm 520 and extends to both lateral sides thereof; and the left and right side members 542 and 544 of bracket 506 are mounted on rod 554, specifically the left and right ends thereof respectively, for pivotal movement about the axis of the rod. Retaining member 556 is releasably connected to rotor arm 520 and extends over mounting rod 554 to hold the mounting rod on the rotor arm. Also, pin 560 is connected to and extends radially upward from rotor arm 520, radially inward of mounting rod 554 so that the mounting rod is radially captured between pin 560 and retaining member 556.

Connecting means 550 connects the left and right side members 542 and 544 of each bracket 506 for pivotal movement together about mounting rod 554. Any suitable connecting means 550 may be used in bracket 506; and for example, the connecting means may comprise a lower leg integrally connected to both side members 542 and 544. In the operation of centrifuge 500, cassettes 120 are placed in the receiving slots 552 defined by brackets 506. The centrifuge rotates these cassettes about shaft 504a; and as a result, the cassettes pivot outward about the mounting rods 554. When the centrifuge stops rotating, the cassette tend to pivot back downward about mounting rods 554.

As mentioned above, preferably centrifuge 500 rotates the cassette first at a slower speed, for example at 55 g, and then at a higher speed, such as 199 g. The low speed phase at 55 g pushes the cells to the surface of the beads and induces the cells to come into contact. This has two benefits: it accelerates the reaction, and maximizes the cell to cell contact to achieve optimal reactivity and agglutination, if it occurs at all. The higher speed, at 199 g, pushes the cells through the bead column and causes segregation of agglutinated from non-agglutinated cells.

With prior art centrifuges, occasionally a cassette will not pivot completely downward, and this may cause difficulties in removing the cassette from the centrifuge. This difficulty is prevented in centrifuge 500 because the brackets 506, specifically connecting means 550, interconnect the cassettes 120 so that, after centrifuging, the cassettes pull each other back down into the desired position, insuring that all of the cassettes pivot downward into that position.

Figure 27:
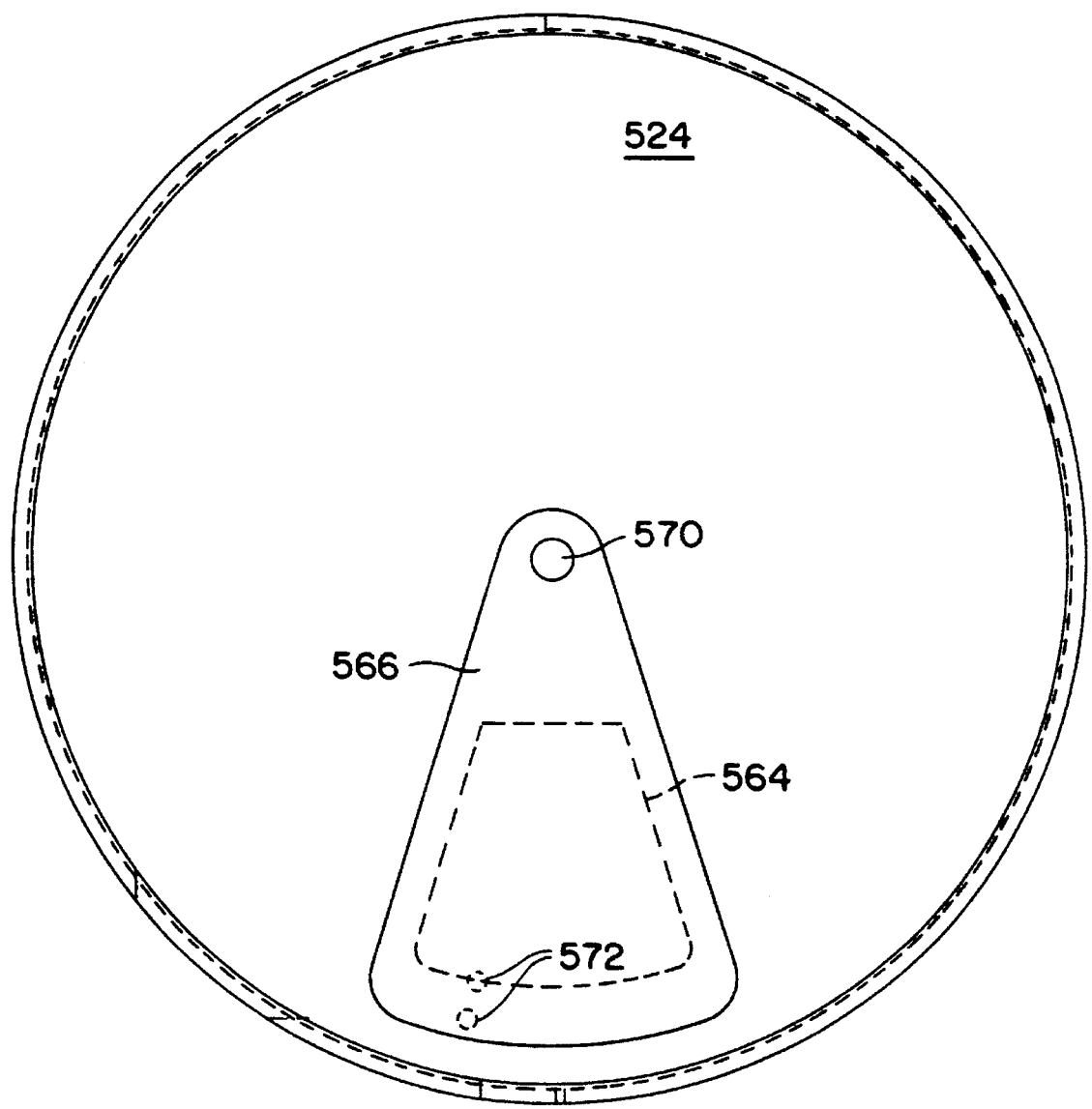
FIG. 27 illustrates the centrifuge cover.

With particular reference to FIG. 27, cover 524 of centrifuge 500 forms an access opening 564 to allow cassettes 120 to be placed in and removed from the centrifuge, and slide 566 is mounted on the cover to selectively open and close that opening 564. More specifically, slide 566 is mounted on cover 524 for pivotal sliding movement over the top surface of the cover and about a center pin 570, which is centrally located on the top surface of the cover. Slide 566 may be moved between a closed position, shown in FIG. 28, in which the slide covers opening 564, and an open position in which the slide is positioned to the left or to the right of opening 564 and does not extend over that opening. One or more small projections 572 are connected to and extend upward from slide 566 to facilitate moving the slide; and, for example, gripper 704 of transport assembly 700 may be used to pivot the slide to selectively open and close the centrifuge access opening 564.

Figure 28:
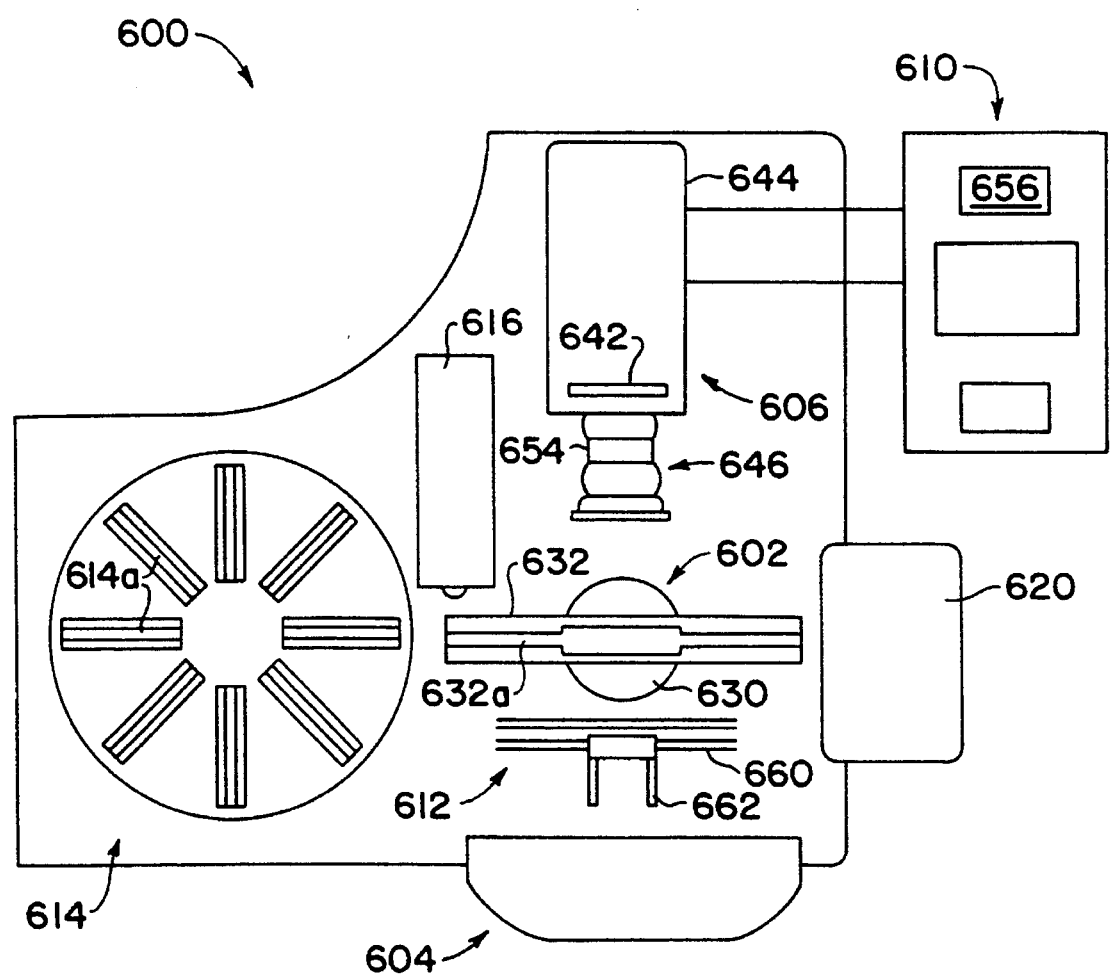
FIG. 28 illustrates in greater detail the analysis station of the instrument shown in FIGS. 1–4.
Figure 29:
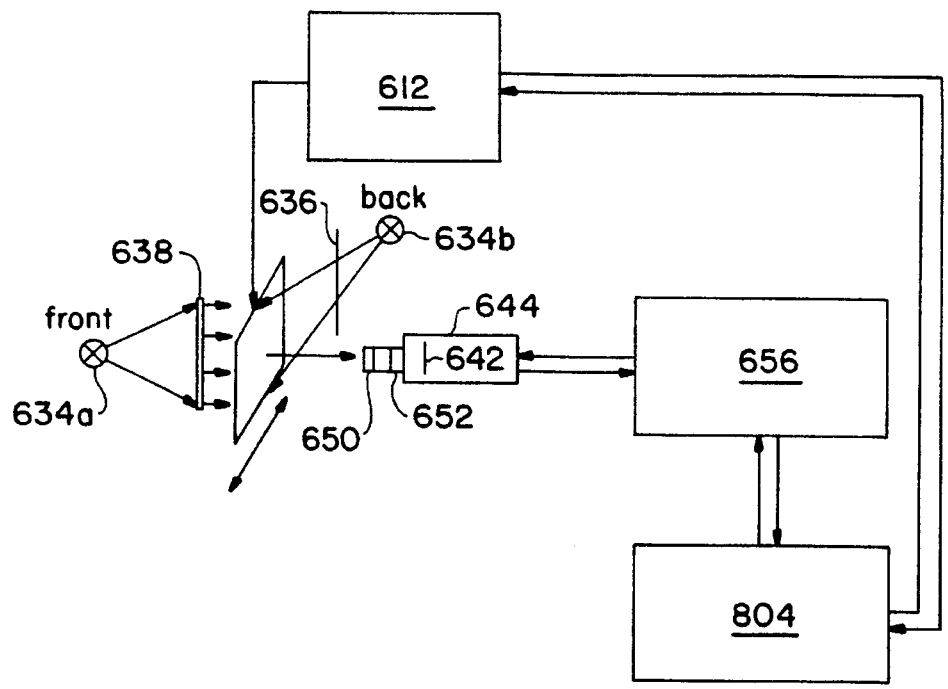
FIG. 29 is a schematic diagram of portions of the analysis station.

FIGS. 28 and 29 illustrate analysis station, or automated optical reading station, 600 in greater detail. With the preferred embodiment of station 600, holding means 602 includes base 630 and frame 632; and illumination means 604 includes a pair of fluorescence lights 634a and 634b, neutral density filter 636, and diffuser 638. Imaging subsystem 606 includes pixel array 642, housing 644, and lens assembly 646; and this lens assembly, in turn, includes lens 650, filter 652, and lens housing 654. Also, the preferred processing subsystem 610 includes preprocessor 656, which is connected to control means 800, specifically processor 804 thereof; and the preferred transport subassembly shown in FIG. 28 includes support means 660 and mover 662.

Analysis station 600 is described in detail in copending application Ser. No. 08/163,996, for "Method and System for Classifying Agglutination Reactions," filed herewith, now U.S. Pat. No. 5,594,808 the disclosure of which is herein incorporated by reference.

Generally, though, holding means 602 is provided to hold a cassette 120 for analysis, and illumination means 604 is provided to produce an illuminated image of one or more columns of the cassette on imaging subsystem 606. Subsystem 606 generates a set of signals representing the illuminated image formed thereon and then transmits those signals to preprocessor 656. The preprocessor converts those signals to digital data values and then transmits those data values to processor 804 to analyze the image produced on subsystem 606. In particular, as discussed subsequently in more detail, processor 804 processes the data values according to a predetermined program to determine whether an agglutination pattern is present in the test sample being analyzed and, if so, to classify that pattern in one of a plurality of predefined classes.

With particular reference to FIG. 28, frame 632 of holding means 602 forms an elongated channel 632a for holding a cassette 120; and preferably, the longitudinal ends of channel 632a are open to facilitate or to allow sliding movement of cassette 120 into, through, and then from channel 632a.

Also, frame 632 is preferably rotatably mounted on base 630 for pivotal or rotary movement about a central vertical axis, and a motor is connected to frame 632 to pivot or rotate the frame about that axis.

Illumination means 604 directs light through the cassette 120 held in frame 632 and onto pixel array 642, which then generates a series of signals representing the cassette. Pixel array 642 is disposed inside a camera housing 644, and the pixel array is preferably comprised of a multitude of light sensors each of which is capable of generating a respective one electric current having a magnitude proportional to or representing the intensity of light incident on that sensor.

Lens 650 and filter 652 are located forward of pixel array 642 and are coaxially aligned with each other and with the pixel array, and lens 650 is positioned so that the pixel array is at the back focal plane of this lens. Preferably, lens 650 and filter 652 are mounted inside housing 654, which in turn is mounted on the front end of camera 644. The distance between the camera and the cassette 120 held in frame 632 is adjusted so that each image on the pixel array contains two columns 122 of the cassette.

Figure 30:
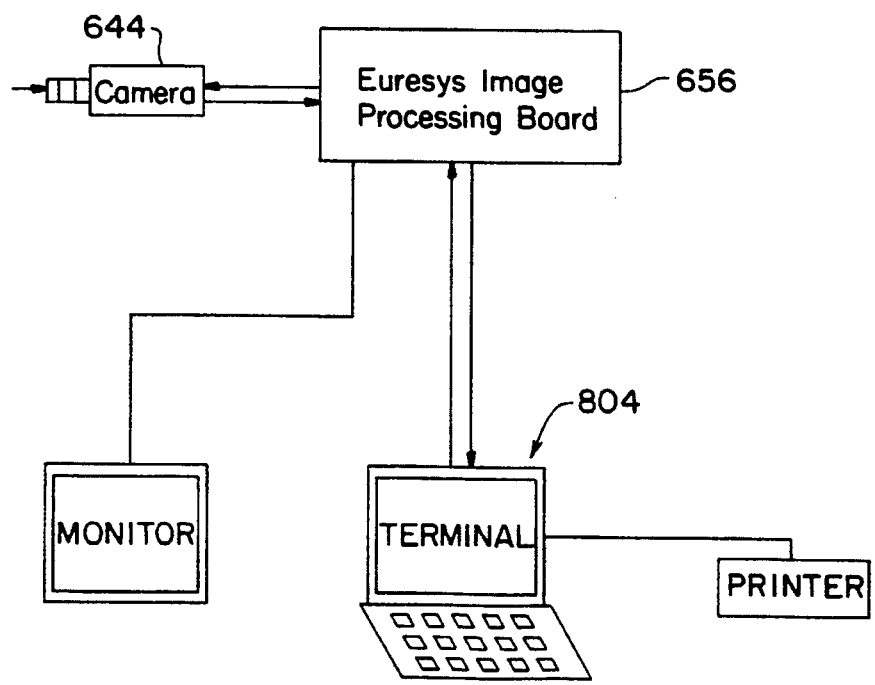
FIG. 30 is a schematic diagram of the processing subsystem used with the analysis station.

FIG. 30 is a block diagram illustrating the relationship between preprocessor 656 and main processor 804 in greater detail. The electric signals from the pixel array in camera 644 are conducted to preprocessor 656, which may be, for example, an image processing board made by Euresys S. A., of Belgium. This image processor then converts the electric signal from each pixel of array 642 into a respective one digital data value and stores that data value at a memory location having an address associated with the address of the pixel that generated the electric signal.

The data values stored in image processor 656 are available to main processor 804, which is connected to the image processor to obtain data values from and to transmit data values to that image processor. As explained in greater detail in copending application Ser. No. 08/163,996, for "Method and System for Classifying Agglutination Reactions," now U.S. Pat. No. 5,594,809 processor 804 is programmed to process and to analyze the data values stored in the image processor to identify the agglutination pattern, if any, in the test sample being analyzed.

With reference again to FIG. 28, storage means 614 is located adjacent holding means 602 and is provided for holding a multitude of cassettes 120, and preferably indexing means such as a stepper motor is provided for moving the storage means through a series of positions to align each of the cassettes held therein with the holding means 602. With the preferred embodiment of station 600 shown in FIG. 28, storage means 614 comprises a rotatable carousel including a rotatable base and a multitude of compartments. Each compartment forms a channel or slot 614a, and each of these slots extends along a radius of the carousel. Further, the indexing means may comprise a stepper motor, and each time the motor is actuated, the motor moves the carousel so as to align one of the slots 614a with channel 632a of frame 632.

Waste receptacle 620 is provided for receiving the cassettes from holding means 602 after the desired imaging has been completed. For example, the waste receptacle may be a container located below and adjacent the output end of channel 632a of frame 632, and positioned so that the cassettes that are slid out from channel 632a fall into receptacle 614 under the force of gravity.

Transport subsystem 612 of station 600 is provided to move test samples, particularly cassettes 80, into and then from holding means 602, specifically frame channel 632a.

More particularly, support means 660 supports mover 662 for sliding movement between carousel 614 and waste receptacle 620 and over frame 632. In use, mover 662 is positioned over the carousel, and as the carousel rotates to align a cassette with frame slot 632a, that cassette is moved into engagement with the mover. The mover then slides the cassette from carousel 614, into frame 632 and into a position directly forward of pixel array 642. After the desired imaging of the test sample is completed, the mover 662 is operated to slide the test sample through the output end of channel 632a and into waste receptacle 620. Alternatively, depending on the results of the analysis of the test sample, that test sample may be moved back into the carousel 614, or to another location where the test sample may be stored, for example, for further tests or for analysis by an operator.

Transport assembly 700 is preferably provided to move cassettes 120 around system 100. More particularly, gripper 704 is moved and operated to carry cassettes 120 from drawer assembly 900 to the incubator station 200; and after the cassette tops have been pierced open and the desired solutions have been dispensed into the desired columns 122 of the cassettes, gripper 704 moves the cassettes to the centrifuge 500. After the cassettes have been centrifuged, gripper then carries the cassettes to analysis station 600. In addition, preferably, transport assembly 700 may be operated to carry selected cassettes to holding area 950. This may be done, for instance, when it is determined that a particular cassette requires the personal attention of an operator. For example, depending on the results of the analysis of the cassette in station 600, the gripper 704 may pick a cassette up at the analysis station, and move the cassette to holding area 950, where the cassette may be stored for further tests or for analysis by an operator.

Figure 31:
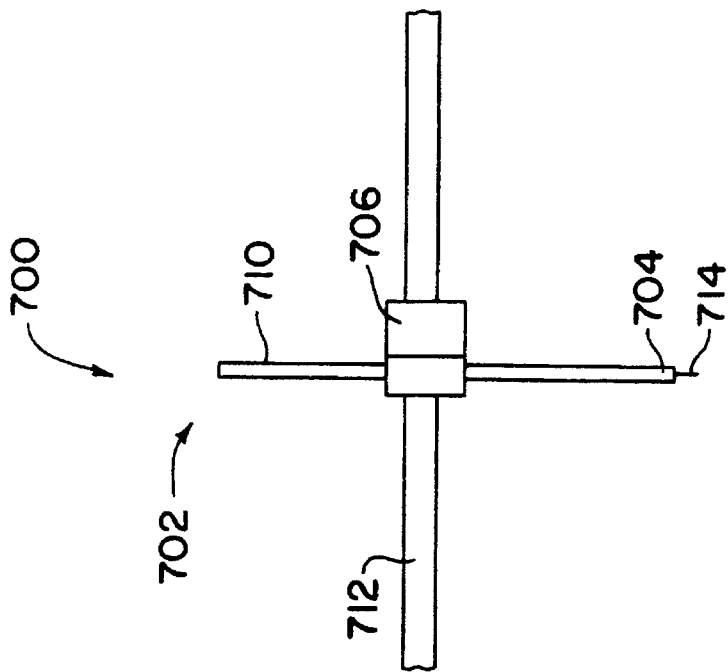
FIG. 31 illustrate a side view of the transport assembly of the blood analysis instrument shown in FIGS. 1–4.
Figure 32:
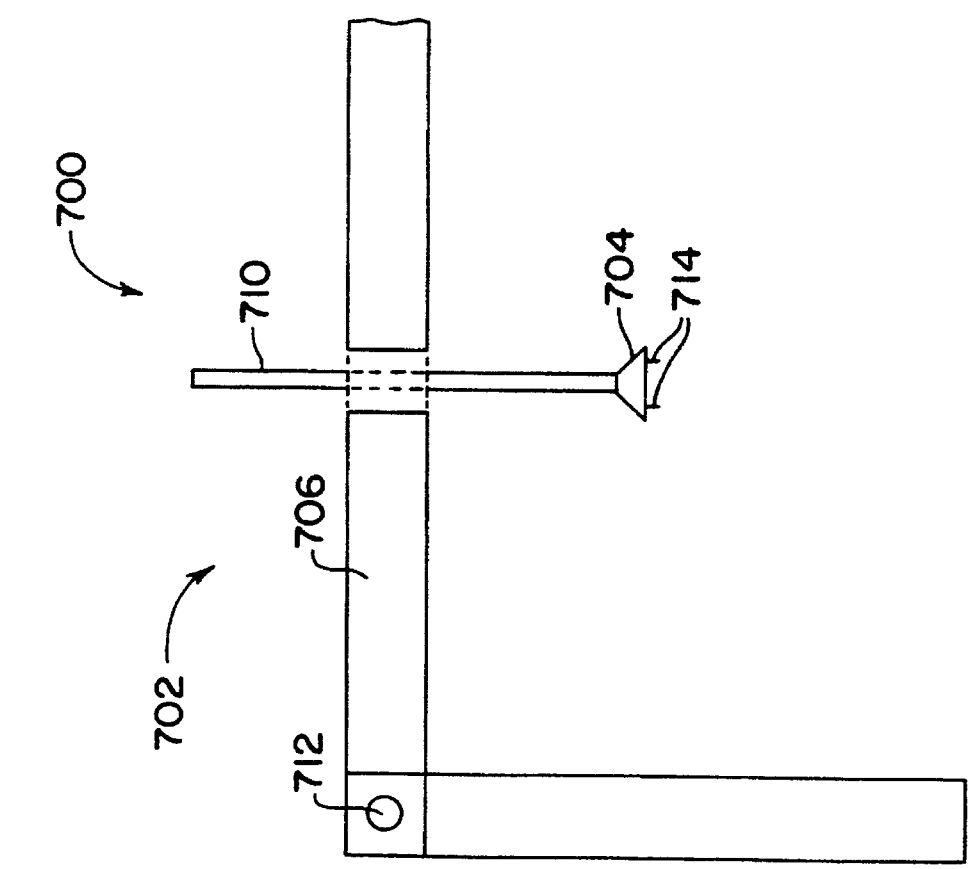
FIG. 32 is a front view of the transport assembly.
Figure 33:
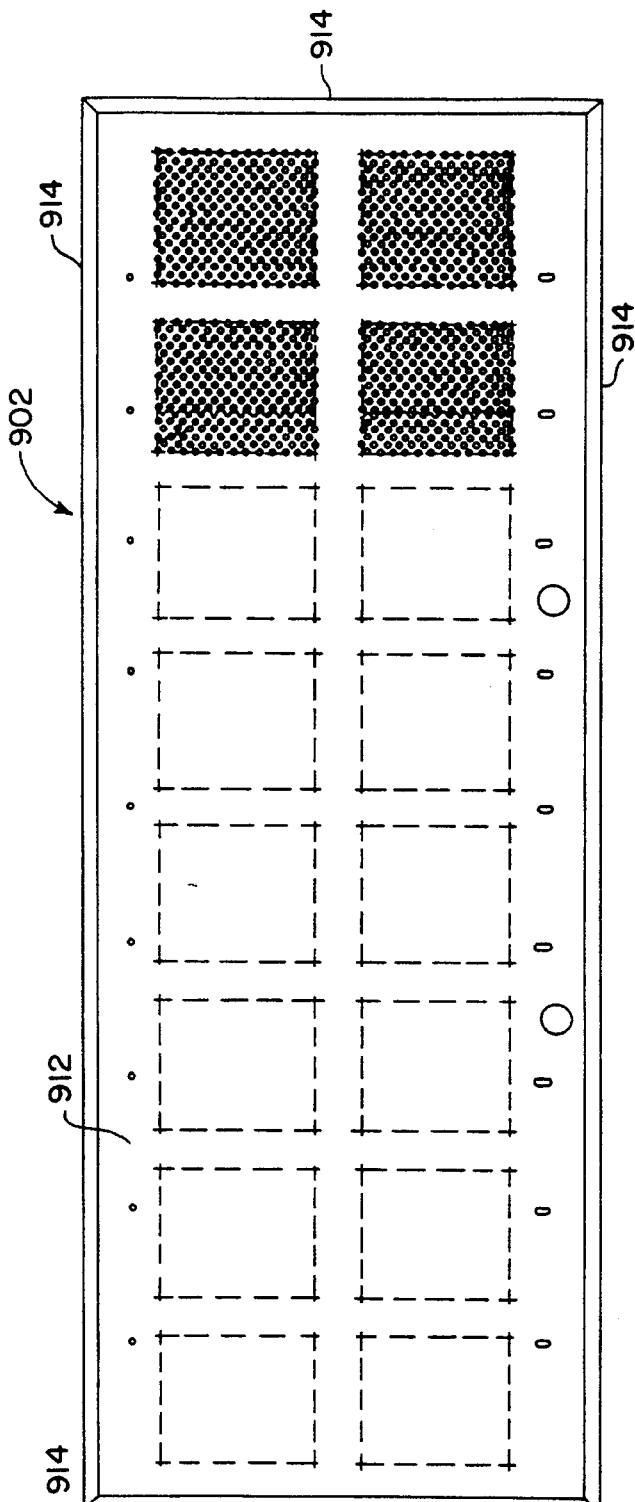
FIG. 33 is a top view of a drawer of the drawer subassembly of the instrument shown in FIGS. 1–4.
Figure 34:
FIG. 34 is a side view of the drawer.
Figure 35:
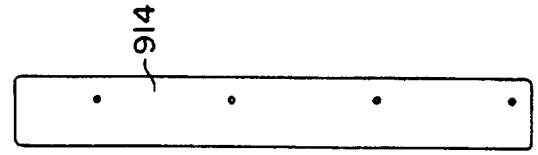
FIG. 35 is an end view of the drawer.

With particular reference to FIGS. 31 and 32, robot arm 702 preferably includes horizontal support bar 706 and vertical support rod 710. Bar 706 is supported for horizontal sliding movement along a support means including bar 712; and rod 710 is supported both for horizontal sliding movement along, and vertical sliding movement relative to, bar 706. Gripper 704 is connected to the lower end of robot arm, specifically rod 710, for movement therewith, and the gripper includes two opposing fingers 714 supported for sliding or pivoting movement toward and away from each other. These fingers 714 are moved toward each other to grip a cassette 120, and then moved away from each other to release a cassette from the gripper 704.

Suitable motors (not shown) are provided to move the robot arm in the x-, y-, and z- direction and to move the fingers 714 of the gripper 704. The robot arm and gripper may be operated in response to electric signals received from sensors or timers or both, to move the cassette in the desired manner. Preferably, the robot arm and gripper are controlled by a programmed, or programmable, processor 804 that operates transport assembly 700 in a predetermined manner and according to a multitude of variable factors.

Transport assembly 700 is described in greater detail in copending application Ser. No. 08/075,028, for "Transport System for Fluid Analysis Instrument," filed herewith, the disclosure of which is herein incorporated by reference.

With reference to FIGS. 2 and 33–39, the preferred embodiment of storage drawer assembly 900 includes drawer 902, slide tray 904, motor means 906, and sensor bar 910. Drawer 902 is supported in system 100 for movement between open and closed positions; and in particular, drawer 902 is located below instrument panel 106 and is supported for lateral sliding movement between the above-mentioned open and closed positions. Drawer 902 has a generally flat, rectangular bottom panel 912 and four side wall panels 914 that extend upward from the four side edges of the bottom panel and form an interior of the drawer. In its closed position, drawer 902 is located directly below instrument panel 106, and that panel substantially closes the top of the drawer interior. To move drawer 902 to its open position, the drawer is slid out from directly underneath panel 106, to a position in which the drawer is to the side of the panel and the interior of the drawer is open, providing access thereinto.

Drawer 902 may be supported in any suitable way for movement between the open and closed positions. Preferably a latch or similar means is provided to hold and lock the drawer selectively in the closed position, and the latch may be spring biased to a closed position. Preferably, the latch is moved between open and closed positions by means of an electric solenoid, which in turn is preferably controlled by processor 804. A manual release is preferably also available and may be used to open drawer 902 in the event of a loss of power to the processor. Also, drawer 902 itself may be spring biased toward its open position so that when the drawer latch is unlocked, the drawer automatically slides out of its closed position and toward its open position.

Slide tray 904 is positioned inside drawer 902 and is provided for holding a multitude of cassettes 120, and the tray is supported by the drawer for movement therein across at least a portion of the drawer. With particular reference to FIGS. 36 and 37, tray 904 also has a generally flat, rectangular bottom panel 916 and four side panels 920 connected to and extending upward from the four side edges of the bottom panel, forming an interior of the tray. Tray 904 also includes a multitude of longitudinal dividers 922 that separate the tray into a multitude of channels or sections 924. Preferably, these dividers extend along the length of the tray, are parallel to each other and are uniformly spaced apart.

In use, a multitude of cassettes 120 are positioned in each tray channel 924, with the front and back faces of each cassette extending laterally across the tray channel; and preferably, all of the cassettes have the same orientation in tray 904—that is, all of the cassettes face the same direction. Cassettes 120 of the type shown in FIGS. 5–7, are commonly sold in small cartons having a given number of cassettes, such as 20, and tray 904 is preferably designed so that two such cartons may be placed in each of the tray channels 904. These cartons typically have small recesses or sockets in the bottoms of the cartons to identify the back ends of the cartons; and small projections 926, adapted to fit into these sockets, extend upward from the bottom panel 916 of the tray. In use, the cassette cartons are placed in tray 904 with the bottom sockets of the cartons mounted directly onto the bottom projections 926 of tray 904, and this helps to insure that the cassettes are properly positioned and oriented in the tray.

In the preferred system 100, top instrument panel 106 forms a cassette access opening 108, shown in FIG. 1, directly above drawer 902; and, in the operation of system 100, gripper 704 of transport assembly 700 obtains cassettes 120 from drawer 902 by reaching into the drawer, through that access opening 108. To allow access to all of the cassettes in drawer 902, motor means 906 is connected to tray 904 to move that tray so that all of the cassettes therein may be moved directly beneath access opening 108. Preferably, motor means 906 is a stepper motor and is operated to move tray 904 stepwise longitudinally across drawer 902 to position each cassette 120 in each channel 924 of the tray directly beneath access opening 108.

Motor means 906 may be of any suitable type and connected to slide tray 904 in any suitable manner, and for example, the tray may be moved by a rack and pinion type drive. The motor and drive gear for the rack may be attached to a sliding mount that is spring loaded to keep pressure against the rack, and this spring also pushes drawer 902 open when the drawer latch is released. When the drawer opens, it slides out on two ball slides to allow the loading of cassettes. Also, preferably, when drawer 902 is opened and the drawer and tray are pulled away from the closed position of the drawer, the drive means for the tray becomes disengaged from the tray, and the tray is not moved by that drive means.

Sensor means 910 is provided to count the number of cassettes 120 in slide tray 904; and preferably, as shown in FIG. 39, the sensor means includes a sensor bar having a multitude of individual sensors 930. Bar 910 is mounted in instrument 100 so that the bar laterally extending over drawer 902, with a respective one sensor 930 located directly above each tray channel 924. With this embodiment of drawer assembly 900, motor means 906 may also be operated to move the cassettes 120 in tray 904 past sensor bar 910. Each time one of the cassettes 120 moves beneath one of the sensors 930, that sensor generates a respective one signal; and these signals allow a sensor control module to generate a list indicating all the occupied positions in the cassette drawer, and which list can then be sent to the STU processor 804. Preferably, sensor bar 910 is mounted on the under surface of instrument panel 106, immediately adjacent to access opening 108. In addition, preferably the sensors 930 are foil sensors that detect the top foil strip 124 on each of the cassettes 120.

Signal means, such as light emitting diodes, may be used to indicate the status of various matters. For example, one signal may be-used to indicate that drawer assembly 900 is in order and functioning as it should, another signal may be used to indicate that drawer 902 is open, and still another signal may be used to indicate that motor means 906 is not operating properly or that slide tray 904 is not properly moving across the drawer. Also, a sensor may be provided to sense when drawer 902 is in the closed position, and this sensor may generate and transmit to processor 804 a signal each time the drawer is moved into its closed position.

Figure 40:
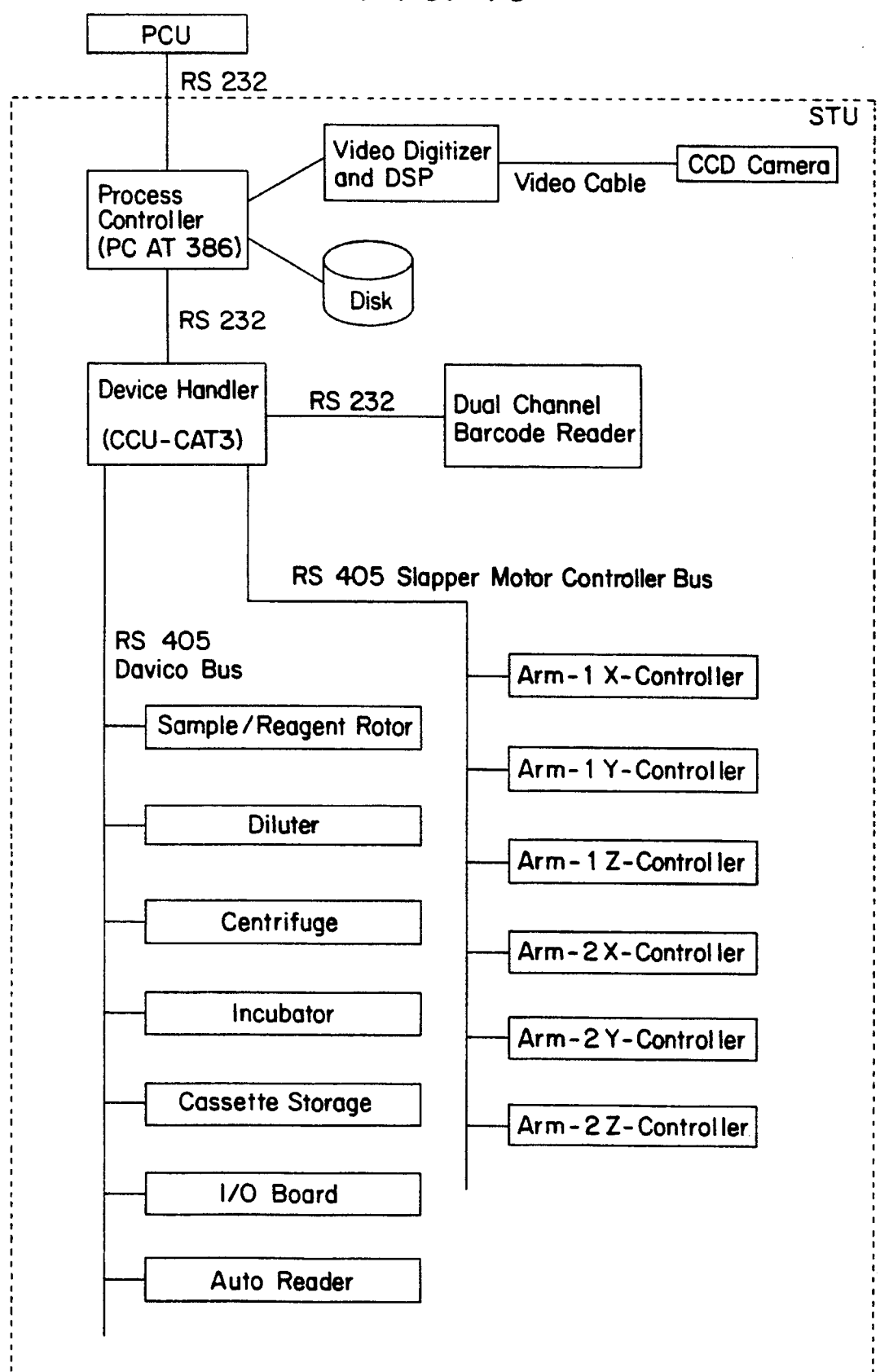
FIG. 40 shows the architecture of the control system of the blood analysis instrument illustrated in FIGS. 1–4.

Control means 800, generally, controls and operates the stations and assemblies of instrument 100 in order to move cassettes 120 through the instrument in the desired manner and to perform the requested tests on those cassettes. Control means 800 is also used to process the data generated by analysis station 600 to determine if any reaction occurred in the cassettes being analyzed. More specifically, with reference to FIGS. 4 and 40, process controller 804, which includes a processing unit, transmits command signals to Central Control Unit 802 to operate the stations and assemblies of instrument 100, and the Central Control Unit converts these command signals to control signals that are transmitted to the individual motors in instrument 100 to operate those motors. Operator input to process controller 804 is available via a second unit, referred to as an external processor, which preferably is a personal computer, including a processor unit, a keyboard 806, and a monitor 810.

Figure 41A:
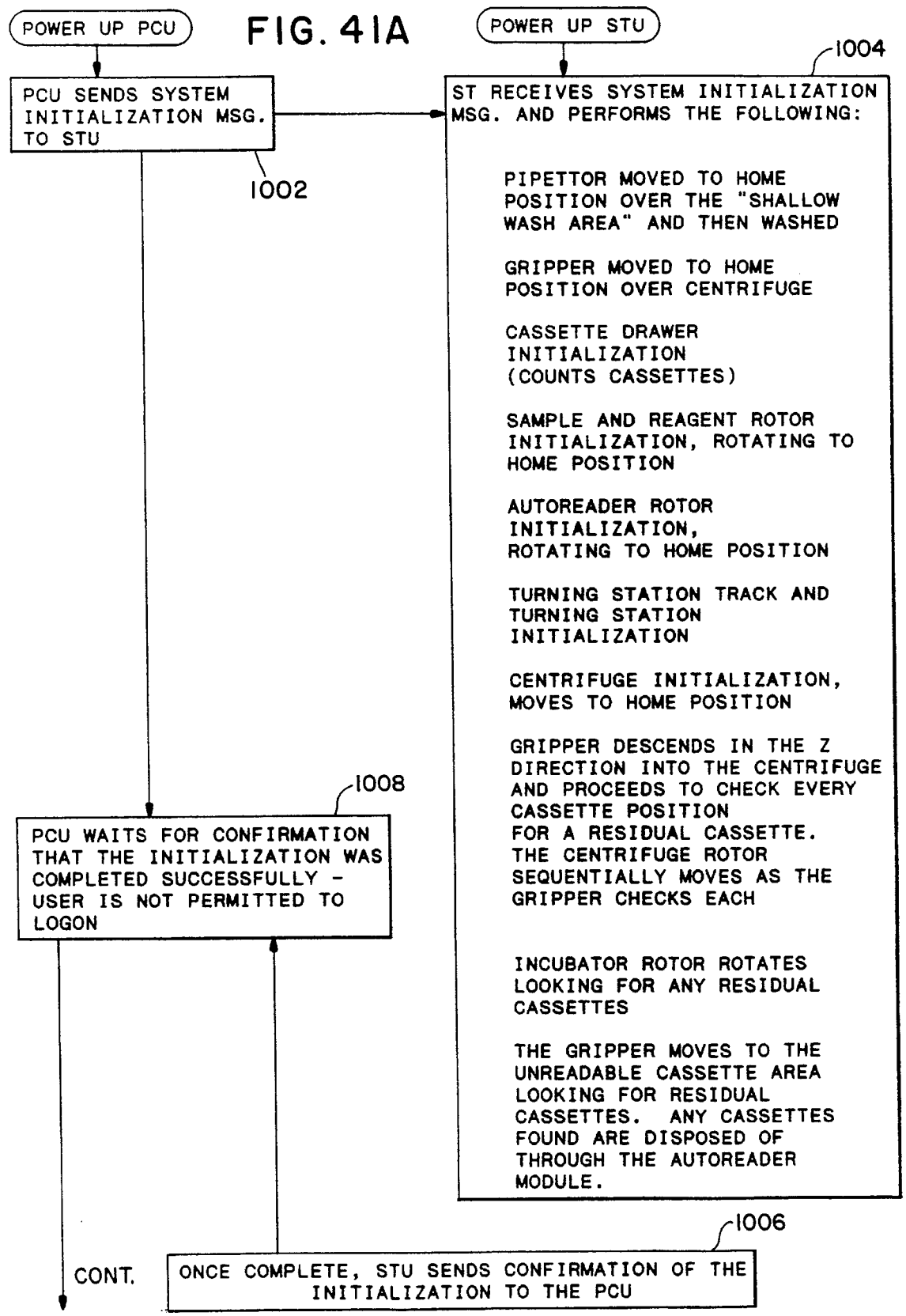
Figure 41B:
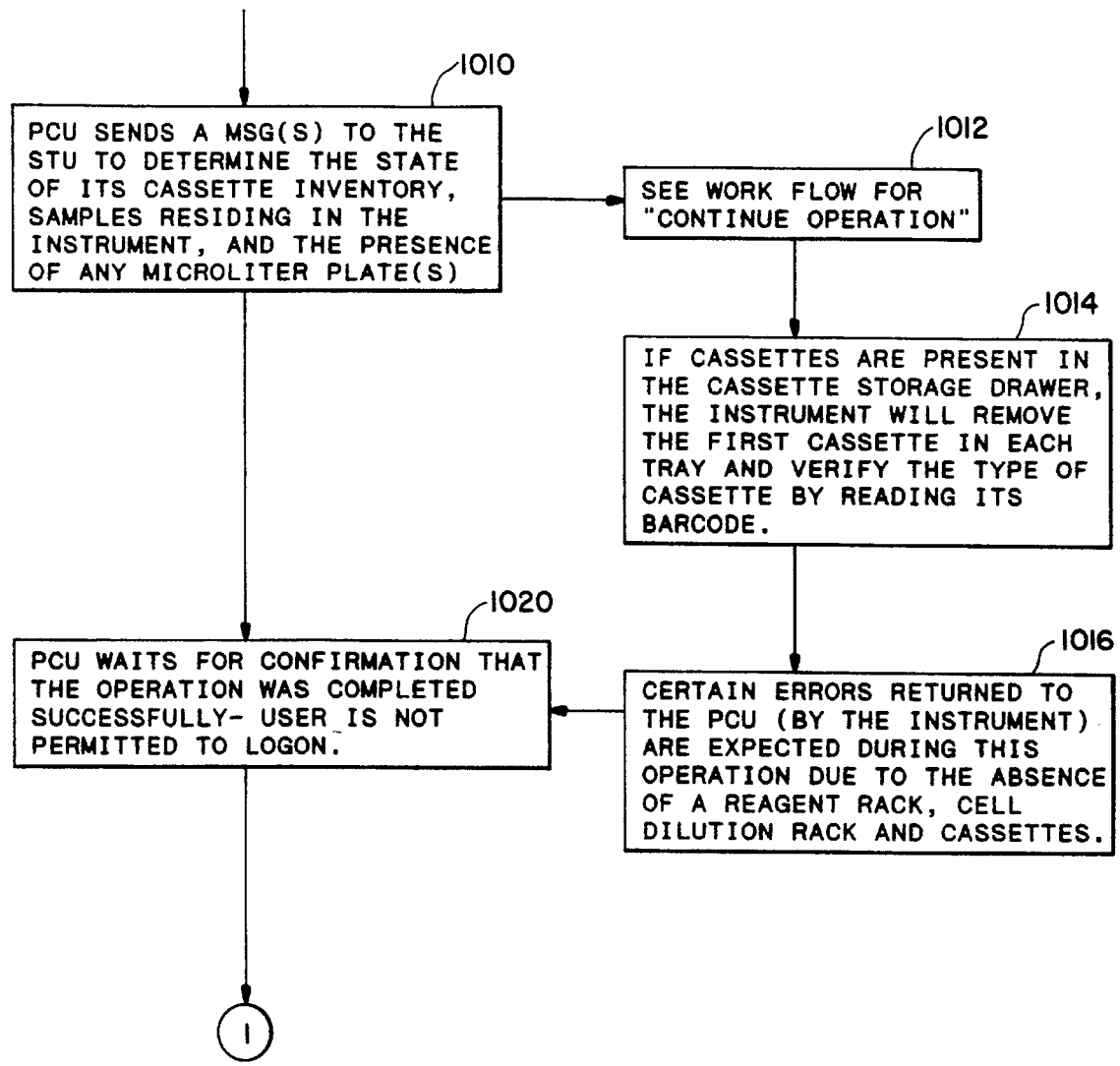

FIGS. 41 and 42 show a main work flow diagram for instrument 100. After power is provided to the PCU and the STU, the PCU, at step 1002, sends a system initialization message to the STU; and in response, the STU performs several initialization steps 1004. In particular, the pipette is moved to a home position over the shallow wash area and then washed in that area, and the gripper of the transport assembly is moved to a home position over the centrifuge. The cassette drawer is initialized, and in particular, the number of cassettes in the drawer is counted. The sample, reagent, and autoreader rotors are rotated to respective home positions, and the frame 632 and holding means 602 of station 600 are initialized. The centrifuge is moved to a home position; and the gripper descends in the z-direction and, using a foil sensor located in the bottom of the gripper, checks every cassette position in the centrifuge for a cassette.

To allow the gripper to do this, the centrifuge motor rotates the centrifuge stepwise to position each cassette receiving position, one at a time, below the gripper; and in particular, to position each cassette receiving position, one at a time, below the gripper access opening in the centrifuge cover. In addition, the incubator rotor rotates the incubator rack 202, and the incubator is checked for any residual cassettes. This also may be done by using a foil sensor located in the bottom of gripper 704. Also, after the gripper has completed checking the centrifuge for residual cassettes, the gripper then moves to the holding area 950, referred to as the unreadable cassette area, and checks that area for any residual cassettes. If any cassettes are found, the cassettes are carried by the gripper to and through the autoreader module and deposited in the waste receptacle.

After these initialization steps are completed, the STU, at step 1006, transmits a signal to the PCU confirming completion of this initialization procedure. The PCU, after sending the system initialization signal to the STU, waits, at step 1008, for receipt of the initialization complete signal from the STU; and in the meantime, the PCU preferably does not allow the user further access to the PCU.

After receipt of the initialization complete signal, the PCU then sends a message to the STU at step 1010 to check various items, and in particular, to determine the state of its cassette inventory, to identify samples residing in the instrument, and to determine if any microtiter plates are present. In response to receipt of this message from the PCU, the STU, at step 1012, initiates a procedure referred to as the continue operation procedure.

Figure 43:
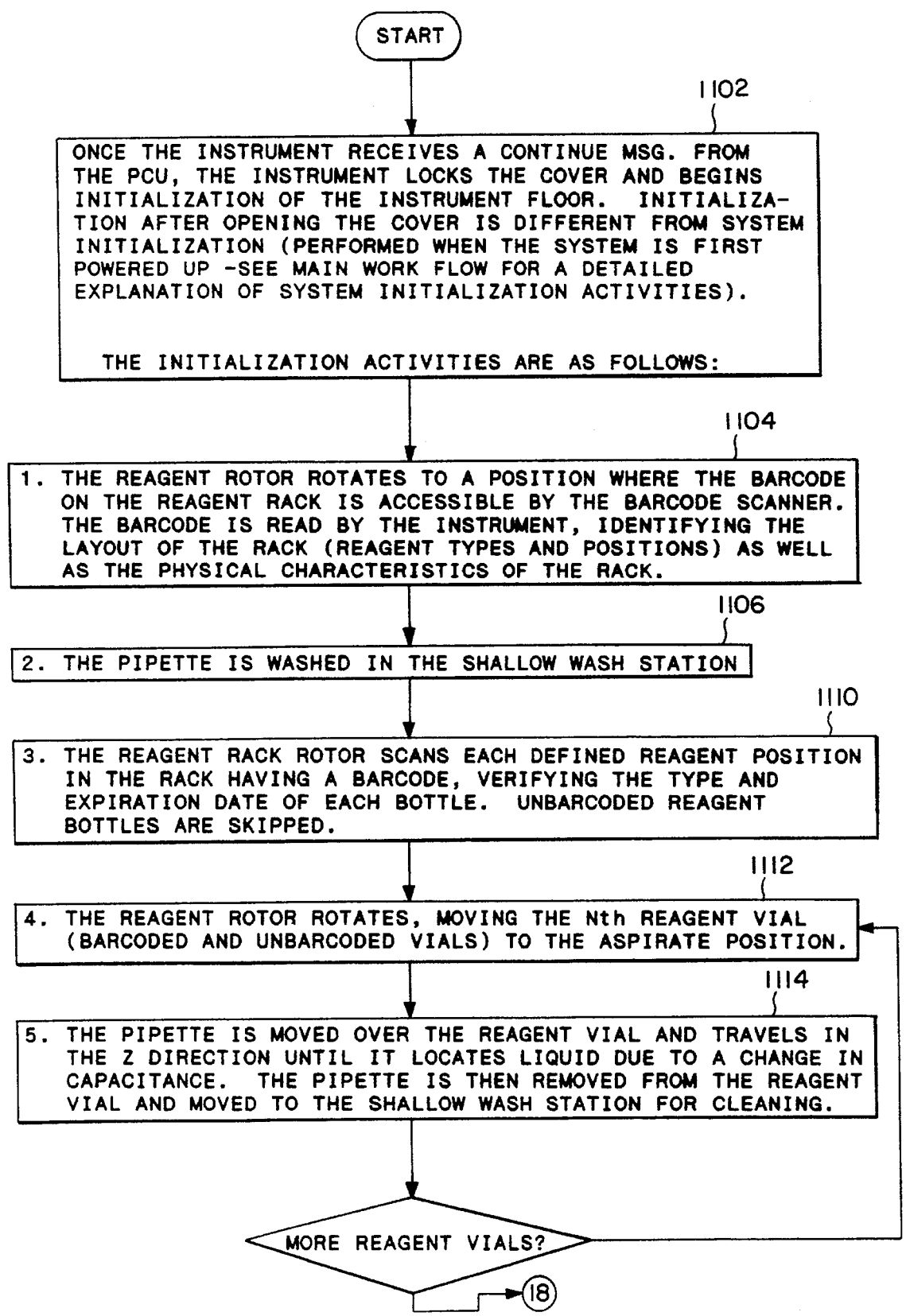

The continuation operation procedure, generally, prepares various items on the instrument for operation. With reference to FIGS. 43 and 44, the continuation procedure, at step 1102, locks the instrument cover; and then the reagent rotor, at step 1104, rotates the reagent rack to a position where the bar code on the rack is accessible to the bar code scanner 310. That scanner then reads the bar code on the rack to identify the rack and the physical characteristics of the rack.

At step 1106, the pipette is washed in the shallow wash station; and at step 1110, the reagent rack rotor rotates that rack so that bar code scanner 310 reads the bar code of each reagent bottle to verify the reagent type and expiration date of each bottle. Then, at step 1112, the reagent rack is moved so that a given reagent bottle is in the aspirate position; and at step 1114, the pipette is moved over that reagent bottle, and the pipette is lowered, in the z-direction, into the reagent vial until the pipette contacts liquid. As mentioned above, the capacitance of the pipette is monitored, and this capacitance changes when that pipette becomes wet; and thus, the presence of liquid in the reagent vial is indicated by a change in the capacitance of the pipette. After it is determined that the reagent vial contains liquid, the pipette is removed from the vial and returned to the shallow wash station for cleaning. Steps 1112 and 1114 may be repeated, each time with a different reagent vial in the aspirate position, to check as many reagent vials as desired for liquid. Measuring the liquid height allows calculating the amount of reagent available, to provide resource management capabilities.

After steps 1112 and 1114 are completed, then at step 1116, the sample rack is rotated by the sample rack rotor so that the bar code on the sample rack is moved into a scanning position. The bar code reader 310 then reads that bar code to identify the physical characteristics of the sample rack. Then, at step 1120, the sample rack is rotated to move the sample tubes therein in sequence into the bar code scanning position, and the bar code 310 on each sample tube is read by the scanner. Steps 1116 and 1120 are repeated for each sample rack in the station 300.

At step 1122, the pipette is moved over and then lowered into the first well of the first cell dilution rack to check for the presence of liquid in that well, and this also is done by monitoring the capacitance of the lower portion of the pipette. The presence of liquid indicates that the cell dilution rack was previously used, and the absence of liquid indicates that the cell dilution rack is a new microtiter plate. Then, at step 1124, the pipette is moved over and lowered into the first well of the second dilution rack to check for the presence of liquid in that well and, in this way, to determine if that dilution rack is new or used.

After the cell dilution racks are checked, then at steps 1126 and 1130, the pipette is moved to a park position over the shallow wash area, and the gripper 704 is moved to park position near the special cassette rack 950. At step 1132, the reagent rotor is actuated to rotate the reagent rack to keep the reagent cells in suspension.

After these initialization activities are complete, then at step 1134, a confirmation signal indicating that the activities are completed is sent to the PCU from the STU.

As represented by step 1014 of FIG. 41, if cassettes are found in the cassette storage drawer during the Continuation Operation Procedure, then the gripper removes the first cassette in each tray in the storage drawer and moves that cassette to a position adjacent bar code reader 130, and the bar code on the cassette is read by the reader to verify that the cassette is of the type that belongs in that cassette tray. Also, as represented by step 1016, during this continuation operation procedure, error messages may be sent from the STU to the PCU to inform the PCU of any errors detected by the STU. After the PCU receives the confirmation signal that the above-discussed initialization activities are complete, then at step 1020, the PCU allows the user to logon to the system.

During these initialization activities, certain items, such as the reagent rack, the dilution rack and cassettes, may intentionally not be on instrument 100 at this time. If this is the case, then as represented by step 1016, error messages from the STU to indicate the absence of these items may be expected.

After the PCU receives the confirmation signal from the STU that the desired initialization activities are complete, the STU continues on with the main work procedure. Preferably, while the PCU is waiting for this conformation signal, the PCU does not allow the user further access to the PCU. Then, after the confirmation signal and the associated status information is transmitted to the PCU, at step 1022 the PCU permits the user to obtain further access to, or to log on, the PCU. At step 1024, the user then logs on the PCU, for example, by entering data via the keyboard, and preferably, in response, at step 1026, the PCU displays the term "Logon" on the keyboard terminal.

To obtain further access to the PCU, the user is preferably required to enter an identification code and a password via the keyboard, as represented by step 1030. If the password is accepted by the PCU, then at step 1032, the entire PCU menu bar is accessible to the user and the PCU is ready to begin operation of instrument 100. At this point in the procedure, the PCU proceeds on the basis that there are no cassettes in the cassette storage drawer, that both the reagent and sample racks are not in the instrument, and, of course, that there are no reagents and samples in the instrument. The PCU also proceeds on the basis that the cassette waste receptacle is not in the instrument.

Instrument 100 may be used for a multitude of specific procedures. As an example, the operation of the instrument to determine the blood type of a blood sample, a process referred to as an abo/rh→ABO/Rh procedure or test, will be described herein in detail.

The general steps in this operation are outlined at 1034 in FIG. 42. In a procedure referred to as cassette waste work procedure, the user opens the cassette waste area and places a new waste bag in the instrument; and in a procedure referred to as cassette storage work procedure, the user opens the cassette storage drawer and places the required cassettes therein. In a procedure referred to as instrument cover work procedure, the user opens the instrument cover and places in the instrument the required reagent rack, the required reagents, and two microtiter plates. In addition, in a procedure referred to as batch definition procedure, the user defines the abo/rh→ABO/Rh batch test; and the required blood samples are placed in the sample rack, in a procedure referred to as sample access door. Then, after instrument 100 has completed the operation, the user reviews and accepts or modifies the test results returned from the instrument, in a procedure referred to as the reviewing results procedure.

The cassette waste work procedure is outlined in FIG. 45. To request this procedure, the user, at step 1202, requests the "instrument" menu item from the PCU menu bar, and in response at step 1204, the instrument menu is displayed on the monitor. This menu lists the following items: flush instrument, open access door, open cassette drawer, open cover, and open trash door. The user, at step 1206, selects the open trash door item, and in response, at step 1210, the PCU sends the message or messages to the instrument to open the trash door. At step 1212, the instrument unlocks and opens that door and then sends to the PCU a message indicating that this has been done; and when the PCU receives this message, the PCU, at step 1214, displays the message "open trash door" on the monitor. As represented by step 1216, the user determines whether the instrument needs a new trash bag and, if appropriate, puts a new trash bag on the instrument, and the user, at step 1220, then enters a signal to the PCU that this has been done.

After receiving this message, the PCU at step 1222 then transmits a message to the STU indicating that the STU can lock the trash can door and perform any related, desired initialization procedures. When the trash can door is locked, then at step 1224, the STU transmits a signal to the PCU to indicate that this has been done. Preferably, if the STU is not able to lock the trash can door, an error signal indicating this fact is sent by the STU to the PCU; and, in response, the PCU displays a message, or otherwise indicates to the user, that the trash can door is not shut and alerting the user to take corrective action. Once the PCU receives the confirmation signal from the STU that the trash can door is locked, the PCU, at step 1226, removes the dialogue from the display terminal, and again displays the main PCU menu bar.

Figure 46A:
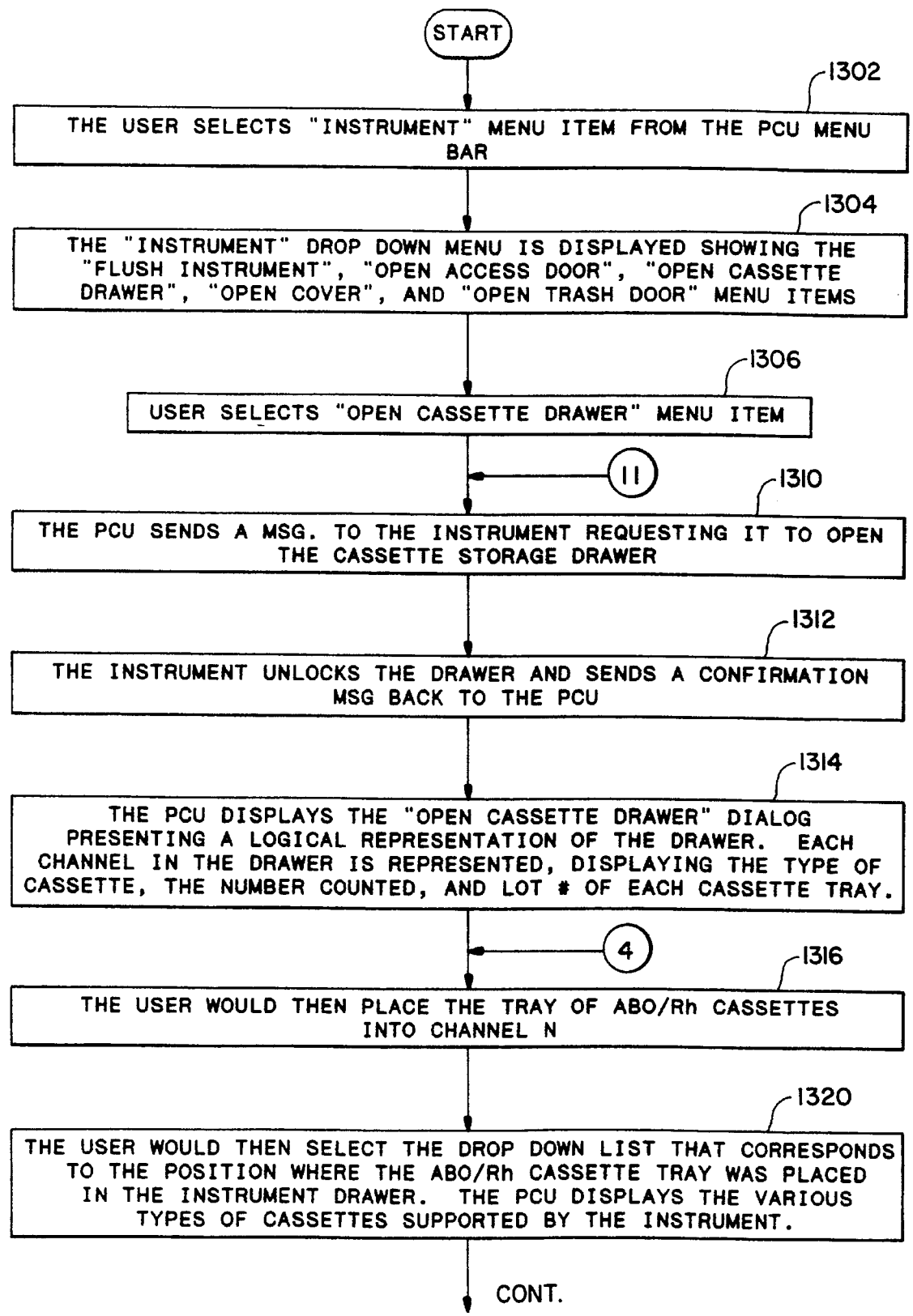
Figure 47:
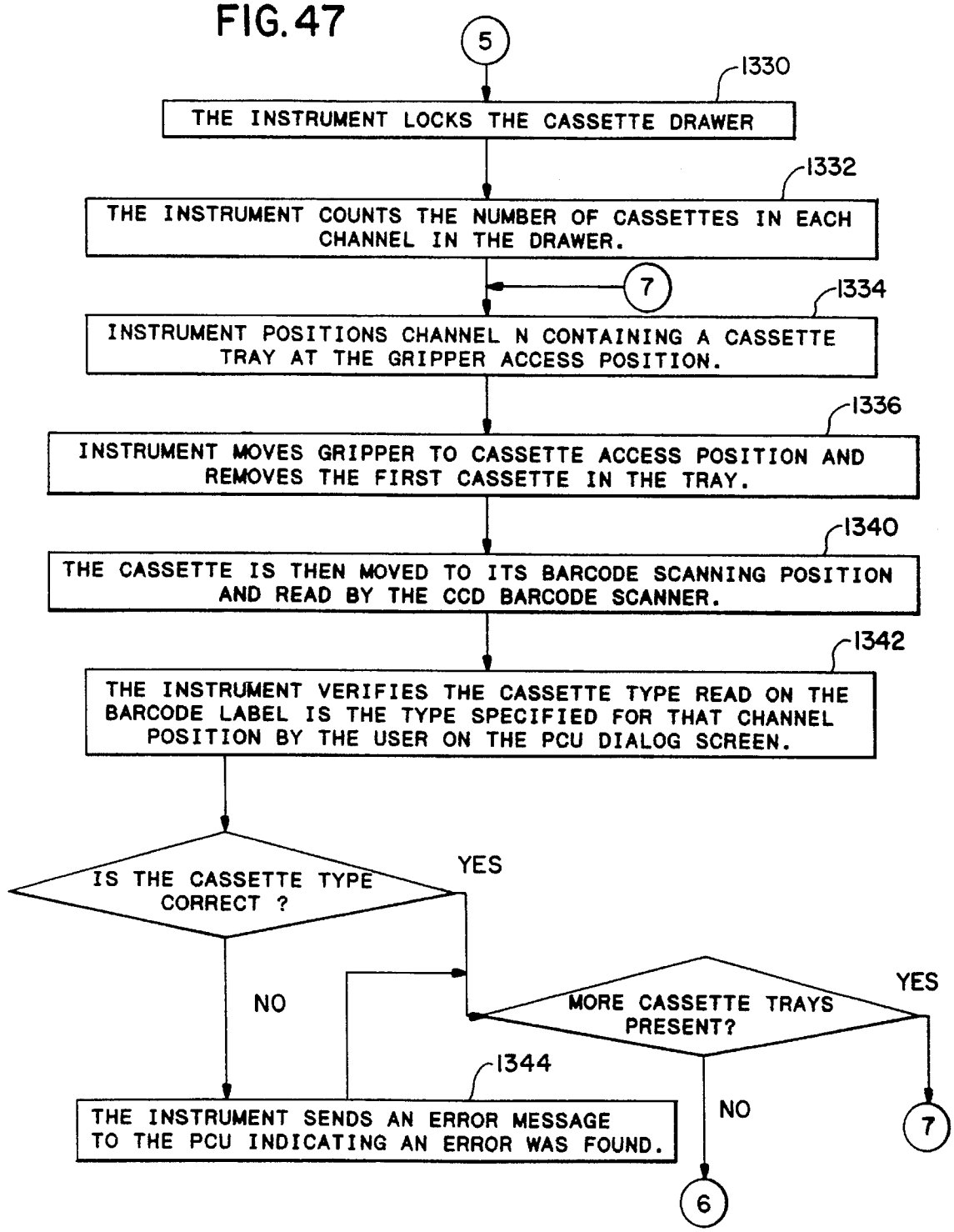

FIGS. 46–48 illustrate the cassette storage work procedure; and to request this procedure, the user, at step 1302, also requests the "instrument" menu item from the PCU menu bar. In response to this request, the PCU at step 1304, displays the instrument menu on the monitor, and at step 1306, the user selects the "open cassette drawer" menu item. The PCU transmits a message to the STU at step 1310, requesting the STU to unlock the cassette storage drawer; and at step 1312, the STU then unlocks that drawer and sends a message to the PCU confirming that this has been done. Next, at step 1314, the PCU displays the dialogue "open cassette drawer" on the monitor, and preferably a logical representation of the drawer is included in this display. In this logical representation, each channel may be represented in the display; and the display may also indicate the type of cassette, the number of cassettes counted in each tray and the lot number of each cassette. The user, at step 1316, then places a tray of abo/rh→ABO/Rh cassettes—that is, a tray of cassettes designed for use in an abo/rh→ABO/Rh test—in a given channel, designated as channel N.

The user then transmits a message to the PCU that abo/rh→ABO/Rh cassettes have been placed in the cassette channel, and preferably this is done by means of the graphics on the PCU monitor. For example, as represented by steps 1320 and 1322, in the logical representation of the cassette drawer, the user may designate or identify, for example by means of a cursor, the tray channel in which the cassettes were placed. Then, the PCU may display on the monitor, a list of the various types of cassettes that may be used in the instrument, and the user identifies one of these types as being the type that was placed in the designated tray channel. If more cassette trays are to be placed in the cassette drawer, then steps 1316, 1320, and 1322 are repeated, once for each cassette tray that is placed in the cassette drawer.

When the desired number of cassette trays has been placed in the cassette drawer, the user, at step 1324, transmits a message to the PCU that this has been accomplished, and preferably this also is done by means of a graphics interface on the PCU monitor. For instance, a series of words or terms, referred to as the "open cassette" dialogue box may be displayed on the monitor; and one of these terms, such as the phrase "ok" may be used to indicate that the trays have all been placed in the cassette drawer. When the desired trays have been placed in the cassette drawer, the user may designate or identify that "ok" term by, for example, positioning or aligning a cursor with that term.

After the cassette tray has been placed in the cassette drawer, then at step 1326 the PCU transmits a signal to the instrument to lock that drawer and to perform other initialization tasks for the drawer. As represented by steps 1330 and 1332, the instrument then locks the drawer and counts the number of cassettes in each channel in the drawer. Next, at steps 1334 and 1336, the instrument positions the cassette tray of one of the channels so that the first cassette in that tray is at the gripper access position, and the transport assembly is operated to grip that first cassette and remove it from the tray. Then, at steps 1340 and 1342, the cassette is moved to the bar code scanning position, and the reader reads the bar code on the cassette. The STU uses the information on the bar code to determine if the cassette is of the type that the user indicated was in that one channel. If the cassette is not of the correct type, the STU transmits an error message at step 1344 to the PCU, which then transmits a signal to alert the user of this error.

Steps 1334, 1336, 1340, 1342, and 1344 are repeated for each tray of cassettes that was placed in the cassette drawer. After the instrument has completed the cassette drawer initialization tasks, the STU transmits a message to the PCU to indicate that this initialization is complete, as represented by step 1346 in FIG. 46.

If any error messages were received by the PCU from the STU during the cassette drawer initialization procedure, then, after receipt of the drawer initialization complete signal, the cassette storage work program returns to step 1310. The PCU transmits a message to the STU requesting the STU to open the cassette drawer, and the program continues on from step 1310.

After steps 1310–1346 are completed without any error signals from the instrument, and the PCU receives the confirmation signal that the cassette drawer is locked, the PCU, at step 1350, removes the dialogue from the monitor, and displays the main PCU menu bar. Then, at step 1352, the PCU checks to determine if the instrument is capable of performing all of the tests that the user has requested. In particular, as represented by step 1354, the PCU checks to determine whether, for each requested batch, the instrument has (i) all the necessary blood sample tubes, (ii) the type and amount of reagents necessary to test the batch, and (iii) the type and number of cassettes required for the batch tests.

If the instrument is ready to perform the required tests, the PCU sends a signal to the instrument to begin the batch processing work procedure, discussed below. Further, the PCU produces the main screen display on the monitor, and the user continues to have access to the PCU to perform other tasks, such as defining other batches and looking at reports, while the batch processing work procedure is being performed.

Figure 49A:
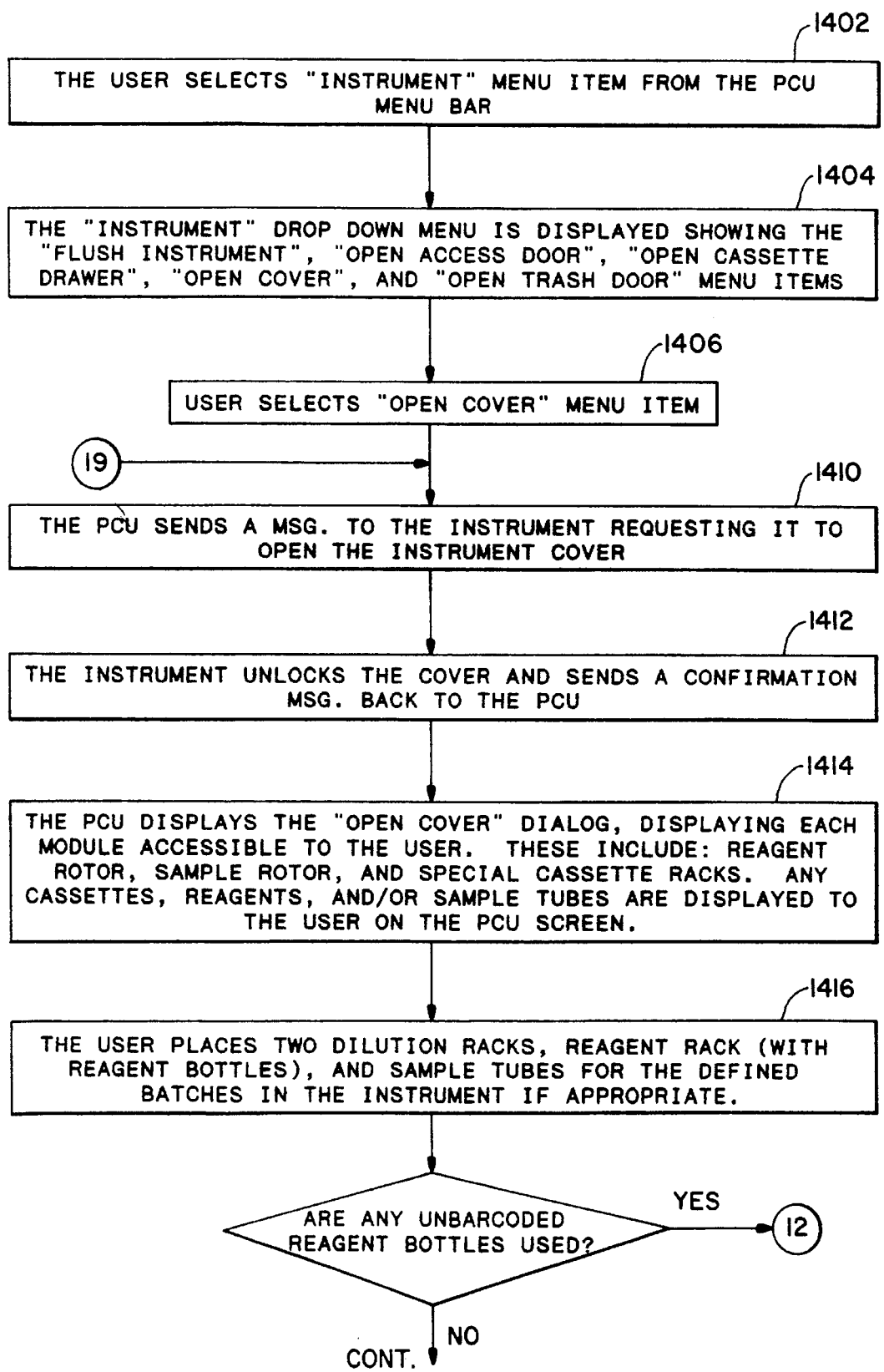
FIGS. 49–51 show an open instrument cover procedure for the blood analysis instrument.
Figure 49B:
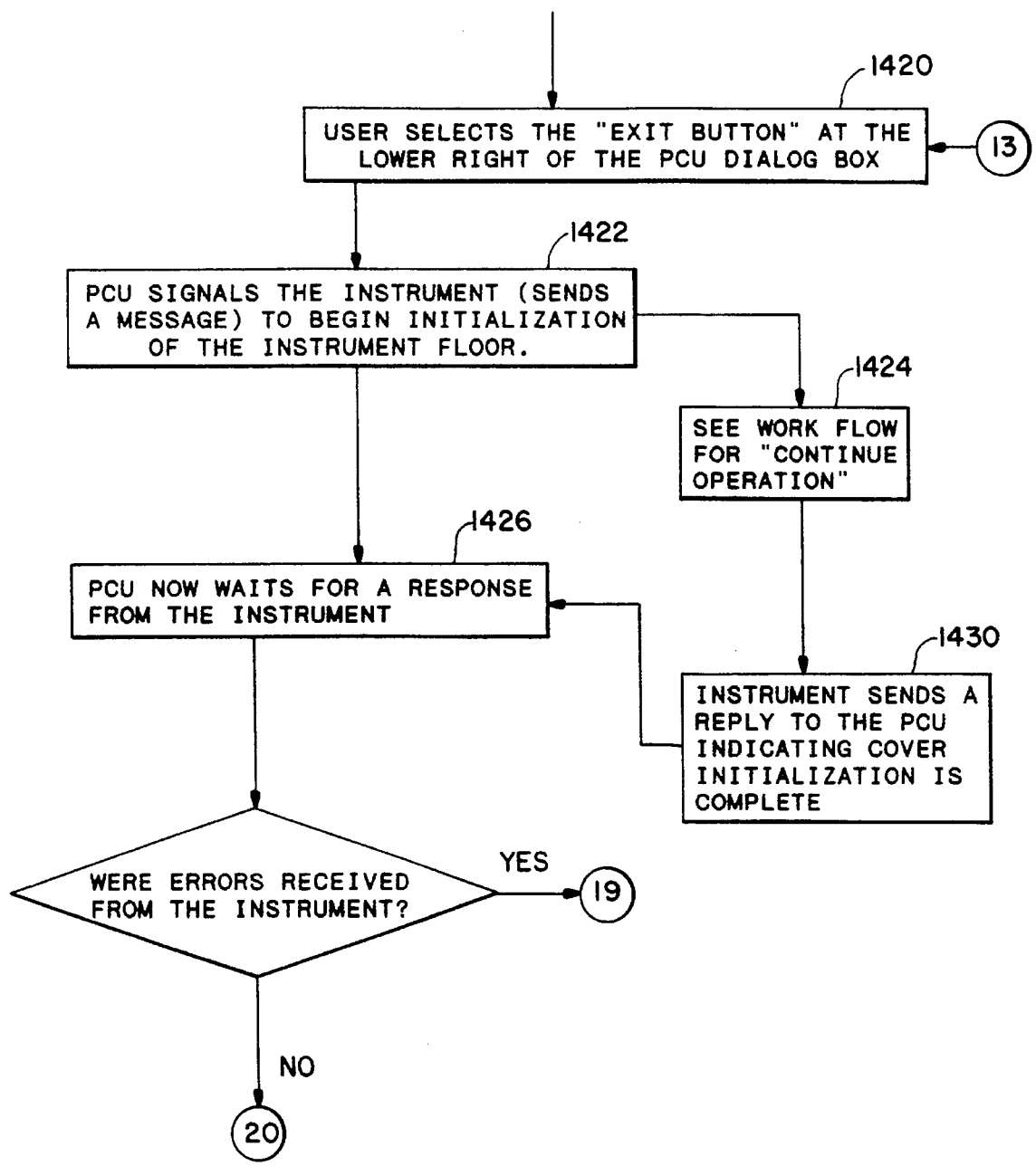
Figure 50:
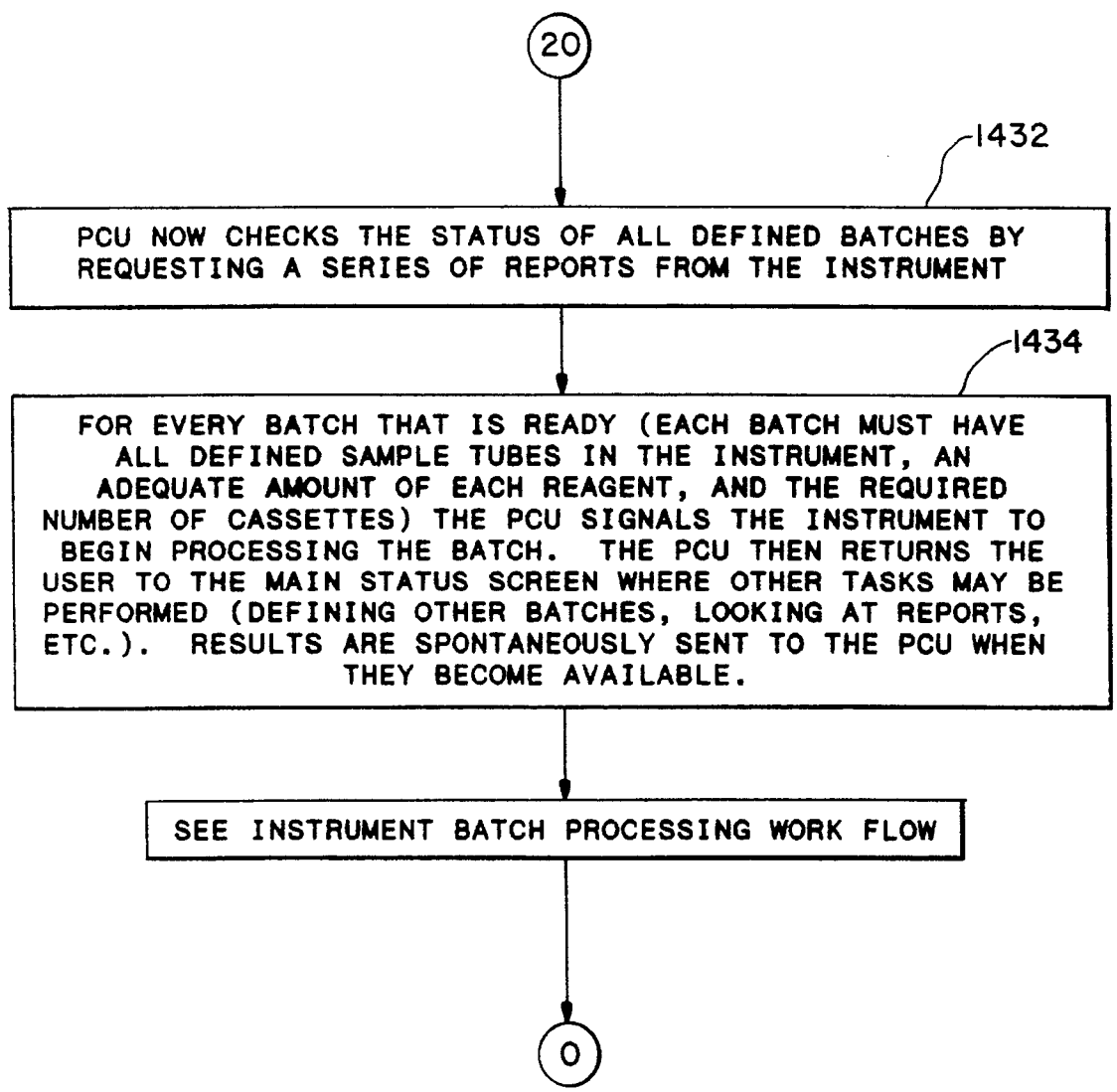
Figure 51:
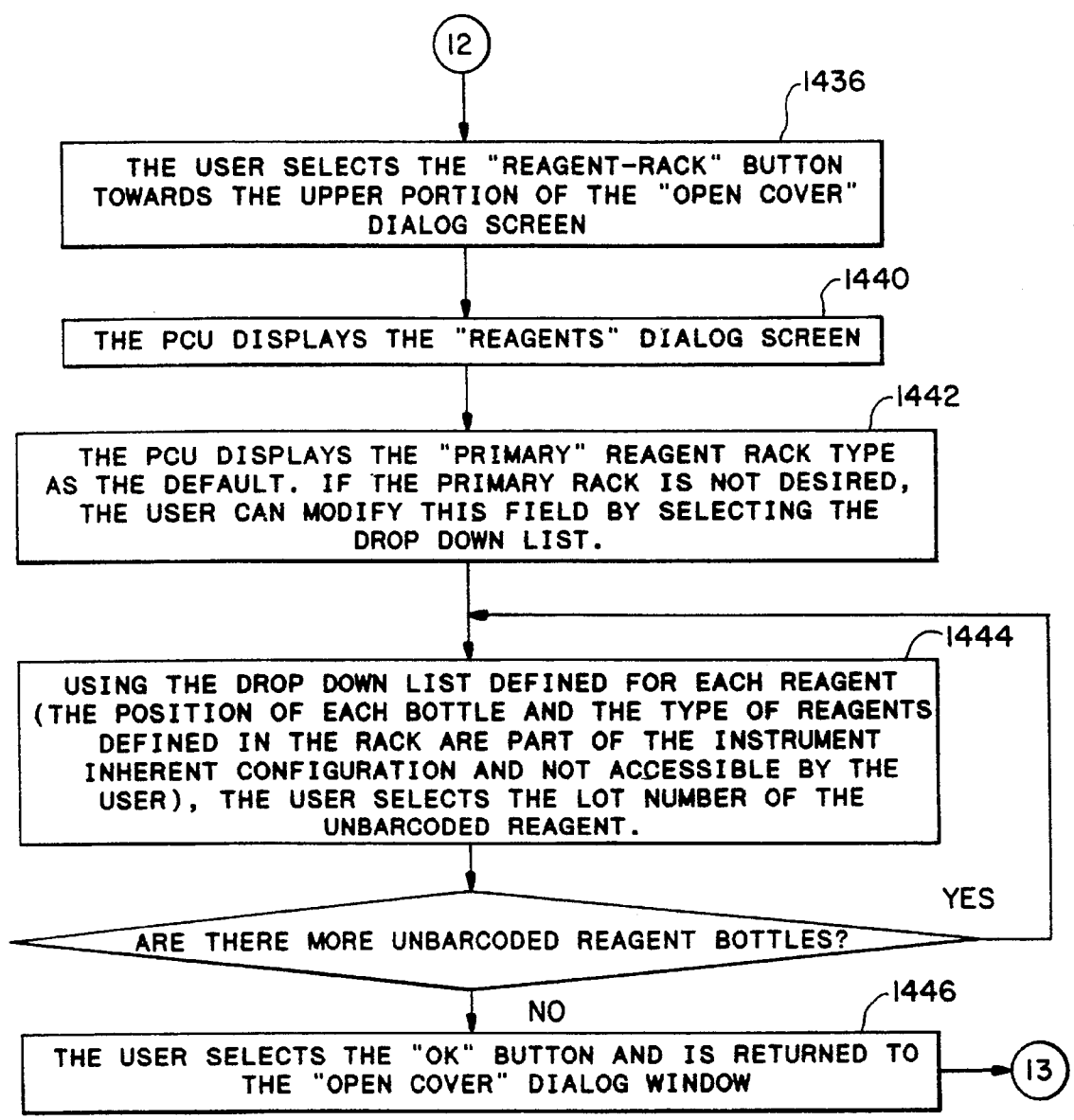

FIGS. 49–51 show the open instrument cover work procedure; and as previously mentioned, during this procedure the required reagents and microtiter plates are placed on the instrument. To begin this procedure, at step 1402, the user selects the "instrument" menu item from the PCU menu bar. The "instrument" menu is then displayed on the monitor at step 1404, and at step 1406 the user selects the "open cover" menu item. After this menu item is requested, the PCU sends a message at step 1410 to the instrument requesting the instrument to open the instrument cover. In response, at step 1412, the instrument cover is opened, and the instrument transmits to the PCU a signal confirming that this has been done.

Next, at step 1414, the PCU displays an "open cover" dialogue on the monitor, and this dialogue is or includes a logical representation of each module on the instrument accessible to the user. These modules include the reagent rotor, the sample rotor, and the special cassette racks. In addition, the display includes a logical representation of any cassettes, reagent, and sample tubes on the instrument.

At step 1416, the user places in the instrument two dilution racks, a reagent rack with the reagent bottles, and a sample rack with the sample tubes needed for the requested batches. After the reagent rack and bottles are placed on the instrument, the reagent rack is rotated to move each reagent bottle past the bar code reader, and the reader checks to determine whether each reagent bottle has a bar code. If any bottle does not have a bar code, a subroutine, discussed in detail below, is invoked. However, if all of the reagent bottles have bar codes, then the instrument cover work procedure proceeds to step 1420.

At this step 1420, the user sends a message to the PCU to begin the continue operation procedure, discussed above. Preferably, this message is sent to the PCU by means of a graphics interface on the monitor. For example, the "open cover" dialogue box on the PCU monitor may contain the term "exit," and the user may send the above-discussed message to the PCU by aligning a cursor, or other suitable indicator, with that exit term. The PCU, at step 1422, then transmits a message to the instrument to begin initialization of various modules; and the instrument then begins the Continue Operation procedure, as represented by step 1424.

After the continue operation procedure is completed, the STU at step 1430, sends a signal to that effect to the PCU. If any error messages were received by the PCU from the STU during operation of the continue operation procedure, then, after receipt of the signal indicating that the continue operation procedure is completed, the PCU returns to step 1410 of the instrument cover work procedure, and the PCU continues on from there.

If no such error messages were received by the PCU, then at step 1432, the PCU checks the status of all the defined batches by requesting a series of reports from the instrument; and, in particular, as represented by step 1434, the PCU checks to determine that, for each requested batch, all of the necessary sample tubes, reagents, and cassettes are in the instrument. For each batch test that is ready to be run, the PCU transmits a signal to the instrument to begin that test; and in particular, the PCU sends a signal to the instrument to begin the batch processing work procedure. In addition, the PCU produces the main screen display on the monitor, and the user continues to have access to the PCU to perform other tasks such as defining other batch tasks and looking at reports.

As mentioned above, if, at step 1416, a reagent bottle is found not to have a bar code, then a subroutine is invoked, and this subroutine is shown in FIG. 51. Preferably, this subroutine is invoked at step 1436 by the user sending the message to the PCU, and this also may be done by means of a graphics interface. For instance, the "open cover" dialogue on the PCU monitor may include a representation of a button or switch labeled "reagent-rack," and the user may transmit the above-discussed message to the PCU by aligning a cursor with this representation of the button. In response to this signal, the PCU, at steps 1440 and 1442, displays a dialogue, referred to as the "reagents" dialogue on the screen.

This reagents dialogue identifies each location on the reagent rack and includes a description of the reagent in that location. The dialogue also includes a list of all the reagent types that may be used on the instrument. For each reagent bottle that does not have a bar code, the user, at step 1444 identifies on the list on the dialogue, the type of reagent in that bottle. After the reagent type has been identified for each bottle that does not have a bar code, then at step 1446, the user transmits a message to the PCU, preferably also via graphics interface, to terminate this subroutine. Upon receipt of this message, the PCU returns to step 1420 of the open instrument cover work procedure.

Figure 52:
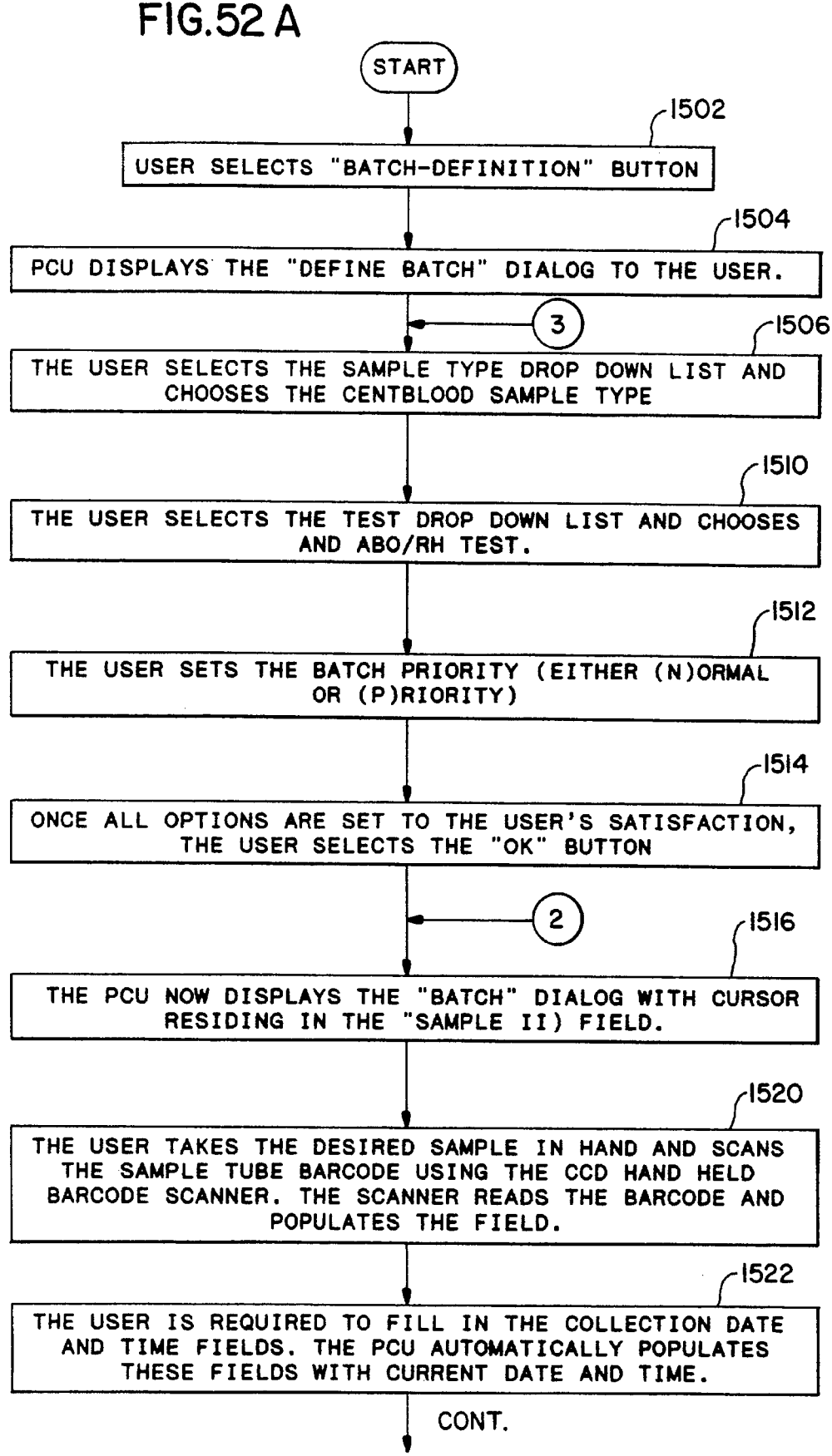
FIG. 52 shows a batch definition procedure for the blood analysis instrument.
Figure 52B:
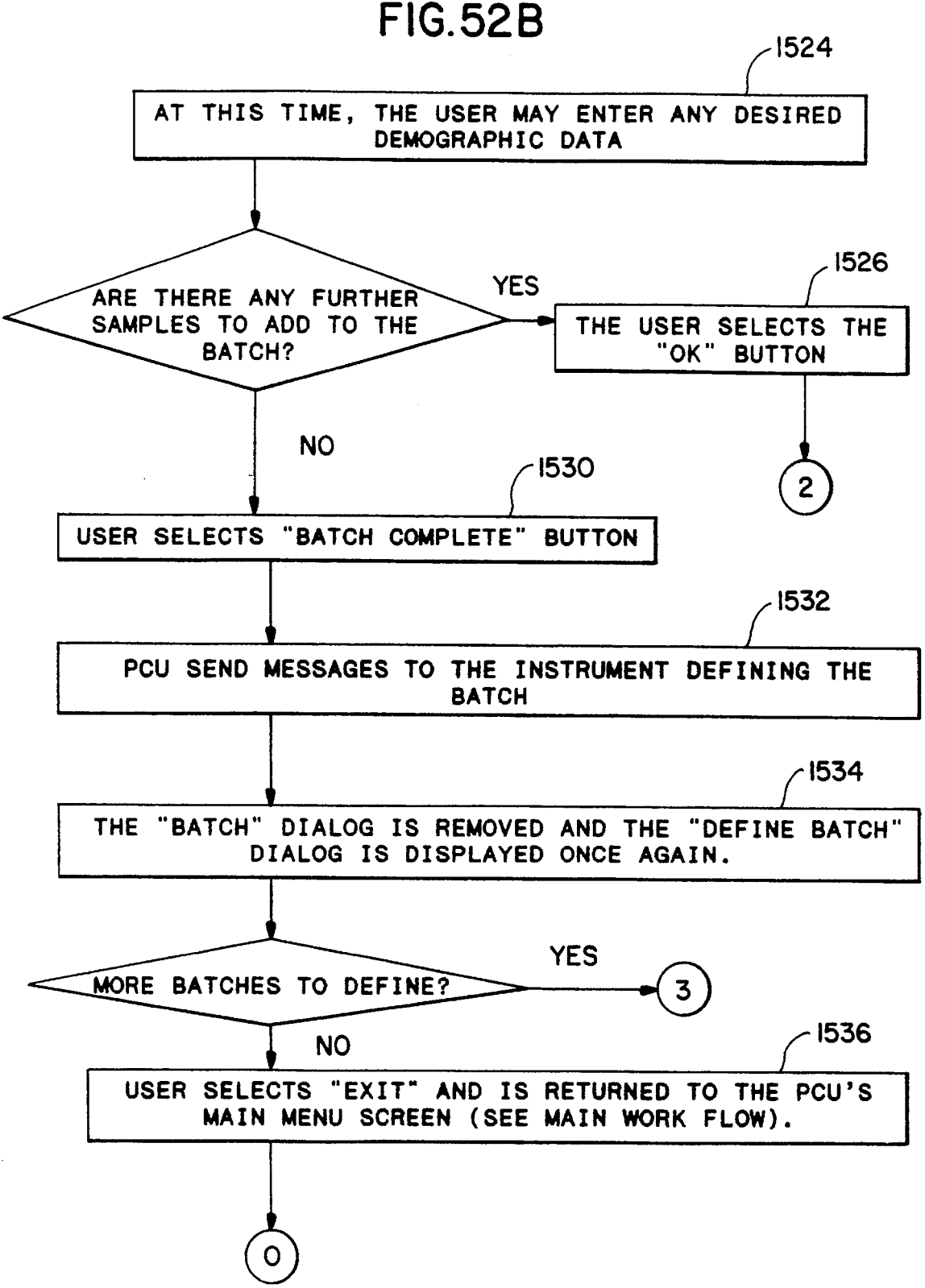

With reference to FIG. 52, the user initiates the batch definition work procedure at step 1502 by transmitting a signal to the PCU to do this. For example, the main menu screen display of the PCU main contain a logical representation of a button referred to as the "batch definition" button, and the user may initiation the batch definition work procedure by aligning a cursor with that batch definition button. In response to receipt of this signal, at step 1504 the PCU displays a "Define Batch" dialogue on the monitor. This dialogue includes a list of the various items that must be designated for each batch test, including the sample type, the test type, and the test priority. To designate the sample type, the user, at step 1506, transmits a signal to the PCU to display on the monitor a complete list of the possible sample types, and the user designates one of those types as the type that is to be used in the test presently being defined.

Similarly, to define the type of test, the user transmits a signal to the PCU at step 1510 to display on the monitor a complete list of the possible test types, and the user designates one of those types as the type of the test presently being defined. In addition, preferably, the test can be assigned either a normal or a high priority. The defined batch display includes logical representations of these two priorities, and at step 1512 the user designates or selects one of these logical representations on the monitor to identify to the PCU the type of priority to be given to the test being defined.

After all the test options have been selected, the user, at step 1514, transmits a signal to the PCU to indicate that this has been done, and preferably this is done via a graphics interface on the monitor. Then, at step 1516, the PCU displays another dialogue, referred to as the "Batch" dialogue, on the monitor, and the user at step 1520 then transmits to the PCU data relating to a blood sample to be tested in this particular batch test. For instance, preferably, a bar code is on the sample vial indicating various data, including an identification number for the vial, and a bar code scanner is traversed across that bar code to transmit those data to the PCU. As represented by steps 1522, and 1524, additional data items, such as the date and time the sample was collected, and any additional data that the user may consider appropriate, may be transmitted to the PCU via the keyboard.

If more than one blood sample is to be tested in this particular batch test, then the user, at step 1526, transmits a signal to the PCU to indicate that additional samples are to be added, and steps 1516–1524 are repeated, once for each additional blood sample. After the desired data has been entered for all the blood samples, the program moves on to step 1530. At this step, the user transmits a message to the PCU that the definition for this particular batch test has been completed; and, in response, the PCU transmits, at step 1532, a message to the instrument identifying all the steps needed to perform this batch of tests. Then at step 1534, the PCU removes the "Batch" dialogue from the monitor and displays the "defined batch" dialogue. If additional batch tests are to be defined, then steps 1506–1534 are repeated, once for each additional batch test that is to be defined. After all the batch tests have been defined, the user transmits a signal to the PCU at step 1536 to indicate completion of these definitions, and preferably this is done via graphics interface. In response to this message, the PCU terminates the batch definition work procedure, and the PCU displays the main menu screen on the monitor.

Figure 53A:
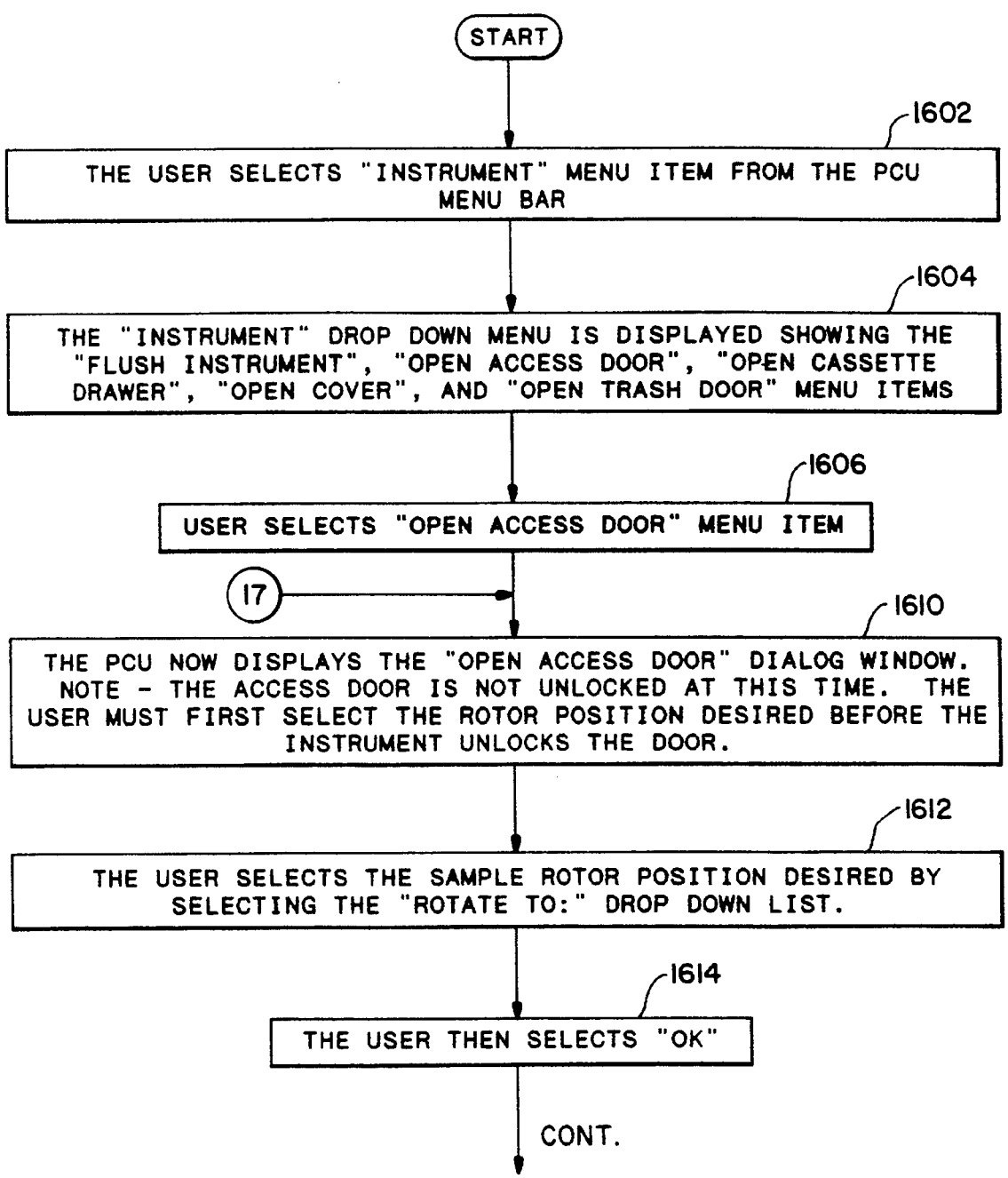
FIGS. 53 and 54 illustrate a sample access door procedure for the blood analysis instrument.
Figure 53B:
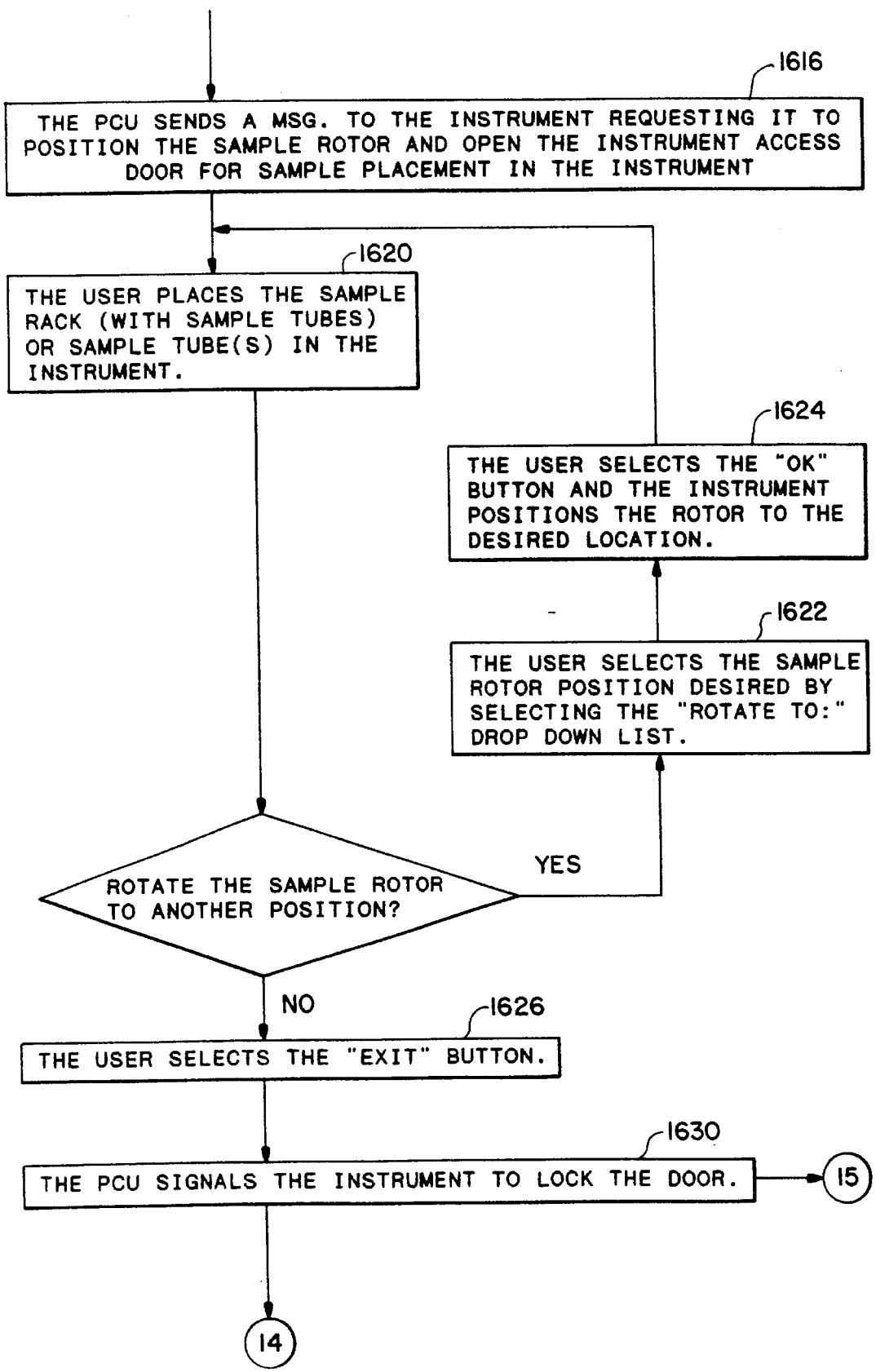
Figure 54:
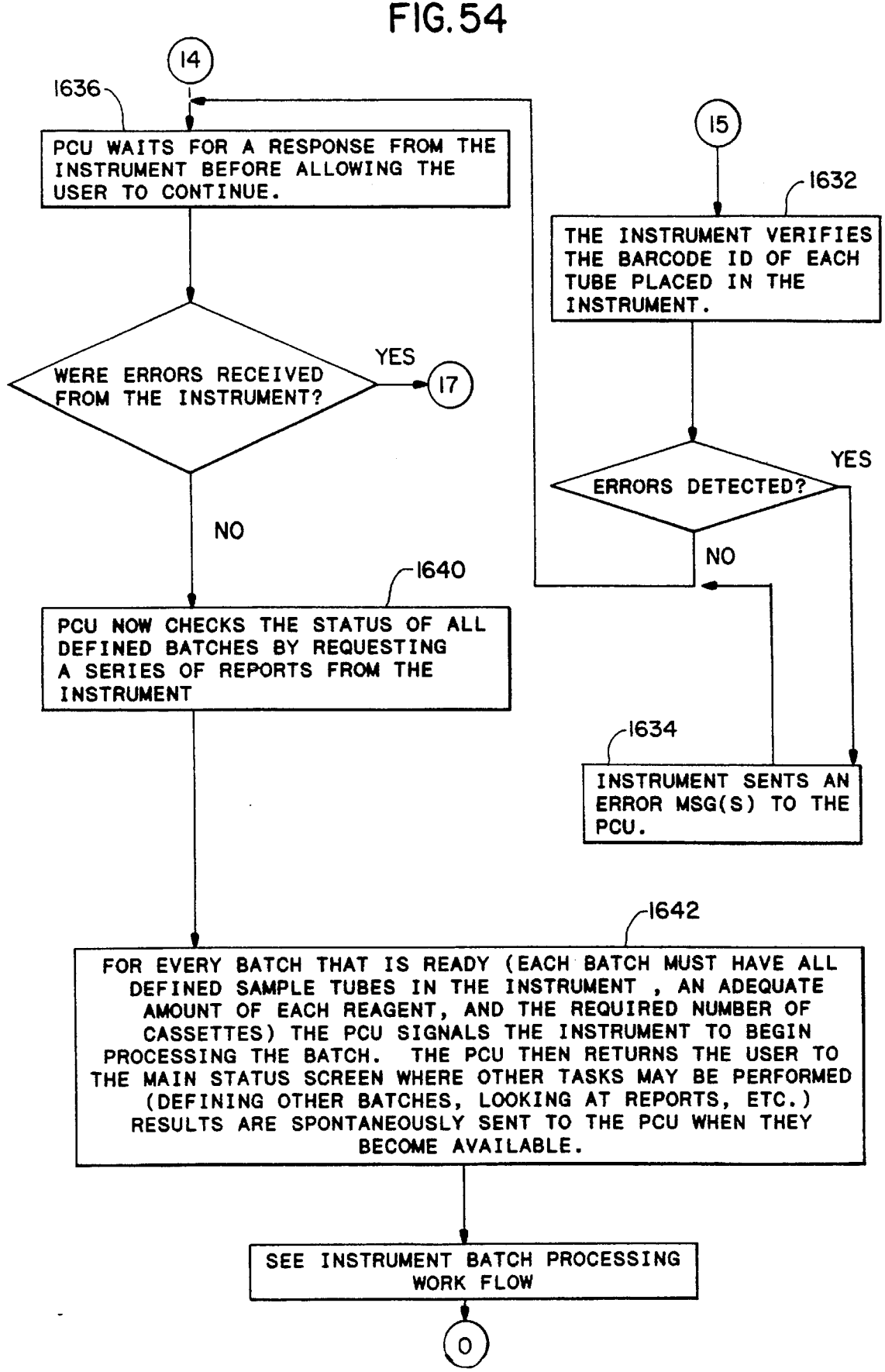
Figure 56A:
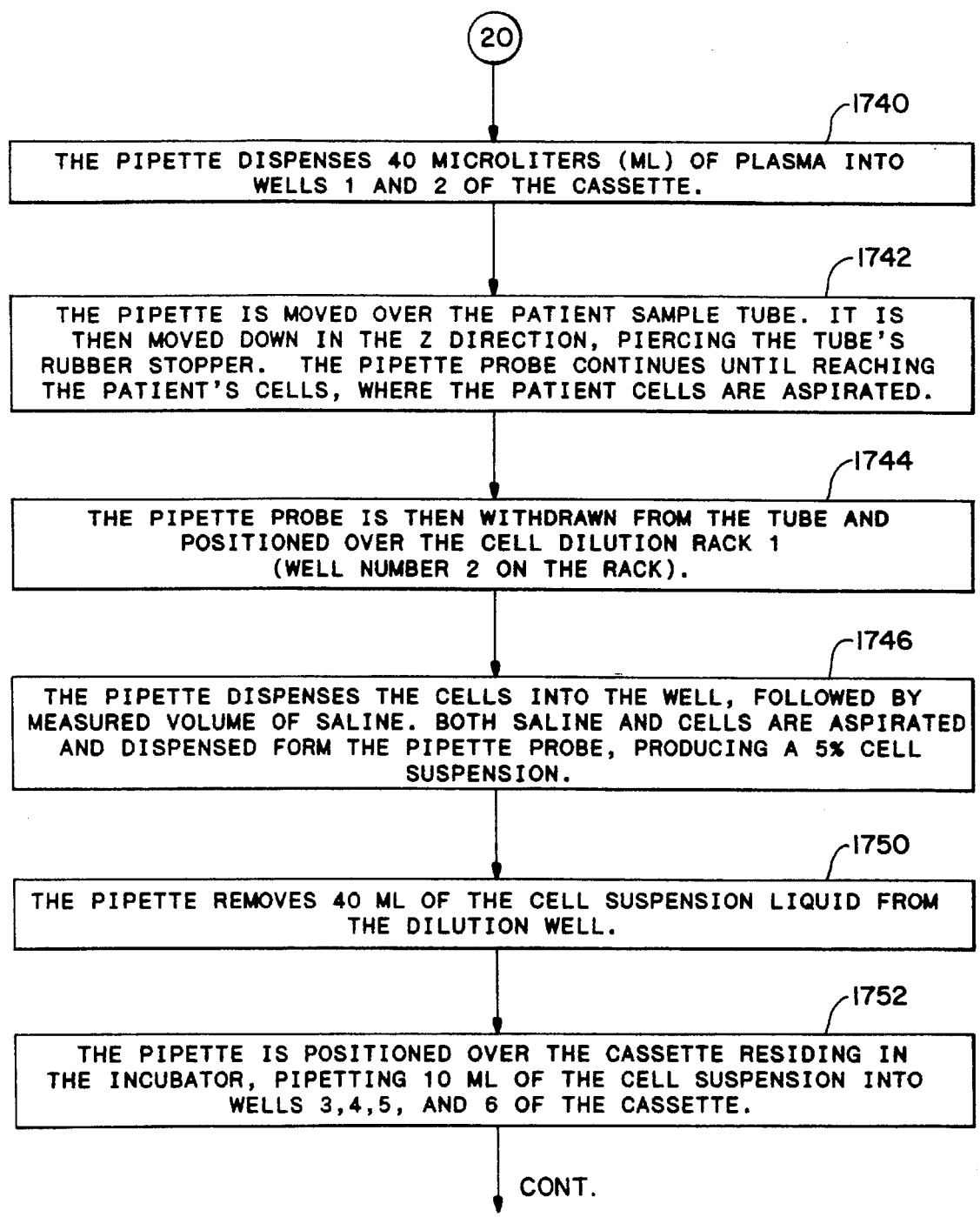
Figure 56B:
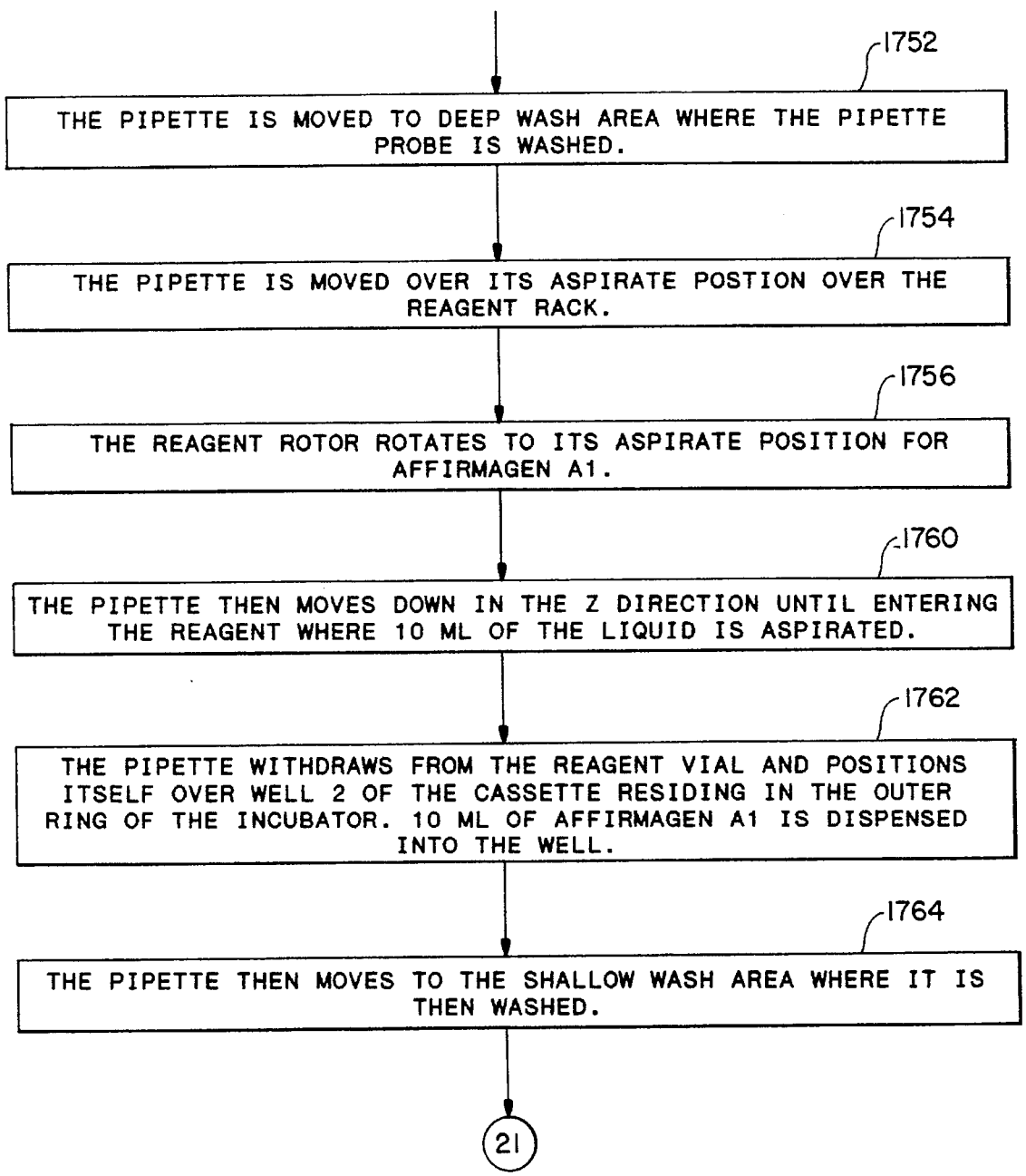
Figure 57A:
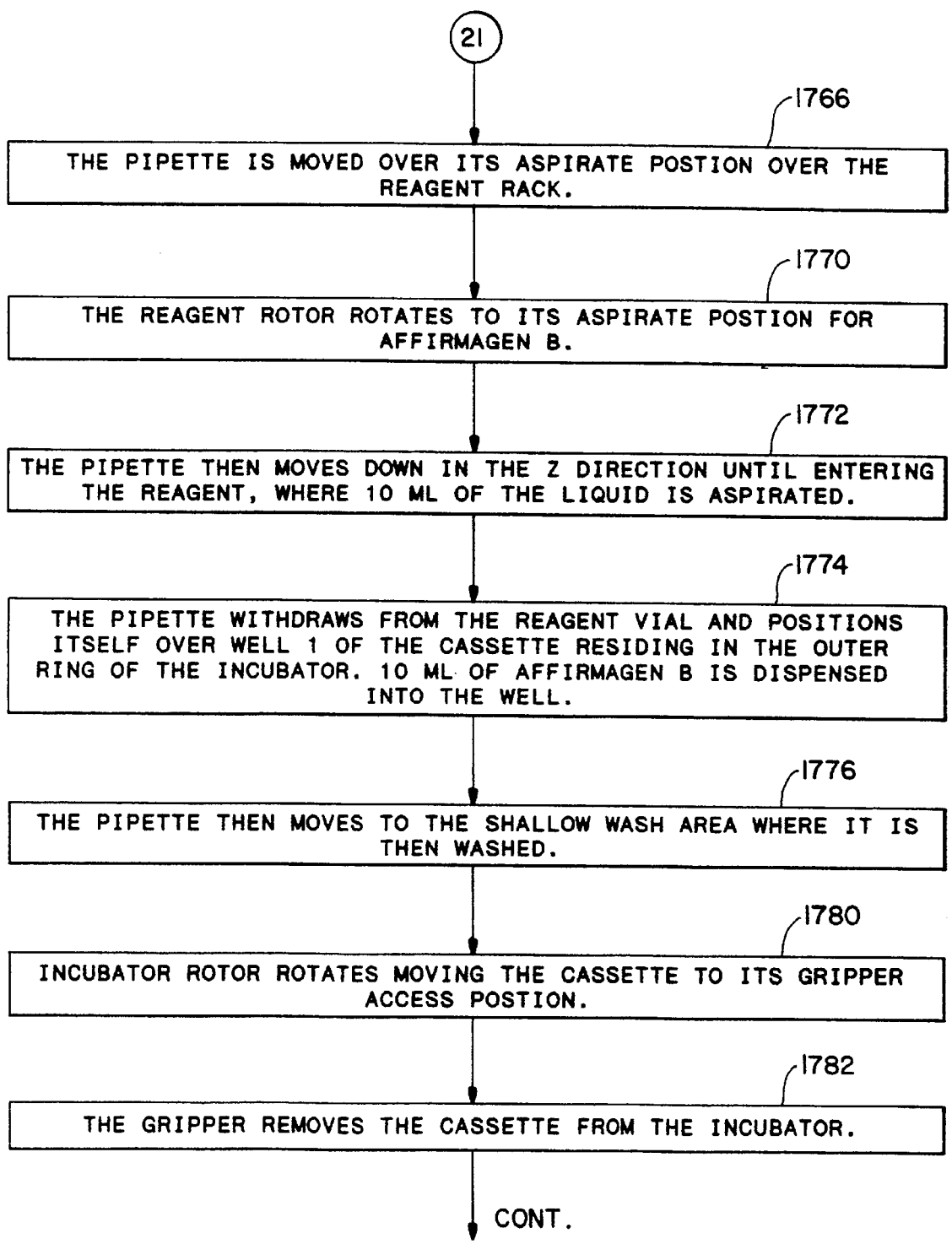
Figure 57B:
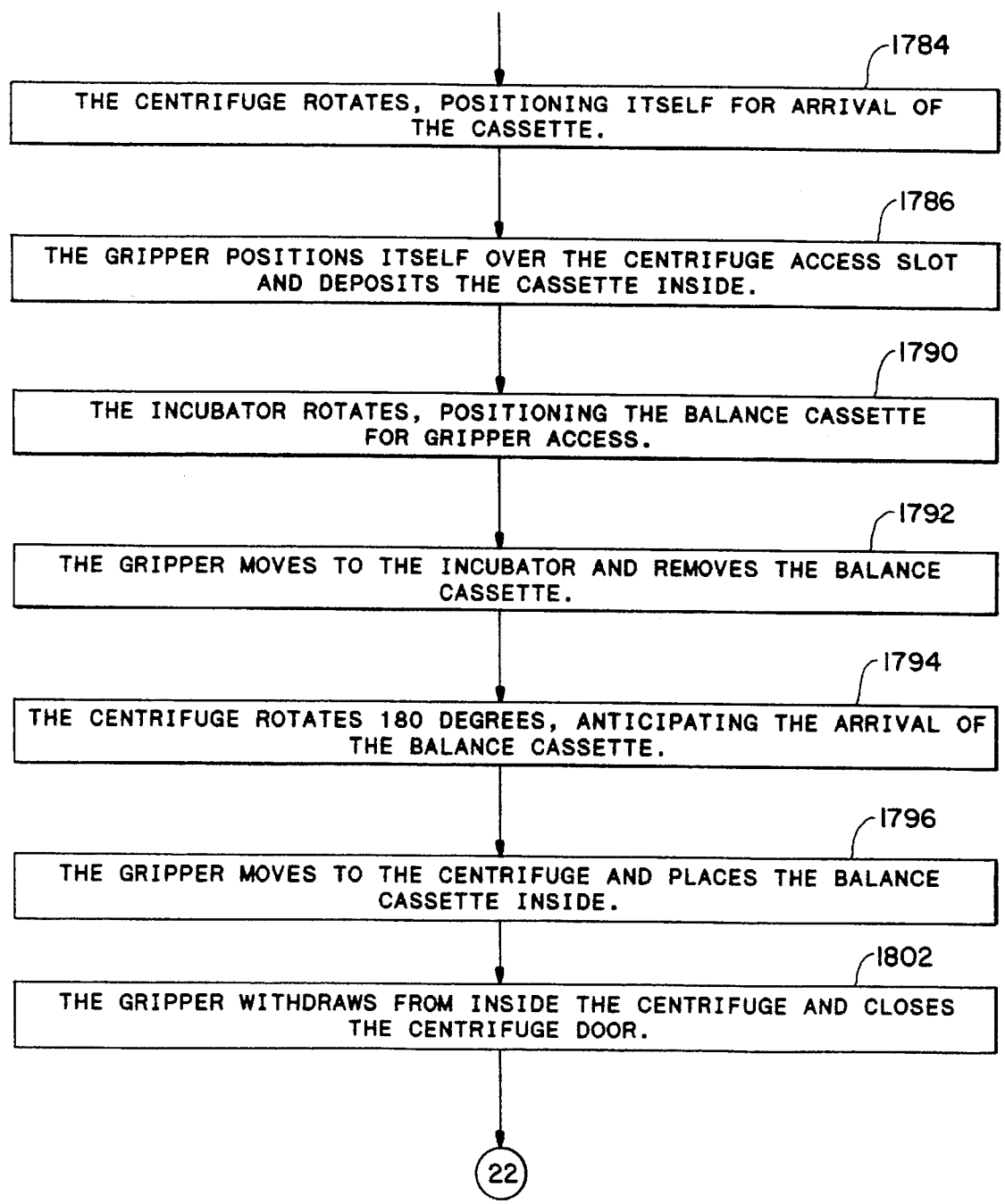
Figure 58B:
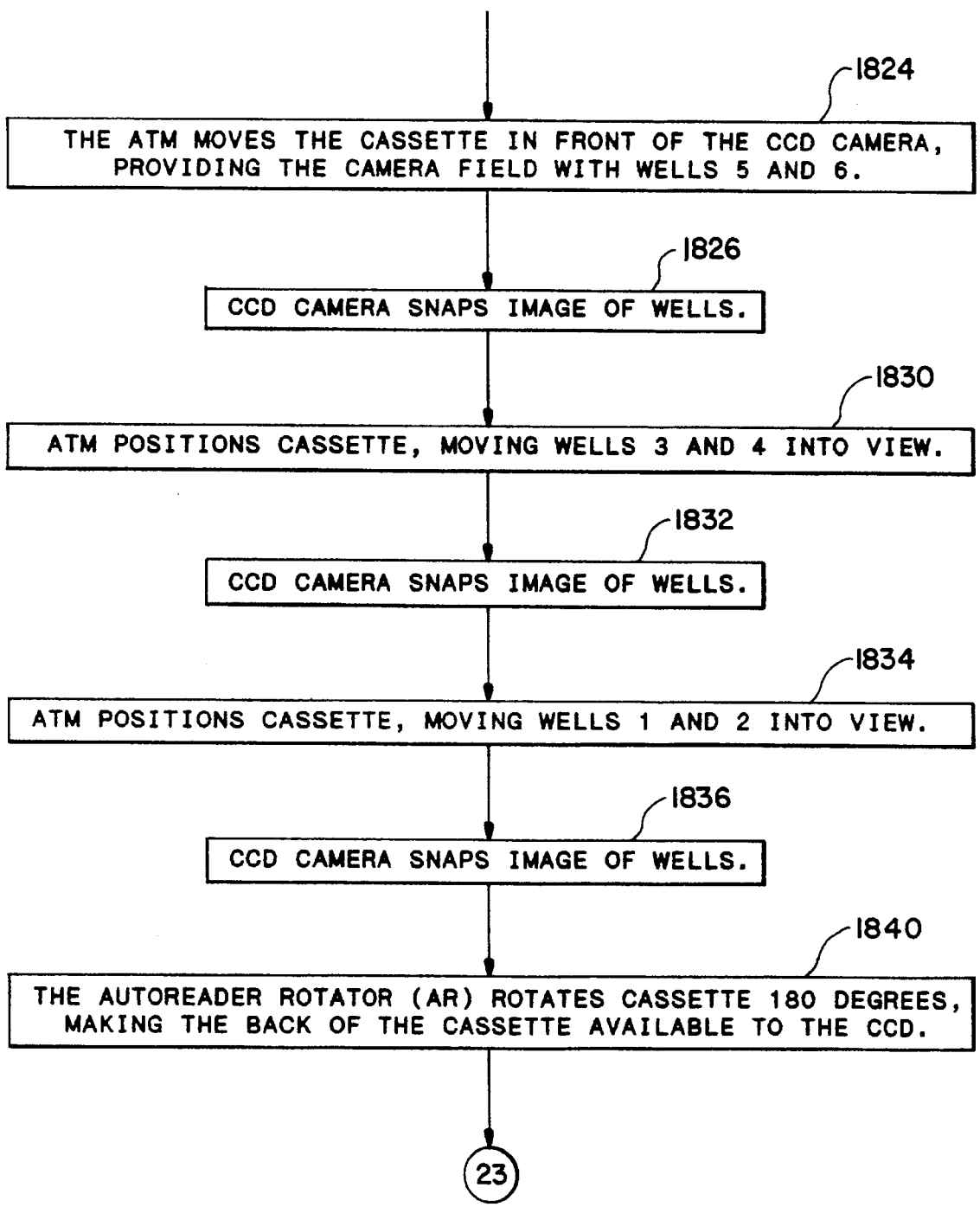
Figure 59:
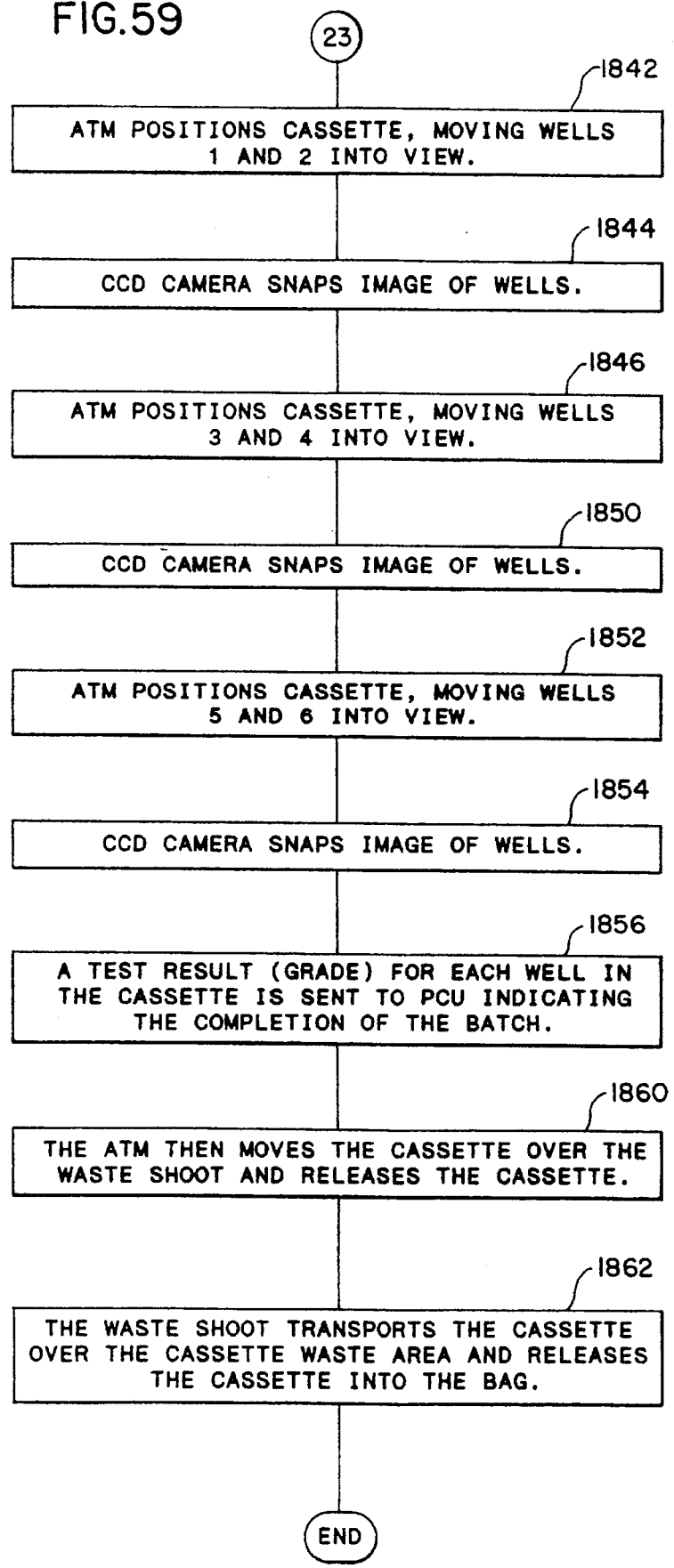

The sample access door procedure is illustrated in FIGS. 53 and 54. To initiate this procedure, the user, at step 1602, selects the "instrument" menu from the PCU menu bar. In response, the PCU displays the instrument menu at step 1604, and at step 1606 the user selects the "open access door" item from the instrument menu. At step 1610, the PCU then displays a dialogue, referred to as the "open access door" dialogue on the monitor, and this dialogue includes a logical representation of the sample rotor. On the screen, the user at steps 1612 and 1614, identifies or designates one of the positions of the rotor, and a message is sent to the PCU identifying this position in the rotor. In response, at step 1616, the PCU transmits a message to the instrument requesting it to position a sample rotor so that the identified rotor position is located below the access door for placement of the samples in the instrument, and also requesting the instrument to unlock and open that access door. The user at step 1620 then places in the rotor, either the sample tubes or sample rack with the sample tubes.

If additional sample tubes or sample racks are to be placed in the rotor, at step 1622, the user designates on the open access door dialogue the desired position on the rotor for these tubes or sample racks. In response to each such designation, the PCU at step 1624 transmits a message to the instrument to move the rotor so that the designated position is moved beneath the sample access door and that door is, if necessary, unlocked and opened. The user then places the sample tubes and racks in the designated positions. After the sample tubes have been placed in the rotor, the user sends a message at step 1626 to the PCU to indicate that this job has been completed. Preferably, this is done by means of graphics interface. For instance, the "open access door" dialogue may contain a logical representation of an exit button or switch, and the user may align a cursor or other indicator with that logical representation to transmit the above-mentioned message to the PCU.

In response to receipt of this message, the PCU transmits a message to the instrument at step 1630 to lock the sample access door. Also, at step 1632, the instrument then checks the barcode on each sample tube to determine where each tube has been placed. Preferably, this is done by rotating the sample rotor stepwise, so that each opening in the rotor is positioned in front of the bar code scanner, and the bar code reader then reads the bar code on the sample tube in each position. If any errors are detected, an error message is sent to the PCU at step 1634. After this verification is complete, a message is sent to the PCU to indicate this fact, as represented by step 1636.

If any error messages were received by the PCU while the instrument was verifying the bar code of each sample tube placed in the instrument, then, after receipt of the signal that this verification process is completed, the PCU returns to step 1610 of the access door work procedure, and continues on from there. However, if no such error messages were received by the PCU during this bar code verification procedure, then, after that procedure is completed, the PCU, at step 1640, checks the status of all of the defined batches by requesting a series of reports from the instrument. Specifically, as represented by step 1642, the PCU checks to determine that, for each requested batch, all of the necessary sample tubes, reagents, and cassettes are in the instrument. For each batch test that is ready to be run, the PCU sends a signal to the instrument to begin that test, and specifically, the PCU sends a signal to the instrument to begin the batch processing work procedure. Also, the PCU displays the main screen display on the monitor, and the user continues to have access to the PCU to perform other jobs such as defining additional batch tests and reviewing report results.

FIGS. 55. 59 illustrate the batch processing procedure, and this procedure is begun, at step 1702, when the instrument receives a message from the PCU instructing the instrument to start a specific batch. Then, at step 1704, the cassette drawer assembly positions one of the abo/rh→ABO/Rh cassettes therein for removal by the gripper. Specifically, this is done by moving the cassette slide tray so that the front cassette in the row of abo/rh→ABO/Rh cassettes is located in the gripper access position. At step 1706, the gripper then moves from its current position to a position over the cassette access opening and over the row of cassettes containing the abo/rh→ABO/Rh cassettes; and the gripper moves down, grips the front abo/rh→ABO/Rh cassette, and removes that cassette from the slide tray. Next, at step 1710, the gripper moves the cassette past the bar code reader; and at step 1712, the reader reads the bar code on the cassette to identify, for example, the recommended expiration date of the cassette, the identification of the cassette type, and other information about the cassette such as its manufacturing lot number and sequence number.

Then, at step 1714, the gripper moves the cassette over the outer ring of the incubator module, and at step 1716, the incubator rotates so that an available, open position therein is located below the gripper access opening. At step 1720, the gripper places the cassette in that incubator position, and then the gripper moves out of the incubator. Next, at steps 1722, 1724, and 1726, the incubator rotates to move the cassette beneath the foil punch, the foil punch punches openings in all six wells of the cassette, starting with the outer most well of the cassette, and then the incubator rotates to move the cassette beneath the pipette access opening.

In the next series of steps, the desired fluids from racks 302 and 304 are deposited in the cassette. More specifically, at steps 1730 and 1732, the sample rotor rotates to move the patient's sample tube into the aspirate position, and the tube down holder is activated to position the arm thereof over the patient's sample tube. At step 1734, the pipette is moved downward into the sample tube until the pipette reaches the patient's plasma and then 80 microliters of the plasma is aspirated into the pipette. Next, at steps 1736 and 1740, the pipette is moved over the first well of the cassette beneath the pipette access opening in the incubator, and the pipette dispenses 40 microliters of the plasma into each of the first and second wells of the cassette.

At step 1742, the pipette is moved back over the patient's sample tube in the sample rack and lowered back into that tube until the pipette reaches the patient's red blood cells, and those cells are aspirated into the pipette. At steps 1744 and 1746, the pipette is withdrawn from the patient's sample tube, positioned over a given well in the first cell dilution rack, and then dispenses the cells into that well. The pipette also dispenses a measured volume of saline into that well to produce a 5% cell suspension therein. After this, at step 1750 the pipette removes 40 microliters of the cell suspension liquid from the dilution well and dispenses 10 microliters of that cell suspension liquid into each of the third, fourth, fifth, and sixth wells of the cassette.

The pipette, at step 1752, is moved to and washed in the deep wash area, and then, at step 1754, the pipette is moved to the aspirate position over the reagent rack. The reagent rotor rotates the reagent rack at step 1756 to position the reagent bottle for Affirmagen A1 in the aspirate positions; and then at step 1760 the pipette is moved downward, in the z-direction, until entering the reagent, and 10 microliters of the reagent is aspirated into the pipette. At step 1762, the pipette is withdrawn from the reagent vial, is positioned over the second well of the cassette, and dispenses that 10 microliters of Affirmagen A1 into that cassette well. At steps 1764 and 1766, the pipette is moved to and washed in the shallow wash area, and then moved back to the aspirate position over the reagent rack.

The reagent rotor rotates the reagent rack, at step 1770, to position the reagent vial containing Affirmagen B in the aspirate position, and at step 1772, the pipette moves into that vial and withdraws 10 microliters of the liquid. At step 1774, the pipette is withdrawn from the vial, moved to a position directly over the first well of the cassette in the incubator, and dispenses the 10 microliters of the Affirmagen B into that well. The pipette is then moved to the shallow wash area and washed therein, at step 1776.

In the next series of steps, the cassette is moved to the centrifuge module and centrifuged therein. In particular, at step 1780, the incubator motor rotates the incubator to move the cassette to the gripper access position, and at step 1782 the gripper then removes the cassette from the incubator. The centrifuge rotates, at step 1784, to position itself for arrival of the cassette; and the gripper is positioned, at step 1786, over the centrifuge access slot and deposits the cassette in the centrifuge. The incubator rotates, at step 1790, to move a second cassette, referred to as a balance cassette—which may be a cassette without any reagents or fluids added to it—to the gripper access position. At step 1792, the gripper moves back to the incubator and removes the balance cassette therefrom via the gripper access opening. At steps 1794 and 1796, the centrifuge rotates 180°, and the gripper is moved back over the centrifuge access slot and deposits the balance cassette therein. After this, at step 1802, the gripper withdraws from the centrifuge and closes the centrifuge door.

At step 1804, the centrifuge then spins for two minutes at a slow speed, followed by a three minute spin at a fast speed; and after this, at step 1806, the centrifuge stops spinning and the centrifuge motor operates so that the centrifuge comes to a stop with the cassette being tested in the gripper access position. The gripper is then operated, at step 1810, to open the centrifuge door and to remove the test cassette from the centrifuge.

At steps 1812 and 1814, the autoreader rotor positions itself to accept the test cassette, and the gripper moves to the autoreader module and places the test cassette in the autoreader storage carousel. Afterwards, or while this is taking place, the centrifuge rotates to move the balance cassette to the gripper access position; and then at step 1816, the gripper is moved back to the centrifuge, removes the balance cassette therefrom, and carries that cassette to, and deposits it back in, the incubator.

At step 1820, the autoreader transport or mover 662 slides over the autoreader carousel; and at step 1822, the autoreader storage carousel rotates to move the test cassette to a position adjacent to the frame 632. Then, at step 1824, the autoreader transport operates to carry the test cassette from the carousel and into the autoreader holding frame, in a position such that an image of the fifth and sixth wells in the cassette is produced on the camera CCD. An image of these two wells is taken at step 1826; and, at step 1830, the transport moves the cassette so that the third and fourth wells of the cassette are in the camera view, and at step 1832, an image of these two wells is taken. Next, at steps 1834 and 1836, the autoreader transport moves the test cassette so that the first and second wells in the cassette are in the camera view, and an image of these two wells is taken. After this, at step 1840, the test cassette is rotated 180°, making the back of the cassette available to the camera. Then, as represented by steps 1842–1854, images are taken of the first and second wells, of the third and fourth wells, and of the fifth and sixth wells of the cassette, with the autoreader transport moving the test cassette, before each image is taken, to position the desired pair of wells in the camera view.

The data obtained from the images are processed at step 1856 to determine if any reaction occurred in each of the wells of the test cassette, and, if so, to determine the strength of that reaction. After the desired data processing is completed, a test result for each well in the cassette is sent to the PCU, and a further message is sent to the PCU indicating the completion of the batch test. The autoreader transport, at step 1862, then removes the test cassette from the frame and deposits the cassette in the waste receptacle.

Figure 60:
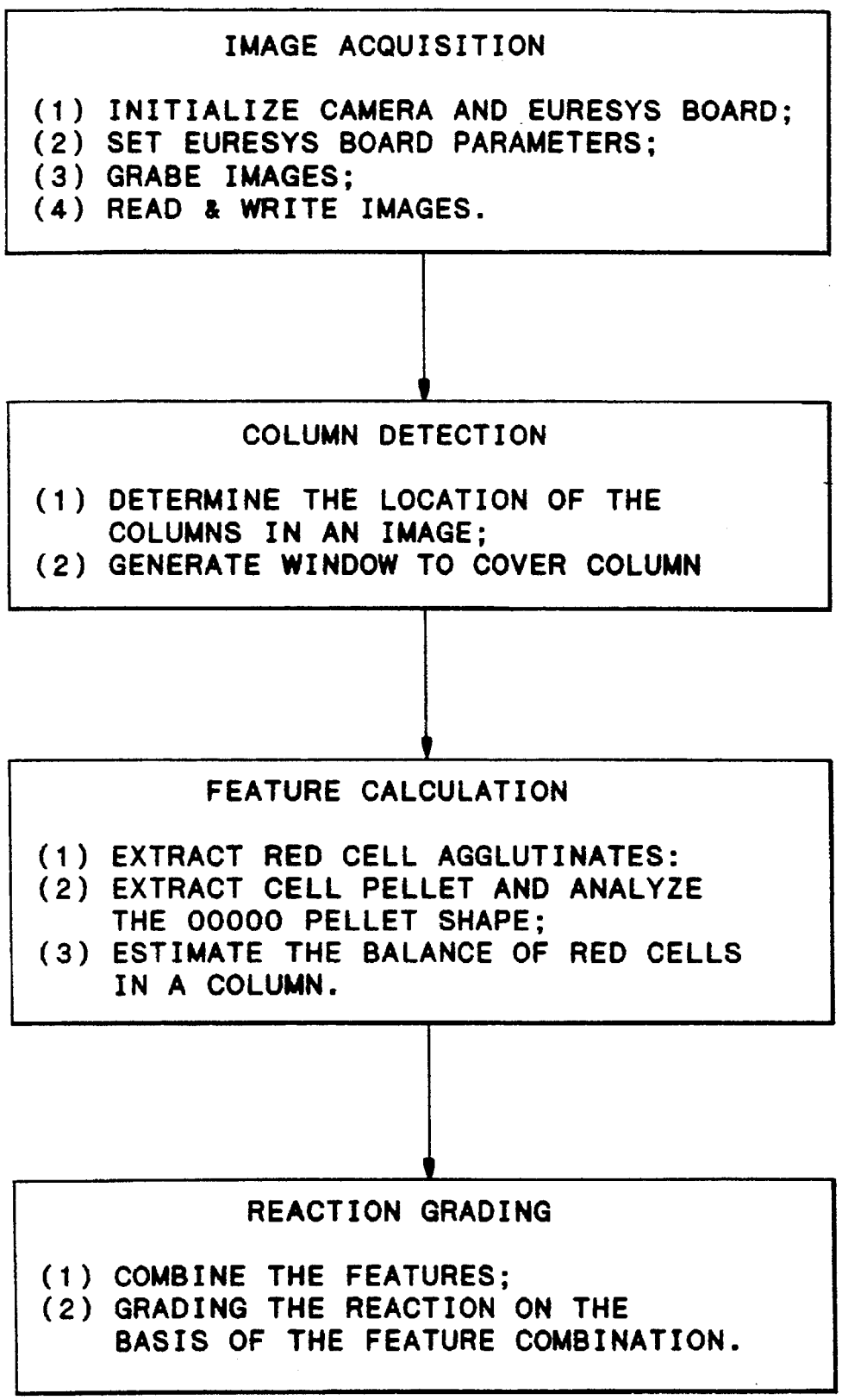
FIG. 60 outlines a procedure for analyzing the optical image produced in the blood analysis instrument.

FIG. 60 generally outlines a procedure for analyzing the image produced on the camera to classify the reaction that occurred in the test cassette. In the first part of this procedure, represented by box 1880, the image of the cassette is produced on the pixel array, and each pixel is assigned a data value representing the intensity of the image on the pixel. Then, as represented by box 1882, the image processing program searches for the location of each column in the source image on the pixel array; and after a column is located, the program generates a window to cover the bead area where the red cells are located.

For the feature calculation, represented by box 1884, the program begins to extract features related to the reaction that occurred in the column. The features extracted include (1) parameters related to the cell pellet shape; (2) the red cell agglutinates in the column; and (3) the side to side balance of red cells in the column. The cell pellet in the bottom of the column is first obtained by applying a global threshold in the V shape region of the column; and to analyze the pellet shape, the upper border of the cell pellet is fitted with a linear line.

Subsequently, a fixed mask is used to cover the whole column area, and then the program extracts the number of red cell agglutinates and their distribution in the column. For this purpose, the bead column is divided into five zones referred to as the positive zone, the negative zone and three intermediate zones. Generally, the positive zone is defined so as to contain the surface are on the top of the glass beads, and the negative zone is defined as the cell pellet area. The bead area between the positive and negative zone is divided into three areas to form the intermediate zones. The next step in the program is to determine the number of pixels in the positive zone that are illuminated at an intensity below a given value, and then the number of red cell agglutinates located in each of the intermediate zones is determined by means of an operation referred to as a top-hat operation. The feature calculation program then examines the balance of agglutinates between the left and right halves of the column.

For each column, the above parameters are preferably calculated for both the front and back side images of the column. As represented by box 1886, the two calculated values for each parameter are combined, and the agglutination reaction is then classified on the basis of these combined features.

A preferred procedure for processing the image data is described in more detail in copending application Ser. No. 08/163,996, for "Method and System for Classifying Agglutination Reactions," filed herewith, now U.S. Pat. No. 5,594,808, the disclosure of which is herein incorporated by reference.

Figure 61B:
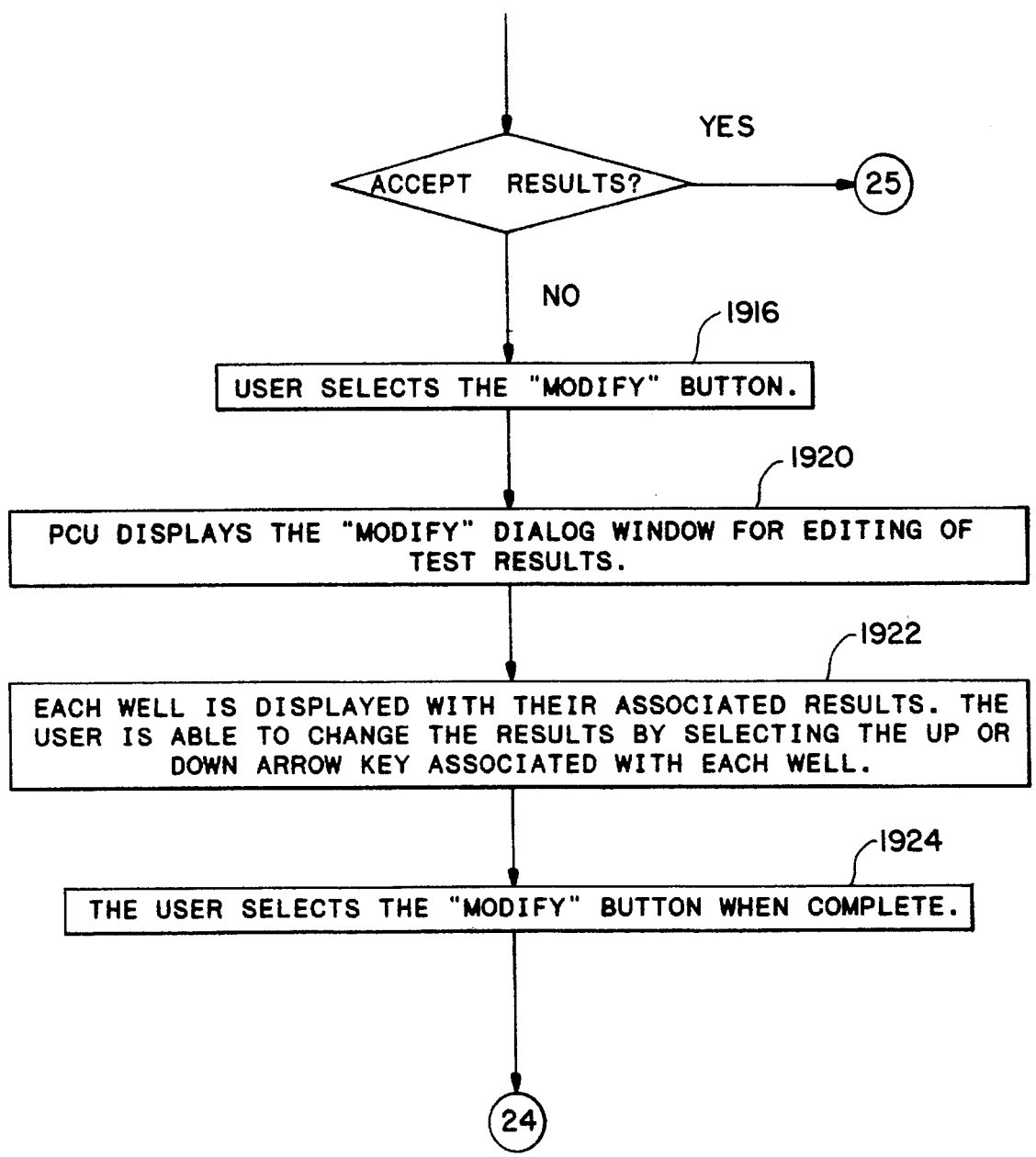
FIGS. 61 and 62 show a Reviewing Results procedure for the blood analysis instrument.
Figure 62:
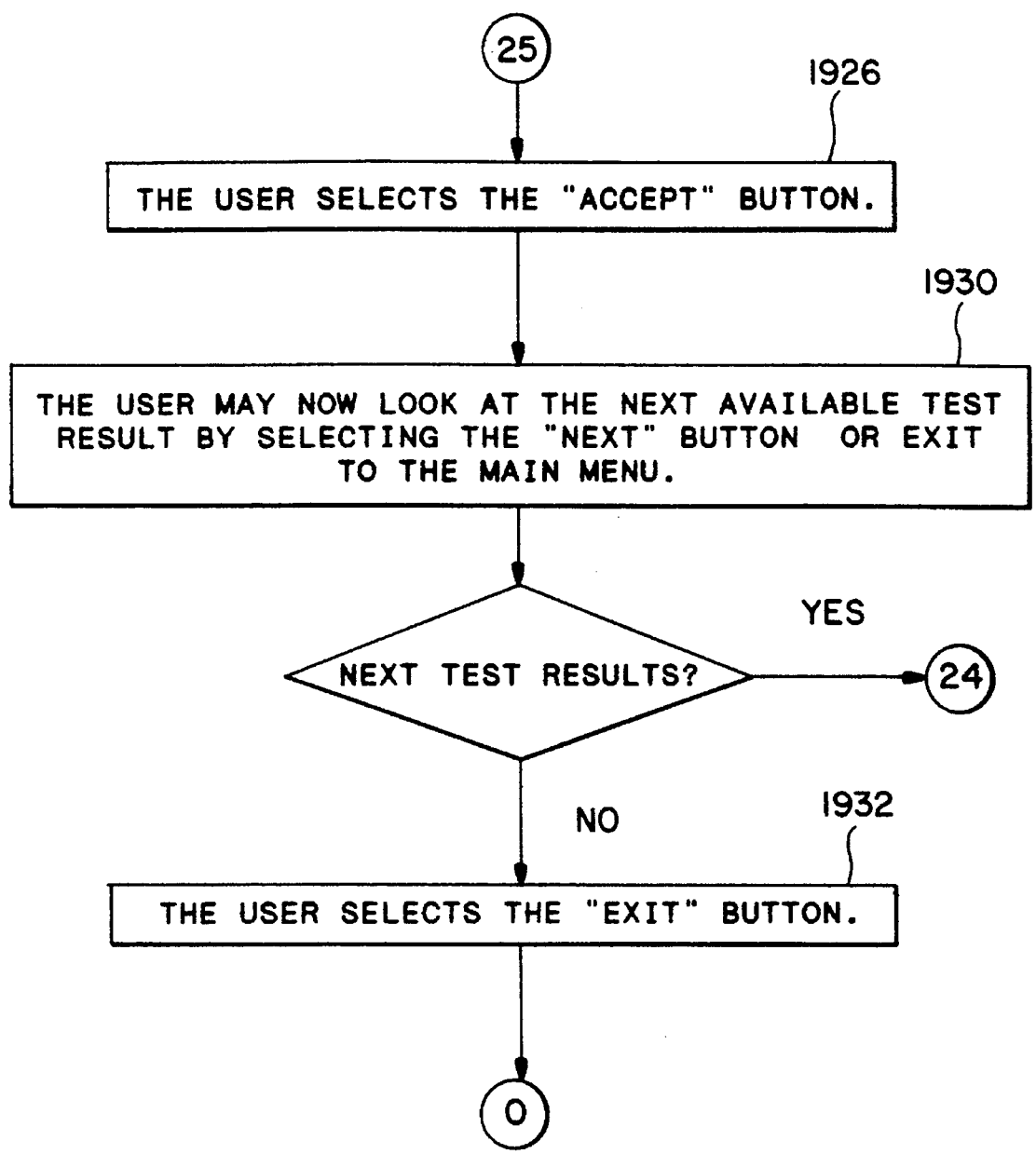

The reviewing results procedure is illustrated in FIGS. 61 and 62. The PCU maintains a current record of the status of each batch test and of the status of each test in each batch. As represented by steps 1902 and 1904, when a batch of tests is being performed, that batch and the individual tests in the batch have a status referred to as "running"; and when the batch of tests is completed, the status of the batch changes from "running" to "finished" and the status of the individual tests in the batch change from "running" to "completed."

Preferably, the PCU produces a display on the monitor that lists all of the tests being performed by the instrument and the current status of each test, and the display also includes a logical representation of a button or switch referred to as the "results" button. As represented by steps 1906 and 1910, to observe the results of a completed test, the operator uses graphics interface, first, to identify or designate that test on the list on the graphical display, and second, to designate the "results" button. In response, the PCU, at step 1912, then produces a dialogue on the monitor, referred to as the "results" dialogue that shows the grade of the reaction in each well of the test cassette.

Preferably, as represented by step 1914, the user has the option of modifying or altering the records of the test results, and this also may be done by graphics interface. More specifically, the "results" dialogue also contains a logical representation of a button or switch referred to as the "modify" button; and to initiate this modify procedure, the user, at step 1916, designates or identifies that button on the display. In response, at step 1920, the PCU produces a dialogue referred to as a "modify" dialogue that contains logical representations of a number of editing features that allow the user to alter the grade of the reaction in each well of the test cassette. For example, the "modify" dialogue may include a display of each well associated with both up and down arrows; and the user, at step 1922, is able to increase or decrease the reaction grade by selecting or designating the associated up or down arrow, respectively. At step 1924, the user indicates to the PCU that the modification procedure is complete by again selecting or designating the "modify" button on the "results" dialogue.

Preferably, the "results" dialogue also includes logical representations of buttons or switches referred to as "accept," "next," and "exit." When the displayed test results are acceptable, the user selects the accept button on the dialogue at step 1926, and the user selects the "next" button to display the results of a next test at step 1930. If the user selects this latter option, steps 1912–1930 are repeated, with the PCU displaying the results of that next test. If the user does not want to view any additional test results after step 1930, then the exit button is selected at step 1932, and the reviewing results work program terminates.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed is:

1. A method for automatically analyzing aqueous solutions, comprising
   depositing a multitude of containers in a first station said first station having (i) a multitude of container holders for simultaneously holding a multitude of containers, (ii) a container receiving and discharging position, and (iii) a fluid receiving position, said depositing step including the steps of, for each of the multitude of containers.
   (i) moving one of the container holders of the first station to the container receiving and discharging position, and
   (ii) depositing one of the containers into said one of the container holders;
   holding reagents and sample solutions at a second station;
   supporting a pipette assembly for three dimensional movement between the first and second stations;
   for each of the multitude of containers,
   i) moving the first station to move the container to the fluid receiving position,
   ii) operating the pipette assembly to draw reagent and sample solution from the second station, and to dispense the drawn reagent and sample solution into the container to form a test solution therein when the container is in the fluid receiving position,
   iii) after the container has received reagent and sample solution, moving the first station to move the container to the container receiving and discharging position, and
   iv) when the container is in the container receiving and discharging position, removing the container from the first station;
   positioning the removed containers in a centrifuge;
   centrifuging the containers in the centrifuge;
   positioning the containers in an auto reader station;
   analyzing the containers to identify reactions therein at the auto reader station;
   supporting a transport assembly for three dimensional movement between the first station, the centrifuge and the auto reader station; and
   operating the transport assembly to transport the containers from the first station to the centrifuge after the test solutions have been formed in the containers, and to transport the containers from the centrifuge to the auto reader station.

2. A method according to claim 1, wherein the centrifuging step includes the steps of:
   centrifuging the containers at a first, lower speed for a first period of time; and
   then centrifuging the containers at a second, higher speed for a second period of time.

3. A method according to claim 1, further including the steps of:
   transmitting data to a control unit to identify a batch of tests; and
   wherein the step of operating the pipette assembly includes the step of, the control unit transmitting control signals to the pipette assembly to operate the pipette assembly to form test solutions, determined by the control unit, in the containers.

4. A method for automatically analyzing blood samples comprising:
   storing a supply of cassettes in a drawer assembly;
   depositing a multitude of cassettes in a first station, said first station having (i) a multitude of cassette holders for simultaneously holding a multitude of cassettes, (ii) a cassette receiving and discharging position, (iii) a fluid receiving position, and (iv) a cassette opening position, said depositing step including the steps of, for each of the multitude of cassettes,
   i) moving one of the cassette holders of the first station to the cassette receiving and discharging position,
   ii) depositing one of the cassettes into said one of the cassette holders,
   iii) moving the first station to move said one of the cassettes into the cassette opening position, and
   iv) forming an opening in said one of the cassettes;
   holding reagents and blood samples at a second station;
   transmitting data to a control unit identifying a batch of tests for the blood samples;
   supporting a pipette assembly for three-dimensional movement between the first and second stations;
   for each of the multitude of cassettes,
   i) moving the first station to move the cassette to the fluid receiving position,
   ii) the control unit operating the pipette assembly to draw reagent and a blood sample from the second station, and to dispense the drawn reagent and blood sample into the cassette to form a selected test solution therein when the cassette is in the fluid receiving position,
   iii) after the cassette has received reagent and the blood sample, moving the first station to move the cassette to the cassette receiving and discharging position, and iv) when the cassette is in the cassette receiving and discharging position, removing the cassette from the first station;

positioning the removed cassettes in a centrifuge;

centrifuging the cassettes in the centrifuge;

positioning the cassettes in an auto reader station;

analyzing the cassettes at the auto reader station to identify reactions in the cassettes;

supporting a transport assembly for three dimensional movement between the drawer assembly, the first station, the centrifuge and the auto reader station; and the control unit operating the transport assembly to remove selected cassettes from the drawer assembly and to deposit the selected cassettes in the first station; the control unit further operating the transport assembly to transport the cassettes from the first station to the centrifuge after the selected test solutions have been formed in the cassettes, and to transport the cassettes from the centrifuge to the auto reader station.

5. A method according to claim 4, wherein the cassettes have top covers, and the forming step includes the step of piercing openings in the top covers of the cassettes.

6. A method according to claim 5, further including the step of, the control unit operating the drawer assembly to move the selected cassettes to a given position in a given order.

7. A method of operating a station in a medical fluid analysis instrument, the station having a multitude of cassette holders for simultaneously holding a multitude of cassettes, a cassette receiving and discharging position, a cassette opening position, and a fluid receiving position, the method comprising:

moving the cassette holders into the cassette receiving and discharging position;

depositing a plurality of cassettes into the cassette holders: and for each of said plurality of cassettes, i) moving the station to move the cassette to the cassette opening position, ii) forming an opening in the cassette, iii) moving the station to move the cassette to the fluid receiving position, vi) dispensing fluids into the cassette when the cassette is in the fluid receiving position, v) after the cassette has received said fluids, moving the station to move the cassette to the cassette receiving and discharging position, and vi) when the cassette is in the cassette receiving and discharging position, removing the cassette from the station.

8. A method according to claim 7, wherein the station includes a piercing assembly to form openings in the cassettes, and wherein the forming step includes the steps of:

moving the cassette beneath the piercing assembly; and operating the piercing assembly to form openings in the cassettes.

9. A method according to claim 8, wherein for each of the plurality of cassettes, the moving step includes moving one of the cassette holders into the cassette receiving and discharging position; and the depositing step includes depositing the cassette in said one of the cassette holders.

* * * * *